(12) United States Patent
Sakai et al.

(10) Patent No.: US 7,582,817 B2
(45) Date of Patent: Sep. 1, 2009

(54) ALTERATION OF PLANT EMBRYO/ENDOSPERM SIZE DURING DEVELOPMENT

(75) Inventors: Hajime Sakai, Newark, DE (US); Nobuhiro Nagasawa, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 77 days.

(21) Appl. No.: 11/378,920

(22) Filed: Mar. 17, 2006

(65) Prior Publication Data

US 2006/0218674 A1    Sep. 28, 2006

Related U.S. Application Data

(60) Provisional application No. 60/664,512, filed on Mar. 23, 2005.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .................. 800/320.2; 536/23.6; 800/298; 800/287; 435/419; 435/320.1; 435/415

(58) Field of Classification Search .................. None
See application file for complete search history.

(56) References Cited

U.S. PATENT DOCUMENTS 5,629,175 A * 5/1997 Goodman et al. .......... 435/69.1

OTHER PUBLICATIONS

Ma, et al. EST database. Accession No. CL977211, submitted Sep. 21, 2004.*
Spencer et al, (Segregation of transgenes in maize. (1992) Plant Molec. Biol. 18:201-210.*
Colliver et al (1997, Plant Mol. Biol. 35:509-522).*
Montgomery et al (Trends in Genetics, Jul. 1998, 14(7):255-258).*
Ma et al (Sep. 2004, NCBI Accession No. CL977211).*
Database Uniprot LOB Domain-Containing Protein 18, Jun. 1, 2002, Database Accession No. O22131, XP002393120.
Database Uniprot *Oryza sativa* LOB Domain Protein, Oct. 1, 2003, Database Accession No. Q7XGL4, XP002393121.
Kitano et. al., Hierarchical Regulation of Organ Differentiation During Embryogenesis in Rice, Plant J., 1993, vol. 3:607-610.
Hong et. al., Phenotypic Diversity of 188 Rice Embryo Mutants, Dev. Genet., 1995, vol. 16:298-310.
Hong et. al., How is Embryo Size Genetically Regulated in Rice, Development, 1996, vol. 122:2051-2058.
National Center for Biotechnology Identifier No. 18652509, Oct. 5, 2005, R.A. Wing et. al., Rice Genomic Sequence.
B. Shuai et. al., The Lateral Organ Boundaries Gene Defines a Novel, Plant-Specific Gene Family, Plant Phys., 2002, vol. 129:747-761.
National Center for Biotechnology Identifier No. 18652508, Oct. 5, 2005, R.A. Wing et. al., Rice Genomic Sequence.
National Center for Biotechnology Identifier No. 17227164, Jun. 17, 2002, B. Shuai et. al., The Lateral Organ Boundaries Gene Defines a Novel, Plant-Specific Gene Family.

* cited by examiner

*Primary Examiner*—Stuart F. Baum

(57) ABSTRACT

Isolated nucleic acid fragments and recombinant constructs comprising such fragments useful for altering embryo/endosperm size during seed development are disclosed along with a method of controlling embryo/endosperm size during seed development in plants using such recombinant constructs.

7 Claims, 8 Drawing Sheets

Figure 1A

```
             10        20        30        40        50        60
    ATGAGCTCGTCGGTGGTTGTGAGCGCGAGCGGCCAGCGGCGGGCGGAGGAGGAGGAGGA  SEQ ID NO:25
    ATGAGCTCGTCGGTGGTTGTGAGCGCGAGCGGCCAGCGGCGGGCGGAGGAGGAGGAGGA  SEQ ID NO:28
    ATGAGCTCGTCGGTGGTTGTGAGCGCGAGCGGCCAGCGGCGGGCGGAGGAGGAGGAGGA  SEQ ID NO:30
    ATGAGCTCGTCGGTGGTTGTGAGCGCGAGCGGCCAGCGGCGGGCGGAGGAGGAGGAGGA  SEQ ID NO:32

70        80        90        100       110       120
    GGAGGTGGCGGCGC [C] GGAGGTGGAGGAGGAGGTGGGCCGTGCGGGGCGT [G] CAAGTTCTCTTG  SEQ ID NO:25
    GGAGGTGGCGGCGC  C  GGAGGTGGAGGAGGAGGTGGGCCGTGCGGGGCGT  G  CAAGTTCTCTTG  SEQ ID NO:28
    GGAGGTGGCGGCGC  C  GGAGGTGGAGGAGGAGGTGGGCCGTGCGGGGCGT  T  CAAGTTCTCTTG  SEQ ID NO:30
    GGAGGTGGCGGCGC  -  GGAGGTGGAGGAGGAGGTGGGCCGTGCGGGGCGT  G  CAAGTTCTCTTG  SEQ ID NO:32

130       140       150       160       170       180
    CGGCGGAAGTGCGTGCAGGGGTGCATCTTCGCGCCCTACTTCGACTCGGAGGCCGGGGCG  SEQ ID NO:25
    CGGCGGAAGTGCGTGCAGGGGTGCATCTTCGCGCCCTACTTCGACTCGGAGGCCGGGGCG  SEQ ID NO:28
    CGGCGGAAGTGCGTGCAGGGGTGCATCTTCGCGCCCTACTTCGACTCGGAGGCCGGGGCG  SEQ ID NO:30
    CGGCGGAAGTGCGTGCAGGGGTGCATCTTCGCGCCCTACTTCGACTCGGAGGCCGGGGCG  SEQ ID NO:32

190       200       210       220       230       240
    GCGCACTTCGCGGCGGTGTTCGGCGCCAGCAAGGTGTCCAAGCTGTCCAAGCTGCTGCAG  SEQ ID NO:25
    GCGCACTTCGCGGCGGTGTTCGGCGCCAGCAACGTGTCCAAGCTGTCCAAGCTGCTGCAG  SEQ ID NO:28
    GCGCACTTCGCGGCGGTGTTCGGCGCCAGCAACGTGTCCAAGCTGTCCAAGCTGCTGCAG  SEQ ID NO:30
    GCGCACTTCGCGGCGGTGTTCGGCGCCAGCAACGTGTCCAAGCTGTCCAAGCTGCTGCAG  SEQ ID NO:32
```

Figure 1B

```
                250       260       270       280       290       300
         ---------+---------+---------+---------+---------+---------+
241  CAGATCCCGGCGCGCACCGCGCCGCCTCGACGCCGTCGTCA C  CATCTGCTACGAGGCCCAGGCC  SEQ ID NO:25
241  CAGATCCCGGCGCGCACCGCGCCGCCTCGACGCCGTCGTCA C  CATCTGCTACGAGGCCCAGGCC  SEQ ID NO:28
241  CAGATCCCGGCGCGCACCGCGCCGCCTCGACGCCGTCGTCA T  CATCTGCTACGAGGCCCAGGCC  SEQ ID NO:30
240  CAGATCCCGGCGCGCACCGCGCCGCCTCGACGCCGTCGTCA C  CATCTGCTACGAGGCCCAGGCC  SEQ ID NO:32

310       320       330       340       350       360
         ---------+---------+---------+---------+---------+---------+
301  CGCCTCCGCGACCCCGTCTACGGCTGCGTCGCCACATCTTCCACCTTCCAACACCAGGTG  SEQ ID NO:25
301  CGCCTCCGCGACCCCGTCTACGGCTGCGTCGCCACATCTTCCACCTTCCAACACCAGGTG  SEQ ID NO:28
301  CGCCTCCGCGACCCCGTCTACGGCTGCGTCGCCACATCTTCCACCTTCCAACACCAGGTG  SEQ ID NO:30
300  CGCCTCCGCGACCCCGTCTACGGCTGCGTCGCCACATCTTCCACCTTCCAACACCAGGTG  SEQ ID NO:32

370       380       390       400       410       420
         ---------+---------+---------+---------+---------+---------+
361  GCAGGTCTCCAGTCCGAGCTGAACTACCTGCAAGGTCACCTCTGACGATGGAGCTGCCG  SEQ ID NO:25
361  GCAGGTCTCCAGTCCGAGCTGAACTACCTGCAAGGTCACCTCTGACGATGGAGCTGCCG  SEQ ID NO:28
361  GCAGGTCTCCAGTCCGAGCTGAACTACCTGCAAGGTCACCTCTGACGATGGAGCTGCCG  SEQ ID NO:30
360  GCAGGTCTCCAGTCCGAGCTGAACTACCTGCAAGGTCACCTCTGACGATGGAGCTGCCG  SEQ ID NO:32

430       440       450       460       470       480
         ---------+---------+---------+---------+---------+---------+
421  TCGCCGCCGCCTACGTCGCCGGGCCGACCCTGGCCGCGCCACAGCCACAGCCACTGATG  SEQ ID NO:25
421  TCGCCGCCGCCTACGTCGCCGGGCCGACCCTGGCCGCGCCACAGCCACAGCCACTGATG  SEQ ID NO:28
421  TCGCCGCCGCCTACGTCGCCGGGCCGACCCTGGCCGCGCCACAGCCACAGCCACTGATG  SEQ ID NO:30
420  TCGCCGCCGCCTACGTCGCCGGGCCGACCCTGGCCGCGCCACAGCCACAGCCACTGATG  SEQ ID NO:32
```

Figure 1C

```
              490        500        510        520        530        540
        ----------+----------+----------+----------+----------+----------+
    481 CCGATGACCGCCGCCGCCCGCGCCAACTTCAACTTCTCCGACCTGCCATCGTCGTCGGCGGCCAAC SEQ ID NO:25
    481 CCGATGACCGCCGCCGCCCGCGCCAACTTCAACTTCTCCGACCTGCCATCGTCGTCGGCGGCCAAC SEQ ID NO:28
    481 CCGATGACCGCCGCCGCCCGCGCCAACTTCAACTTCTCCGACCTGCCATCGTCGTCGGCGGCCAAC SEQ ID NO:30
    480 CCGATGACCGCCGCCGCCCGCGCCAACTTCAACTTCTCCGACCTGCCATCGTCGTCGGCGGCCAAC SEQ ID NO:32

550        560        570        580        590        600
        ----------+----------+----------+----------+----------+----------+
    541 ATTCCGGTCACCGCCGCCGACCTGTCCACCCTCTTTGACCCACTGCCGGCGGCGGCAGCCGCAG SEQ ID NO:25
    541 ATTCCGGTCACCGCCGCCGACCTGTCCACCCTCTTTGACCCACTGCCGGCGGCGGCAGCCGCAG SEQ ID NO:28
    541 ATTCCGGTCACCGCCGCCGACCTGTCCACCCTCTTTGACCCACTGCCGGCGGCGGCAGCCGCAG SEQ ID NO:30
    540 ATTCCGGTCACCGCCGCCGACCTGTCCACCCTCTTTGACCCACTGCCGGCGGCGGCAGCCGCAG SEQ ID NO:32

610        620        630        640        650        660
        ----------+----------+----------+----------+----------+----------+
    601 TGGGGACTATACCAGCAGCAGCAACAACCACCAGCAGCTGCATCATCACCCCTATGAC SEQ ID NO:25
    601 TGGGGACTATACCAGCAGCAGCAACAACCACCAGCAGCTGCATCATCACCCCTATGAC SEQ ID NO:28
    601 TGGGGACTATACCAGCAGCAGCAACAACCACCAGCAGCTGCATCATCACCCCTATGAC SEQ ID NO:30
    600 TGGGGACTATACCAGCAGCAGCAACAACCACCAGCAGCTGCATCATCACCCCTATGAC SEQ ID NO:32

670        680        690        700        710        720
        ----------+----------+----------+----------+----------+----------+
    661 CGGATGGGCGACGGCTCGTCGAGCAGCAGCAGCAGAGGCGGCGACGATGGCAGCGACGGCGGC SEQ ID NO:25
    661 CGGATGGGCGACGGCTCGTCGAGCAGCAGCAGCAGAGGCGGCGACGATGGCAGCGACGGCGGC SEQ ID NO:28
    661 CGGATGGGCGACGGCTCGTCGAGCAGCAGCAGCAGAGGCGGCGACGATGCAGCGACGGCGGC SEQ ID NO:30
    660 CGGATGGGCGACGGCTCGTCGAGCAGCAGCAGCAGAGGCGGCGACGATGGCAGCGACGGCGGC SEQ ID NO:32
```

Figure 1D

```
          730       740       750       760       770       780
          ----------+---------+---------+---------+---------+---------+
721 GACTTGCAAGCGCTGGCGAGGGAGCTTCTTGACCGCCATGGACGGTCGTCGTCGAGCTCC  SEQ ID NO:25
721 GACTTGCAAGCGCTGGCGAGGGAGCTTCTTGACCGCCATGGACGGTCGTCGTCGAGCTCC  SEQ ID NO:28
721 GACTTGCAAGCGCTGGCGAGGGAGCTTCTTGACCGCCATGGACGGTCGTCGTCGAGCTCC  SEQ ID NO:30
720 GACTTGCAAGCGCTGGCGAGGGAGCTTCTTGACCGCCATGGACGGTCGTCGTCGAGCTCC  SEQ ID NO:32

790       800       810
          ----------+---------+---------+
781 AAGCTGGAGCCGCCACCTCACACACAGTGA  SEQ ID NO:25
781 AAGCTGGAGCCGCCACCTCACACACAGTGA  SEQ ID NO:28
781 AAGCTGGAGCCGCCACCTCACACACAGTGA  SEQ ID NO:30
780 AAGCTGGAGCCGCCACCTCACACACAGTGA  SEQ ID NO:32
```

Figure 2

```
             10         20         30         40         50         60
     1  MSSSVVVSASGSGSGGGGGGGAGGGGGGGPCGA C KFLRRKCVQGCIFAPYFDSEAGA  SEQ ID NO:26
     1  MSSSVVVSASGSGSGGGGGGGAGGGGGGGPCGA C KFLRRKCVQGCIFAPYFDSEAGA  SEQ ID NO:29
     1  MSSSVVVSASGSGSGGGGGGGAGGGGGGGPCGA F KFLRRKCVQGCIFAPYFDSEAGA  SEQ ID NO:31

70         80         90        100        110        120
    61  AHFAAVHKVFGASNVSKLLQQIPAHRRLDAVV   ICYEAQARLRDPVYGCVAHIFHLQHQV  SEQ ID NO:26
    61  AHFAAVHKVFGASNVSKLLQQIPAHRRLDAVV T I ICYEAQARLRDPVYGCVAHIFHLQHQV  SEQ ID NO:29
    61  AHFAAVHKVFGASNVSKLLQQIPAHRRLDAVV T   ICYEAQARLRDPVYGCVAHIFHLQHQV  SEQ ID NO:31

130        140        150        160        170        180
   121  AGLQSELNYLQGHLSTMELPSPPPYVAGPTLAPPQPQPLMPMTAAANFNFSDLPSSSAAN  SEQ ID NO:26
   121  AGLQSELNYLQGHLSTMELPSPPPYVAGPTLAPPQPQPLMPMTAAANFNFSDLPSSSAAN  SEQ ID NO:29
   121  AGLQSELNYLQGHLSTMELPSPPPYVAGPTLAPPQPQPLMPMTAAANFNFSDLPSSSAAN  SEQ ID NO:31

190        200        210        220        230        240
   181  IPVTADLSTLFDPLPAAQPQWGLYQQQQHHHQQLHHHPYDRMGDGSSSSRGDDDGSDGG  SEQ ID NO:26
   181  IPVTADLSTLFDPLPAAQPQWGLYQQQQHHHQQLHHHPYDRMGDGSSSSRGDDDGSDGG  SEQ ID NO:29
   181  IPVTADLSTLFDPLPAAQPQWGLYQQQQHHHQQLHHHPYDRMGDGSSSSRGDDDDGSDGG  SEQ ID NO:31

250        260
   241  DLQALARELLDRHGRSSSSSKLEPPPHTQ                                 SEQ ID NO:26
   241  DLQALARELLDRHGRSSSSSKLEPPPHTQ                                 SEQ ID NO:29
   241  DLQALARELLDRHGRSSSSSKLEPPPHTQ                                 SEQ ID NO:31
```

Figure 3A

```
               10         20         30         40         50         60
                +----------+----------+----------+----------+----------+
  1 MSSSVVVSAS----GSGSGGGGGGGGGGAGGGGGG PCGACKFLRRKCVQGCIFAPYF DS SEQ ID NO:26
  1 MSSSVVVSAS----GSGSGGGGGGGGGGAGGGGGG PCGACKFLRRKCVQGCIFAPYF DS SEQ ID NO:27
  1 MSGGGNTITAVGGGGGGCGGGGGGSGGGGSGGGGGG PCGACKFLRRKCVPGCIFAPYF DS SEQ ID NO:54
  1 MSAGGGGGGTSTLGGGPSGSGSGSGPGGS--GGGG- PCGACKFLRRKCVSGCIFAPYF DS SEQ ID NO:37
  1 MANEG---------AAAAAAAAAAATGAGS     PCGACKFLRRRCVPECVFAPYF SS SEQ ID NO:39
  1 MSAGGGS----STLGGGPSGSSSGGPGGS--GGGGG PCGACKFLRRKCVSGCIFAPYF DS SEQ ID NO:41
  1 MASSG---------SGG------------GSPGS  PCGACKFLRRKCAAECVFAPHF CA SEQ ID NO:43
  1 MSSTVHPSSS----GSSGGAGGGGSGGS--GGGSG PCGACKFLRRKCVPGCIFAPYF DS SEQ ID NO:45
  1 -----------------------------       ---RXCVVGCIFAPYF DS SEQ ID NO:47
  1 MSSKA---------GNGSGSGSGSGGGS        PCGACKFLRRKCVAGCVFAPYF DS SEQ ID NO:49
  1 MAS-----------ASGNGVSNGSGS          PCGACKFLRRRCASDCIFAPYF CS SEQ ID NO:51
  1 MA--G---------AGV-----------TTTGS  PCGACKFLRRRCAAECVFAPYF CA SEQ ID NO:53
    *                                  *   ***  *   ***

70         80         90        100        110        119
                +----------+----------+----------+----------+----------+
 57 EAGAAH FAAVHKVFGASN VSKLLLQQIPAHRRLDAVVTICYEAQARL RDPVYGCVA HIFH SEQ ID NO:26
 57 EAGAAH FAAVHKVFGASN VSKLLLQQIPAHRRLDAVVTICYEAQARL RDPVYGCVA HIFH SEQ ID NO:27
 61 EQGSAY FAAVHKVFGASN VSKLLLHIPVHRRSDAVVTICYEAQARI RDPIYGCVA HIFA SEQ ID NO:54
 58 EQGAAH FAAVHKVFGASN VSKLLLQIPAHKRLDAVVTICYEAQARL RDPVYGCVA HIFA SEQ ID NO:37
 48 DQGAAR FAAIHKVFGASN ASKLLSHLPVADRCEAVVTTYEAQARL RDPVYGCVA QIFA SEQ ID NO:39
 56 EQGAAH FAAVHKVFGASN VSKLLLQIPAHKRLDAVVTICYEAQARL RDPVYGCVA HIFA SEQ ID NO:41
 38 EDGAAQ FAAIHKVFGASN AAKLLQQVAPADRSEAAATVTYEAQARL RDPIYGCVA HIFA SEQ ID NO:43
 54 EQGAAH FAAVHKVFGASN VSKLLLHIPVHKRLDAVVTICYEAQARL RDPVYGCVA HIFA SEQ ID NO:45
 16 EQGATH FAAVHKVFGASN VSKLLLHIPVHKRLDAVVTICYEAQARL RDPVYGCVA NIFA SEQ ID NO:47
 44 EQGATH FAAVHKVFGASN VSKLLNLPLNKRLDAVITICYEAQSRI RDPVFGCVA HIFA SEQ ID NO:49
 40 EQGPAR FAAIHKVFGASN VSKLLLHIPAHDRCEAVVTITYEAQARI RDPVYGCVS HIFA SEQ ID NO:51
 36 EDGASQ FAAIHKVFGASN AAKLLQQVAPGDRSEAAATVTYEAQARL RDPVYGCVA HIFA SEQ ID NO:53
    *  *   *** ******   ***          *       ****** **** ****  ***
```

Figure 3B

```
      120        130        140        150        160        170        180
       +----------+----------+----------+----------+----------+----------+
116 LQHQVAGLQSELNYLQGHL STMELPSPPPYVAGPTLAPPQPQPLMPMTAAANFNFSDLPSS    SEQ ID NO:26
116 LQHQVAGLQSELNYLQGHL STMELPSPPPYVAGPTLAPPQPQPLMPMTAAANFNFSDLPSS    SEQ ID NO:27
120 LQQQVVNLQAEVSYLQAHL ASLELPQPQT----RPQPMPQPQPLF-FTPPPLAITDLPAS     SEQ ID NO:54
117 LQQQVVNLQAELTYLQAHL ATLELPAPPP---LPAP---PQ-MP-M--PGPFSISDLPLS     SEQ ID NO:37
107 LQQQVAILQAQLMQAKAQL A-----CGVQGAAAHSPASHHHQWPDSASISALLRQDAACS     SEQ ID NO:39
115 LQQQVVNLQAELTYLQAHL ATLELPAPPP---LPAP---PQ-MP-M--PGPFSISDLPLS     SEQ ID NO:41
97  LQQQVASLQMQVLQAKAQV A-----QTMAAAGPQG------------GSSPLLQR----     SEQ ID NO:43
113 LQQQVVNLQAELTYLQAHL ATLELPSPPP----PPLP---PQTLL-T--PPPLSISDLPSS    SEQ ID NO:45
75  LQQQVGNLQAELSYLQTYL ASLGASNSTX----KLRQ---HQCLL-------------     SEQ ID NO:47
103 LQQQVVSLQTEVSYLQSHL AAMELPQPPP----PPPPQE--TVVQAPVFSIADIPAA         SEQ ID NO:49
99  LQQQVARLQAQLMQVKAQL T-----QNL--VESRNIENNHHLQGNNNNVTGQLMNHPFCPP    SEQ ID NO:51
95  LQQQVALQAQVAHARTQ-  -----------AQLGAAT---------AMHPLLQQQLQQQ     SEQ ID NO:53
    **  **   *
    *  *

190        200        210        220        230        240
       +----------+----------+----------+----------+----------+
177 SAANIPVTADLSTLFDPLPAAQPQWGLYQQQQHHHQQLHHH--------PYDRMGDGSSS    SEQ ID NO:26
177 SAANIPVTADLSTLFDPLPAAQPQWGLYQQQQHHHQQLHHH--------PYDRMGDGSSS    SEQ ID NO:27
176 -VSPLPSTYDLASIFDQ-TTSSSAWATQQ--------RRFIDPR-HQYGVSSS--SS        SEQ ID NO:54
167 --TSVPTTVDLSALFDP-PPPQ--WATAQQPHHHHQQPPQHHQLRQP-APYGAGASVR-    SEQ ID NO:37
163 ARRPGGPLDDFFT--PELVAG-FRDDVAAAAGQH----CAGKVDAGELQ-YL------    SEQ ID NO:39
165 --TSVPTTVDLSALFDP-PPPQ--WATAQQPHHHHQQPPQHHQLRQP-APYGAGASVRPG   SEQ ID NO:41
135 -WPL-------EP--ESLSTQ--SSGCYS-----------------DM-YC-------    SEQ ID NO:43
164 --SSAPGSYDLQSLFDP-MAQNS-WSM-------------QQRLIDPR-HQFIGSTS---G   SEQ ID NO:45
113 ------------------------------------------QQHL-SPK-ANF----    SEQ ID NO:47
154 TVAGMPASYDLSSLFEP-TGQQNSWGGGIDPRQFLAVGPSSTTDADLQAMARDLSERLA     SEQ ID NO:49
153 YMNPISPQSSL---ESIDHSSINDGMSMQDIQS----REDFQIQAKERPYN-------    SEQ ID NO:51
133 AWQVAAAADQHDH--QSMTSTQSSSGCYSGAHQR---SDGSSLHGAEM-YC-------    SEQ ID NO:53
```

Figure 3C

```
         250          260          270          280
          |            |            |            |
229  SRGGDDDGSDGGDLQALARELLDRHG----------RSSSSSKLEPPPHTQ    SEQ ID NO:26
229  SRGGDDDGSDGGDLQALARELLDRHG----------RSSSSSKLEPPPHTQ    SEQ ID NO:27
220  SVAVGLGGENSHDLQALAHELLHRQGSP-------PPAATDHSPSRTMSR     SEQ ID NO:54
219  ----------------------------------SGGVKLEHPPPHSR      SEQ ID NO:37
207  ------AQAMMRSPNYSL                                    SEQ ID NO:39
219  GGPGMAESSGGDELQSLARELLDRH---------RSGGVKLEHPPPHSR     SEQ ID NO:41
156  ------GFGDQEEGSYTR                                    SEQ ID NO:43
204  SSSLTTTGSGSGDLHTLARELLHRHGSPSHGSMPCSGALSSSPSSISK      SEQ ID NO:45
123  ---------------------------------PSSF-H               SEQ ID NO:47
213  SLPPPAPAPAFAPLPPLP-------PAPAPAPSCPNAPSSLSLS          SEQ ID NO:49
197  ------NNDLGELQELALRMMR----------------N               SEQ ID NO:51
178  ------GYGEQEEGSY                                      SEQ ID NO:53
```

ALTERATION OF PLANT EMBRYO/ENDOSPERM SIZE DURING DEVELOPMENT

This application claims the benefit of U.S. Provisional Application No. 60/664,512, filed 23 Mar. 2005, the entire content of which is hereby incorporated by reference.

FIELD OF THE INVENTION

The present invention is in the field of plant breeding and genetics and, in particular, relates to recombinant constructs useful for altering embryo/endosperm size during seed development.

BACKGROUND OF THE INVENTION

Elucidation of how the size of a developing embryo is genetically regulated is important because the final volume of endosperm as a storage organ of starch and proteins is affected by embryo size in cereal crops. Researchers have found that genes involved in embryo size contribute to the regulation of endosperm development. Investigation of these genes is important for agriculture because cereal endosperms are the staple diet in many countries.

Rice mutants, having normally differentiated shoot and radicle and either reduced or enlarged embryo when compared to wild type rice, were identified in the early 1990s in plants obtained from methyl-nitrosourea mutagenized Taichung 65 cultivar. Mutant plants displaying an enlarged embryo were designated giant embryo (ge) mutants while plants displaying a smaller embryo were designated reduced embryo (re) mutants (Kitano et al. 1993, *Plant J.* 3:607-610; Hong et al. in 1995, *Dev. Genet.* 16:298-310).

The phenotypes of each of the three reduced embryo mutants were designated re1, re2, and re3 even though the gene(s) responsible for these phenotypes have not been characterized. A mutation in a different locus is responsible for the mutant phenotype. Phenotypic analysis of ge and re mutant plants led to the theory that embryo size may be determined by the interaction between embryo-specific genes and endosperm-specific genes regulating endosperm development (Hong et al. (1996) *Development* 122:2051-2058).

The reduced embryo size phenotype of re2 mutant plants is associated with the enlargement of the endosperm size without altering the overall seed size. This phenotype is potentially useful for improving cereal quality by increasing the amount of endosperm tissue, which is rich in starch and other nutrients. Moreover, the reduction of embryo size in seed has a potential benefit for some milling processes, where embryonic tissues are considered as waste, such as in the production of ethanol.

SUMMARY OF THE INVENTION

In a first embodiment, the invention concerns an isolated polynucleotide comprising:
 (a) a nucleic acid sequence encoding a polypeptide involved in altering embryo/endosperm size during seed development, said polypeptide having at least 80% amino acid sequence identity, based on the Clustal V method of alignment, when compared to an amino acid sequence selected from the group consisting of SEQ ID NOS:37, 39, 41, 43, 45, 47, 49, 51, and 53; or
 (b) a nucleic acid sequence set forth in SEQ ID NO:25 wherein said sequence comprises at least one of the following modifications:
  (i) nucleotide 278 is a T residue instead of a C;
  (ii) nucleotide 110 is a T residue instead of a G; or
  (iii) nucleotide 75 is deleted; or
 (c) a nucleic acid sequence set forth in SEQ ID NO:34 wherein
  (i) nucleotides 4473 through 4829 correspond to a first exon, and
  (ii) nucleotides 5661 through 6110 correspond to a second exon, and
  further wherein the nucleotides of (c) (i) and/or (c)(ii) encode a polypeptide involved in altering embryo/endosperm size during seed development,
 (d) a nucleic acid sequence set forth in SEQ ID NO:34 or 72; or
 (e) the full complement of (a), (b), (c), (d), or SEQ ID NO:34; or
 (f) all or part of a non-coding or coding region of the isolated polynucleotide comprising sequences of (a), (b) or SEQ ID NO:34 for use in co-suppression or antisense suppression of endogenous nucleic acid sequences encoding polypeptides involved in altering embryo/endosperm size during seed development.

In a second embodiment, the invention concerns a recombinant DNA construct comprising the isolated polynucleotide of the invention operably linked to at least one regulatory sequence.

In a third embodiment, the invention concerns a plant comprising in its genome the recombinant DNA construct of the invention as well as any seeds obtained from such a plant and oil obtained from such seeds. Also of interest are transformed plant tissue or plant cells comprising the recombinant DNA construct of the invention.

In a fourth embodiment, the invention concerns a method of altering embryo/endosperm size during seed development in a plant comprising:
 (a) transforming plant cells or plant tissue with the recombinant DNA construct of the invention;
 (b) regenerating transgenic plants from the transformed plant cells or plant tissue of (a);
 (c) screening the transgenic plants of (b) for seeds having an altered embryo/endosperm size based on a comparison of embryo/endosperm size of seeds obtained from non-transformed plants.

In a fifth embodiment, the invention concerns a method of mapping genetic variations related to controlling embryo/endosperm size and/or altering oil phenotype in plants comprising:
 (a) crossing two plant varieties; and
 (b) evaluating genetic variations with respect to
  (i) a nucleic acid sequence selected from the group consisting of SEQ ID NOS:25, 28, 30, 32, 34, 36, 38, 40, 42, 44, 46, 48, 50, 52, and 72; or
  (ii) a nucleic acid sequence encoding a polypeptide selected from the group consisting of SEQ ID NOS: 26, 29, 31, 33, 37, 39, 41, 43, 45, 47, 49, 51, and 53; in progeny plants resulting from the cross of step (a) wherein the evaluation is made using a method selected from the group consisting of RFLP (restriction fragment length polymorphism) analysis, SNP (single nucleotide polymorphism) analysis, and PCR-based analysis.

In a sixth embodiment the invention concerns a method of molecular breeding to control embryo/endosperm size and/or altering oil phenotype in plants comprising:
 (a) crossing two plant varieties; and
 (b) evaluating genetic variations with respect to (i) a nucleic acid sequence selected from the group consisting of SEQ ID NOS:25, 28, 30, 32, 34, 36, 38, 40, 42, 44, 46, 48, 50, 52, and 72; or (ii) a nucleic acid sequence encoding a polypeptide selected from the group consisting of SEQ ID NOS: 26, 29, 31, 33, 37, 39, 41, 43, 45, 47, 49, 51, and 53;

in progeny plants resulting from the cross of step (a) wherein the evaluation is made using a method selected from the group consisting of RFLP analysis, SNP analysis, and PCR-based analysis.

BRIEF DESCRIPTION OF THE FIGURES AND SEQUENCE LISTINGS

The invention can be more fully understood from the following detailed description and the accompanying drawings and Sequence Listing that form a part of this application.

FIG. 1A-D shows an alignment of the nucleotide sequences obtained for wild type RE2 (SEQ ID NO:25), and mutants re2-1 (SEQ ID NO:28), re2-2 (SEQ ID NO:30), and re2-3 (SEQ ID NO:32). Changes in the nucleotide sequence are indicated by a star below the alignment and by a box around the nucleotides at that position. Numbers at the left of the alignment indicate the nucleotide position.

FIG. 2 shows an alignment of the amino acid sequences obtained for polypeptides from wild type RE2 protein (SEQ ID NO:26), and re2-1 mutant protein (SEQ ID NO:29), and re2-2 mutant protein (SEQ ID NO:31). Changes in the amino acid sequence are indicated by a star below the alignment and by a box around the amino acids at that position. As seen in FIG. 2, mutant allele re2-1 had an isoleucine at amino acid 93 instead of the highly conserved threonine; mutant allele re2-2 had a phenylalanine instead of the conserved cysteine at amino acid 37. The deletion of a nucleotide at position 75 in mutant allele re2-3 gene produced a frame shift that results in a 127 amino acid polypeptide for the re2-3 mutant protein (set forth in SEQ ID NO:33) that is quite different than the one encoded by wild type RE2 gene or mutant genes re2-1 or re2-2. Numbers at the left of the alignment indicate the amino acid position.

FIG. 3A-C depicts the Clustal V alignment obtained for the amino acid sequences from the rice wild type RE2 protein (SEQ ID NO:26), the *O. sativa* protein having NCBI General Identifier No. 18652509 (SEQ ID NO:27), the *A. thaliana* LOB domain 18 protein having NCBI General Identifier No. 17227164 (SEQ ID NO:54), and the amino acid sequences of the polypeptides encoded by corn clones cef1f.pk001.f4:fis (SEQ ID NO:37), cpf1c.pk006.d18a:fis (SEQ ID NO:39), cpi1c.pk005.a12:fis (SEQ ID NO:41), and cr1n.pk0028.h3a:fis (SEQ ID NO:43), *Euphorbia lagascae* clone eel1c.pk003.b10:fis (SEQ ID NO:45), columbine clone eav1c.pk003.c9 (SEQ ID NO:47), guar clone lds3c.pk011.j11:fis (SEQ ID NO:49), soybean clone sdr1f.pk005.d21.f:fis (SEQ ID NO:51), and wheat clone wdr1f.pk002.110:fis (SEQ ID NO:53). The program uses dashes to maximize the alignment. An asterisk (*) below the alignment indicates amino acids conserved among all the sequences. The C-block, a GAS-block, and a leucine zipper conserved motifs are shown boxed. Numbers at the left of the alignment indicate the amino acid position.

The following sequence descriptions and sequence listings attached hereto comply with the rules governing nucleotide and/or amino acid sequence disclosures in patent applications as set forth in 37 C.F.R. §1.821-1.825.

SEQ ID NO:1 is the nucleotide sequence of oligonucleotide primer C10 6-3 used to amplify CAPS marker C10 7.7 to identify the re2 locus.

SEQ ID NO:2 is the nucleotide sequence of oligonucleotide primer C10 6-4 used to amplify CAPS marker C10 7.7 to identify the re2 locus.

SEQ ID NO:3 is the nucleotide sequence of oligonucleotide primer C10 15.9-1 used to amplify CAPS marker C10 15.9 to identify the re2 locus.

SEQ ID NO:4 is the nucleotide sequence of oligonucleotide primer C10 15.9-2 used to amplify CAPS marker C10 15.9 to identify the re2 locus.

SEQ ID NO:5 is the nucleotide sequence of oligonucleotide primer C10-7.7 2 HPYIVF used to amplify CAPS marker C10 7.7 Hpy.

SEQ ID NO:6 is the nucleotide sequence of oligonucleotide primer C10-7.7 2 HPYIVR used to amplify CAPS marker C10 7.7 Hpy.

SEQ ID NO:7 is the nucleotide sequence of oligonucleotide primer 11.5 HpyV used to amplify CAPS marker C10 11.5.

SEQ ID NO:8 is the nucleotide sequence of oligonucleotide primer C10 11.5-9 used to amplify CAPS marker C10 11.5.

SEQ ID NO:9 is the nucleotide sequence of oligonucleotide primer C10 11-5 used to amplify CAPS marker C10 11.0.

SEQ ID NO:10 is the nucleotide sequence of oligonucleotide primer 11 HinfR used to amplify CAPS marker C10 11.0.

SEQ ID NO:11 is the nucleotide sequence of oligonucleotide primer 9.6 DraIF used to amplify CAPS marker C10 9.6.

SEQ ID NO:12 is the nucleotide sequence of oligonucleotide primer 9.6 DraIR used to amplify CAPS marker C10 9.6.

SEQ ID NO:13 is the nucleotide sequence of the oligonucleotide primer E08 93KF used to amplify CAPS marker E08 93K.

SEQ ID NO:14 is the nucleotide sequence of the oligonucleotide primer E08 93KR used to amplify CAPS marker E08 93K.

SEQ ID NO:15 is the nucleotide sequence of the oligonucleotide primer E08 46KF used to amplify CAPS marker E08 46K.

SEQ ID NO:16 is the nucleotide sequence of the oligonucleotide primer E08 46KR used to amplify CAPS marker E08 46K.

SEQ ID NO:17 is the nucleotide sequence of the oligonucleotide primer K08 21KF used to amplify CAPS marker K08 21K.

SEQ ID NO:18 is the nucleotide sequence of the oligonucleotide primer K08 21KR used to amplify CAPS marker K08 21K.

SEQ ID NO:19 is the nucleotide sequence of the oligonucleotide primer K08 46KF used to amplify SNP-based marker K08 46K.

SEQ ID NO:20 is the nucleotide sequence of the oligonucleotide primer K08 46KR used to amplify SNP-based marker K08 46K.

SEQ ID NO:21 is the nucleotide sequence of the oligonucleotide primer LOB-82F used to amplify the first exon (exon 1) of RE2 wild type gene or re2 mutant gene from genomic DNA.

SEQ ID NO:22 is the nucleotide sequence of the oligonucleotide primer LOB R1 used to amplify the first exon (exon 1) of RE2 wild type gene or re2 mutant gene from genomic DNA.

SEQ ID NO:23 is the nucleotide sequence of the oligonucleotide primer LOB F2 used to amplify the second exon (exon 2) of RE2 wild type gene or re2 mutant gene from genomic DNA.

SEQ ID NO:24 is the nucleotide sequence of the oligonucleotide primer LOB R2 used to amplify the second exon (exon 2) of RE2 wild type gene or re2 mutant gene from genomic DNA.

SEQ ID NO:25 is the nucleotide sequence of the wild-type rice RE2 gene open reading frame (ORF) identified in the instant application.

SEQ ID NO:26 is the amino acid sequence of the wild-type rice RE2 protein derived from translating nucleotides 1 through 807 of SEQ ID NO:25.

SEQ ID NO:27 is the amino acid sequence of the rice protein of unknown function found in the NCBI database as Version AAL77143.1 having NCBI General Identifier No. 18652509.

SEQ ID NO:28 is the nucleotide sequence obtained for mutant allele re2-1 gene.

SEQ ID NO:29 is the amino acid sequence of a re2-1 mutant allele protein obtained by translating nucleotides 1 through 807 of SEQ ID NO:28.

SEQ ID NO:30 is the nucleotide sequence obtained for mutant allele re2-2 gene.

SEQ ID NO:31 is the amino acid sequence of a re2-2 mutant allele protein obtained by translating nucleotides 1 through 807 of SEQ ID NO:30.

SEQ ID NO:32 is the nucleotide sequence obtained for mutant allele re2-3 gene.

SEQ ID NO:33 is the amino acid sequence of a re2-3 mutant allele protein obtained by translating nucleotides 1 through 378 of SEQ ID NO:32.

SEQ ID NO:34 is the nucleotide sequence of the approximately 9 Kb BamH I fragment from RE2G4 which comprises the RE2 wild type gene coding region. Nucleotides 1 through 4472 are 5' of the ATG initiation codon, nucleotides 4473 through 4829 correspond to the first exon, nucleotides 4830 through 5660 correspond to an intron, and nucleotides 5661 through 6110 correspond to the second exon. Nucleotides 6111 through 6113 form a termination codon.

SEQ ID NO:35 is the nucleotide sequence of vector pML18 used to subclone the approximately 9 Kb BamH I fragment from RE2G4 comprising the rice RE2 wild type gene coding region.

SEQ ID NO:36 is the nucleotide sequence comprising the entire cDNA insert in clone cef1f.pk001.f4:fis encoding a putative corn RE2 protein homolog.

SEQ ID NO:37 is the deduced amino acid sequence of a putative corn RE2 protein homolog derived from nucleotides 76 through 851 of SEQ ID NO:36.

SEQ ID NO:38 is the nucleotide sequence comprising the entire cDNA insert in clone cpf1c.pk006.d18a:fis encoding a putative corn RE2 protein homolog.

SEQ ID NO:39 is the deduced amino acid sequence of a putative corn RE2 protein homolog derived from nucleotides 151 through 804 of SEQ ID NO:38.

SEQ ID NO:40 is the nucleotide sequence comprising the entire cDNA insert in clone cpi1c.pk005.a12:fis encoding a putative corn RE2 protein homolog.

SEQ ID NO:41 is the deduced amino acid sequence of a putative corn RE2 protein homolog derived from nucleotides 81 through 854 of SEQ ID NO:40.

SEQ ID NO:42 is the nucleotide sequence comprising the entire cDNA insert in clone cr1n.pk0028.h3a:fis encoding a putative corn RE2 protein homolog.

SEQ ID NO:43 is the deduced amino acid sequence of a putative corn RE2 protein homolog derived from nucleotides 158 through 658 of SEQ ID NO:42.

SEQ ID NO:44 is the nucleotide sequence comprising the entire cDNA insert in clone eel1c.pk003.b10:fis encoding a putative *Euphorbia* RE2 protein homolog.

SEQ ID NO:45 is the deduced amino acid sequence of a putative *Euphorbia* RE2 protein homolog derived from nucleotides 71 through 823 of SEQ ID NO:44.

SEQ ID NO:46 is the nucleotide sequence comprising a portion of the cDNA insert in clone eav1c.pk003.c9 encoding a fragment of a putative columbine RE2 protein homolog.

SEQ ID NO:47 is the deduced amino acid sequence of a fragment of a putative columbine RE2 protein homolog derived from nucleotides 2 through 382 of SEQ ID NO:46.

SEQ ID NO:48 is the nucleotide sequence comprising the entire cDNA insert in clone lds3c.pk011.j11:fis encoding a putative guar RE2 protein homolog.

SEQ ID NO:49 is the deduced amino acid sequence of a putative guar RE2 protein homolog derived from nucleotides 146 through 898 of SEQ ID NO:48.

SEQ ID NO:50 is the nucleotide sequence comprising the entire cDNA insert in clone sdr1f.pk005.d21.f:fis encoding putative soybean RE2 protein homolog.

SEQ ID NO:51 is the deduced amino acid sequence of a putative soybean RE2 protein homolog derived from nucleotides 971 through 1609 of SEQ ID NO:50.

SEQ ID NO:52 is the nucleotide sequence comprising the entire cDNA insert in clone wdr1f.pk002.110:fis encoding a putative wheat RE2 protein homolog.

SEQ ID NO:53 is the deduced amino acid sequence of a putative wheat RE2 protein homolog derived from nucleotides 80 through 640 of SEQ ID NO:52.

SEQ ID NO:54 is the amino acid sequence of the *Arabidopsis thaliana* LOB domain 18 protein having NCBI General Identifier No. 17227164.

SEQ ID NO:55 is the consensus amino acid sequence included in the C block of RE2 protein homologs.

SEQ ID NO:56 is the amino acid sequence of the motif at the N-terminus of the 49 amino acid GAS block of RE2 protein homologs.

SEQ ID NO:57 is the amino acid sequence of the motif at the C-terminus of the 49 amino acid GAS block of RE2 protein homologs.

SEQ ID NO:58 is the amino acid sequence of the Leucine-zipper motif of RE2 protein homologs.

SEQ ID NO:59 is the nucleotide sequence of oligonucleotide primer Cpi BbsI F used to amplify genomic *Zea mays* RE2 gene.

SEQ ID NO:60 is the nucleotide sequence of oligonucleotide primer Cpi Bbsl R used to amplify genomic *Zea mays* RE2 gene.

SEQ ID NO:61 is the nucleotide sequence of the genomic fragment encoding a maize RE2 protein homolog obtained by amplifying a maize genomic library with primers Cpi Bbsl F and Cpi Bbsl R. Nucleotides 79 through 429 correspond to the first exon, nucleotides 430 through 1363 correspond to an intron, and nucleotides 1364 through 1783 correspond to the second exon.

SEQ ID NO:62 is the nucleotide sequence of oligonucleotide primer RE2 pro Bst 2F used for amplifying a portion of the 5' region of the OsRE2 gene.

SEQ ID NO:63 is the nucleotide sequence of oligonucleotide primer RE2 PRO R Bbsl used for amplifying a portion of the 5' region of the OsRE2 gene.

SEQ ID NO:64 is the nucleotide sequence of plasmid RE2Pro comprising a portion of the OsRE2 gene promoter region.

SEQ ID NO:65 is the nucleotide sequence of oligonucleotide primer RE2 TERM XbaI R used for amplifying a 780 bp fragment of the 3' terminator region from the OsRE2 gene.

SEQ ID NO:66 is the nucleotide sequence of oligonucleotide primer RE2 TERM EcoBspml used for amplifying a 780 bp fragment of the 3' terminator region from the OsRE2 gene.

SEQ ID NO:67 is the nucleotide sequence of plasmid RE2TERGEM comprising a portion of the OsRE2 gene terminator region.

SEQ ID NO:68 is the nucleotide sequence of an oligonucleotide primer that may be used to identify RE2 homologs from other plant species.

SEQ ID NO:69 is the nucleotide sequence of an oligonucleotide primer that may be used to identify RE2 homologs from other species.

SEQ ID NO:70 is the nucleotide sequence of an oligonucleotide primer that may be used to identify RE2 homologs from other plant species.

SEQ ID NO:71 is the nucleotide sequence of the "RE2 second exon probe" used to screen for cDNAs encoding RE2 proteins.

SEQ ID NO:72 is the nucleotide sequence of clone RE2 cDNA C1, the longest cDNA clone identified encoding an RE2 protein.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

Disclosure of all references, patents, and patent applications cited herein are hereby incorporated by reference.

The terms "isolated nucleic acid fragment" and "isolated polynucleotide" are used interchangeably herein. These terms refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

It has been reported that the Lateral Organ Boundary (LOB) gene in *Arabidopsis* has a potential role in lateral organ development. See Shuai et al., (2002), Plant Phys. 129, 747-761. Shuai et al. found LOB gene expression at the base of lateral organs in the shoots and roots of *Arabidopsis*. In fact, 23 members of the LOB domain family (LBD) of genes were found to exhibit expression patterns in the root tissues of *Arabidopsis*.

The LOB domain 18 protein is considered as being in the class I group of the Lateral Organ Boundaries (LOB) domain protein plant-specific gene family. The Class I LOB domain proteins contain a C-block, a GAS-block, and a leucine zipper motif (Shuai, B. et al., 2002, *Plant Phys.* 129:747-761). Thus, it is expected that an *Oryza sativa* RE2 protein and its homologs would also contain a C-block, a GAS-block, and a leucine zipper motif. The consensus sequences of these motifs were identified using a Clustal V alignment and are indicated in FIG. 3.

FIG. 3A-C depicts the Clustal V alignment obtained for the amino acid sequences from the rice wild type RE2 protein (SEQ ID NO:26), the *O. sativa* protein having NCBI General Identifier No. 18652509 (SEQ ID NO:27), the *A. thaliana* LOB domain 18 protein having NCBI General Identifier No. 17227164 (SEQ ID NO:54), and the amino acid sequences of the polypeptides encoded by corn clones cef1f.pk001.f4:fis (SEQ ID NO:37), cpf1c.pk006.d18a:fis (SEQ ID NO:39), cpi1c.pk005.a12:fis (SEQ ID NO:41), and cr1n.pk0028.h3a:fis (SEQ ID NO:43), *Euphorbia lagascae* clone eel1c.pk003.b10:fis (SEQ ID NO:45), columbine clone eav1c.pk003.c9 (SEQ ID NO:47), guar clone lds3c.pk011.j11:fis (SEQ ID NO:49), soybean clone sdr1f.pk005.d21.f:fis (SEQ ID NO:51), and wheat clone wdr1f.pk002.110:fis (SEQ ID NO:53). The program uses dashes to maximize the alignment. An asterisk (*) below the alignment indicates amino acids conserved among all the sequences. The C-block, a GAS-block, and a leucine zipper conserved motifs are shown boxed.

It has been found in the present invention that a single mutation of a rice gene encoding a member of a class I LOB domain protein family can lead to alteration of embryo/endosperm size during seed development.

The gene associated with the reduced embryo phenotype is named Reduced Embryo2 (RE2). Silencing or inhibition of this gene leads to a reduction of embryonic tissue, thus, resulting in a smaller embryo size and a concomitantly larger endosperm size. Reduction of embryo size will result in seeds having a reduced amount of components such as oils. On the other hand, overexpression of this gene might lead to an increase of embryonic tissue, thus, resulting in a larger embryo size and a concomitantly smaller endosperm size.

The italicized and uppercase term "RE2" as used herein refers to a genetic locus capable of expressing a Reduced Embryo 2 protein. The italicized and lowercase letters term "re2" as used herein refers to a mutated form of RE2. Italics are not used when referring to a protein or polypeptide encoded by the genetic locus. Thus, the uppercase term "RE2" as used herein refers to the wild type protein, and the lowercase "re2" as used herein refers to a mutant protein. As was noted above, the rice RE2 isolated polynucleotide was identified in the instant application using high fidelity mapping of DNA obtained from reduced embryo 2 (re2) mutant plants. These mutant plants produce grain that have a small embryo phenotype.

The terms "*Oryza sativa* RE2", "OsRE2", and "rice RE2" are used interchangeably herein. These terms refer to a polynucleotide isolated from wild-type rice and whose sequence is set forth in the instant application. The rice RE2 isolated polynucleotide is the polynucleotide that, when mutated, is responsible for a reduced embryo 2, or re2, phenotype as exemplified by Hong et al. (1996, *Development* 122:2051-2058). Mutant rice displaying the re2 phenotype has a reduced embryo size and an enlarged endosperm size.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

A "homolog" can be a second gene in the same plant type or in a different plant type that has a polynucleotide sequence that is functionally identical to a sequence in the first gene. It is believed that, in general, homologs share a common evolutionary past.

The term "RE2 homolog" refers to an isolated polynucleotide encoding a class I LOB domain polypeptide obtained from a plant species, other than rice, that functions in a manner similar to that of the rice RE2 isolated polynucleotide and that, when mutated, exhibits a reduced embryo phenotype. The corn, *Euphorbia lagascae*, Columbine, guar, soybean, and wheat isolated polynucleotides disclosed herein appear to encode such polypeptides, namely, these polypeptides are members of a class I LOB domain protein family, have a C-like motif, a GAS-like motif, and a leucine zipper-like motif, and are useful for altering embryo/endosperm size during seed development.

A search of GenBank and Du Pont proprietary databases using the rice RE2 gene sequence or the RE2 polypeptide sequence uncovered a number of isolated polynucleotides from plants that appeared to be homologous. RE2 homologs appear to encompass those polynucleotides isolated from plants, other than rice, which appeared to encode a polypeptide that shares sequence and/or functional similarity to the polypeptide encoded by the rice RE2 isolated polynucleotide. It is believed that such a polynucleotide would comprise a subset of the polynucleotides encoding polypeptides of the class I LOB domain family, and that alteration in the expression of this polypeptide may affect embryo/endosperm size.

"Sequence identity" or "identity" in the context of nucleic acid or polypeptide sequences refers to the nucleic acid bases or amino acid residues in the two sequences that are the same when aligned for maximum correspondence over a specified comparison window.

Thus, "Percentage of sequence identity" refers to the valued determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 55% to 100%. These identities can be determined using any of the programs described herein.

Sequence alignments and percent identity or similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other plant species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50%-100% may be useful in describing the present invention. Also, of interest is any full or partial complement of this isolated nucleotide fragment.

It is believed that another way to identify genes that are homologous to the rice RE2 gene is to screen by hybridization. It is possible to hybridize cDNA at 60° C. with a probe derived from the rice RE2 gene and wash at medium stringency conditions (5×SSPE, 0.5% SDS at 65° C. followed by 1×SSPE, 0.5×SDS at 65° C.). For general hybridization protocols, see Ausubel et al. 1993, "Current Protocols in Molecular Biology" John Wiley & Sons, USA, or Sambrook et al. 1989. Molecular Cloning: A Laboratory Manual. Cold Spring Harbor Laboratory Press. An appropriate probe with a unique sequence can be extracted, for example, from part of the exon 1 of the RE2 gene. Exon 1 of the RE2 gene has regions of sequence identity between the corn and rice RE2 nucleotide sequences. Oligonucleotide primers useful in hybridization screenings may have the sequences disclosed in SEQ ID NO: 68, SEQ ID NO:69, or SEQ ID NO:70, for example. The oligonucleotide primers having the sequences set forth in SEQ ID NO: 68, SEQ ID NO:69, or SEQ ID NO:70 have the sequences set forth as follows:

```
                                              SEQ ID NO:68
5'-GCATCTTCGCGCCCTACTTCGACTCGG-3'

SEQ ID NO:69
5'-GCACAAGGTGTTCGGCGCCAGCAACGTGTCCAAGC-3'

EQ ID NO:70
5'-CCGCGACCCCGTCTACGGCTGCGTCGCCCACCTC-3'
```

Genomic DNA or cDNA clones giving significant signals may be isolated and their chromosomal origin analyzed using CAPS markers or SNP-based markers similar to those described in the present Application. DNA fragments containing the region homologous to rice RE2 gene may be further subcloned and sequenced. Polypeptides encoded by these polynucleotides should the have the C-Block, GAS Block N-end and C-end, and Leu Zipper consensus sequences described in Example 6 and as set forth in SEQ ID NOS:55 through 58.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. A "foreign" gene refers to a gene not normally found in the host organism, but that is introduced into the host organism by gene transfer. Foreign genes can comprise native genes inserted into a non-native organism, or recombinant DNA constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters which cause an isolated nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) Biochemistry of Plants 15:1-82. It is further recognized that since in most cases the exact boundaries of regulatory sequences have not been completely defined, DNA fragments of some variation may have identical promoter activity.

Specific examples of promoters that may be useful in expressing the nucleic acid fragments of the invention include, but are not limited to, the oleosin promoter (PCT Publication WO99/65479, published Dec. 12, 1999), the maize 27 kD zein promoter (Ueda et al (1994) *Mol. Cell. Biol.* 14:4350-4359), the ubiquitin promoter (Christensen et al (1992) *Plant Mol. Biol.* 18:675-680), the SAM synthetase promoter (PCT Publication WO00/37662, published Jun. 29, 2000), the CaMV 35S (Odell et al (1985) *Nature* 313:810-812), and the promoter described in PCT Publication WO02/099063 published Dec. 12, 2002.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase 1. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to an association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Cosuppression technology constitutes the subject matter of U.S. Pat. No. 5,231,020, which issued to Jorgensen et al. on Jul. 27, 1999. The phenomenon observed by Napoli et al. in petunia was referred to as "cosuppression" since expression of both the endogenous gene and the introduced transgene were suppressed (for reviews see Vaucheret et al., Plant J. 16:651-659 (1998); and Gura, Nature 404:804-808 (2000)).

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) Plant J 16:651-659; and Gura (2000) Nature 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) Plant Cell 10:1747-1757).

In addition to cosuppression, antisense technology has also been used to block the function of specific genes in cells. Antisense RNA is complementary to the normally expressed RNA, and presumably inhibits gene expression by interacting with the normal RNA strand. The mechanisms by which the expression of a specific gene are inhibited by either antisense or sense RNA are on their way to being understood. However, the frequencies of obtaining the desired phenotype in a transgenic plant may vary with the design of the construct, the gene, the strength and specificity of its promoter, the method of transformation and the complexity of transgene insertion events (Baulcombe, Curr. Biol. 12(3):R82-84 (2002); Tang et al., Genes Dev. 17(1):49-63 (2003); Yu et al., Plant Cell. Rep. 22(3):167-174 (2003)). Cosuppression and antisense inhibition are also referred to as "gene silencing", "post-transcriptional gene silencing" (PTGS), RNA interference or RNAi. See for example U.S. Pat. No. 6,506,559.

MicroRNAs (mRNA) are small regulatory RNAs that control gene expression. mRNAs bind to regions of target RNAs and inhibit their translation and, thus, interfere with production of the polypeptide encoded by the target RNA. mRNAs can be designed to be complementary to any region of the target sequence RNA including the 3' untranslated region, coding region, etc. mRNAs are processed from highly structured RNA precursors that are processed by the action of a ribonuclease III termed DICER. While the exact mechanism of action of mRNAs is unknown, it appears that they function to regulate expression of the target gene. See, e.g., U.S. Patent Publication No. 2004/0268441 A1 which was published on Dec. 30, 2004.

The term "expression", as used herein, refers to the production of a functional end-product, be it mRNA or translation of mRNA into a polypeptide. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Overexpression" refers to the production of a functional end-product in transgenic organisms that exceeds levels of production when compared to expression of that functional end-product in a normal, wild type or non-transformed organism.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is using particle-accelerated or "gene gun" transformation technology (Klein et al. (1987) Nature (London) 327:70-73; U.S. Pat. No. 4,945,050), or an Agrobacterium-mediated method (Ishida Y. et al. (1996) Nature Biotech. 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al. (1986) *Cold Spring Harbor Symp. Quant Biol.* 51:263-273; Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

"Motifs" or "subsequences" refer to relatively short conserved regions of nucleic acids or amino acids that comprise part of a longer sequence. For example, it is expected that such conserved subsequences, such as those exemplified in SEQ ID NOS:49, 50, 52, and 52, would be important for function and could be used to identify new homologues of class I LOB domain proteins involved in controlling embryo/endosperm size in plants. It is expected that some or all of the elements may be found in an RE2 homolog. Also, it is expected that one or two of the conserved amino acids in any given motif may differ in a true RE2 homolog.

Thus, in one aspect, this invention concerns an isolated polynucleotide comprising:
(a) a nucleic acid sequence encoding a polypeptide involved in altering embryo/endosperm size during seed development, said polypeptide having at least 80% amino acid sequence identity, based on the Clustal V method of alignment, when compared to an amino acid sequence selected from the group consisting of SEQ ID NOS:37, 39, 41, 43, 45, 47, 49, 51, and 53; or
(b) a nucleic acid sequence set forth in SEQ ID NO:25 wherein said sequence comprises at least one of the following modifications:
  (i) nucleotide 278 is a T residue instead of a C;
  (ii) nucleotide 110 is a T residue instead of a G; or
  (iii) nucleotide 75 is deleted; or
(c) a nucleic acid sequence set forth in SEQ ID NO:34 wherein
  (i) nucleotides 4473 through 4829 correspond to a first exon, and
  (ii) nucleotides 5661 through 6110 correspond to a second exon, and
  further wherein the nucleotides of (c) (i) and/or (c)(ii) encode a polypeptide involved in altering embryo/endosperm size during seed development,
(d) the nucleic acid sequence set forth in SEQ ID NO:34 or 72; or
(e) the full complement of (a), (b), (c), (d), or SEQ ID NO:34; or
(f) all or part of a non-coding or coding region of the isolated polynucleotide comprising sequences of (a), (b) or SEQ ID NO:34 for use in co-suppression or antisense suppression of endogenous nucleic acid sequences encoding polypeptides involved in altering embryo/endosperm size during seed development.

Also of interest are recombinant DNA constructs comprising an isolated polynucleotide comprising any of the nucleotide sequences described herein operably linked in a sense or anti-sense orientation to at least one regulatory sequence. Such constructs can then be used to transform plants, plant tissue, or plant cells. Transformation methods are well known to those skilled in the art and are described above. Any plant, dicot or monocot can be transformed with such recombinant DNA constructs.

Examples of monocots include, but are not limited to, corn, wheat, rice, sorghum, millet, barley, palm, lily, *Alstroemeria*, rye, and oat.

Examples of dicots include, but are not limited to, soybean, rape, sunflower, canola, grape, guayule, columbine, cotton, tobacco, peas, beans, flax, safflower, and alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue. The plant tissue may in plant or in organ, tissue or cell culture.

The term "plant organ" refers to plant tissue or group of tissues that constitute a morphologically and functionally distinct part of a plant. The term "genome" refers to the following: 1. The entire complement of genetic material (genes and non-coding sequences) is present in each cell of an organism, or virus or organelle. 2. A complete set of chromosomes inherited as a (haploid) unit from one parent. The term "stably integrated" refers to the transfer of a nucleic acid fragment into the genome of a host organism or cell resulting in genetically stable inheritance.

Also within the scope of this invention are seeds obtained from such transformed plants and oil obtained from these seeds.

In another aspect, this invention concerns a method of altering embryo/endosperm size during seed development in a plant comprising:
(a) transforming plant cells or plant tissue with the recombinant DNA construct of the invention;
(b) regenerating transgenic plants from the transformed plant cells or plant tissue of (a);
(c) screening the transgenic plants of (b) for seeds having an altered embryo/endosperm size based on a comparison of embryo/endosperm size of seeds obtained from non-transformed plants.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily using *Agrobacterium tumefaciens*, and obtaining transgenic plants have been published for cootton (U.S. Pat. Nos. 5,004,863, 5,159, 135, 5,518,908); soybean (U.S. Pat. Nos. 5,569,834, 5,416, 011, McCabe et. al. (1988) *Bio/Technology* 6:923, Christou et al. (1988) *Plant Physiol.* 87:671-674); *Brassica* (U.S. Pat. No. 5,463,174); peanut (Cheng et al. (1996) *Plant Cell Rep.* 15:653-657, McKently et al. (1995) *Plant Cell Rep.* 14:699-703); papaya and pea (Grant et al. (1995) *Plant Cell Rep.* 15:254-258).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) (1987) 84:5354), barley (Wan and Lemaux (1994) *Plant Physiol.* 104:37); *Zea mays* (Rhodes et al. (1988) *Science* 240:204, Gordon-Kamm et al. (1990) *Plant Cell* 2:603-618, Fromm et al. (1990) *Bio/Technology* 8:833; Koziel et al. (1993) *Bio/Technology* 11: 194, Armstrong et al. (1995) *Crop Science* 35:550-557); oat (Somers et al. (1992) *Bio/Technology* 10: 15 89); orchard grass (Horn et al. (1988) *Plant Cell Rep.* 7:469); rice (Toriyama et al. (1986) *Theor. Appl. Genet.* 205:34; Part et al. (1996) *Plant Mol. Biol.* 32:1135-1148; Abedinia et al. (1997) *Aust. J. Plant Physiol.* 24:133-141; Zhang and Wu (1988) *Theor. Appl. Genet.* 76:835; Zhang et al. (1988) *Plant Cell Rep.* 7:379; Battraw and Hall (1992) *Plant Sci.* 86:191-202; Christou et al. (1991) *Bio/Technology* 9:957); rye (De la Pena et al. (1987) *Nature* 325:274); sugarcane (Bower and Birch (1992) *Plant J.* 2:409); tall fescue (Wang et al. (1992) *Bio/Technology* 10:691), and wheat (Vasil et al. (1992) *Bio/Technology* 10:667; U.S. Pat. No. 5,631, 152).

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect isolated nucleic acid fragment constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures the standard resource materials which describe specific conditions and procedures for the construction, manipulation and isolation of macromolecules (e.g., DNA molecules, plasmids, etc.), generation of recombinant organisms and screening and isolating of clones (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)) are well known.

In another aspect, this invention concerns a method of mapping genetic variations related to controlling embryo/endosperm size during seed development and/or altering oil phenotypes in plants comprising: (a) crossing two plant varieties; and evaluating genetic variations with respect to a nucleic acid sequence selected from the group consisting of SEQ ID NOS:25, 28, 30, 32, 34, 36, 38, 40, 42, 44, 46, 48, 50, 52, and 72; or a nucleic acid sequence encoding a polypeptide selected from the group consisting of SEQ ID NOS:26, 29, 31, 33, 37, 39, 41, 43, 45, 47, 49, 51, and 53; in progeny plants resulting from the cross of step (a) wherein the evaluation is made using a method selected from the group consisting of RFLP analysis, SNP analysis, and PCR-based analysis.

The terms "mapping genetic variation" or "mapping genetic variability" are used interchangeably and define the process of identifying changes in DNA sequence, whether from natural or induced causes, within a genetic region that differentiates between different plant lines, cultivars, varieties, families, or species. The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. Restriction fragment length polymorphism (RFLP) analysis takes advantage of this and utilizes Southern blotting with a probe corresponding to the isolated nucleic acid fragment of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms: ("RFLPs"). RFLPs have been widely used in human and plant genetic analyses (Glassberg, UK Patent Application 2135774; Skolnick et al, Cytogen. *Cell Genet.* 32:58-67 (1982); Botstein et al, *Ann. J. Hum. Genet.* 32:314-331 (1980); Fischer et al (PCT Application WO 90/13668; Uhlen, PCT Application WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W.H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, new polymorphisms can be identified by random sequencing of genomic or cDNA molecules. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, and the use of antibodies that are specific for the proteins encoded by the different alleles of the polymorphism or by other biochemical interpretation. SNPs can be sequenced by a number of methods. Two basic methods may be used for DNA sequencing, the chain termination method of Sanger et al, *Proc. Natl. Acad. Sci.* (U.S.A.) 74:5463-5467 (1977), and the chemical degradation method of Maxam and Gilbert, *Proc. Natl. Acad. Sci.* (U.S.A.) 74: 560-564 (1977).

Furthermore, single point mutations can be detected by modified PCR techniques such as the ligase chain reaction ("LCR") and PCR-single strand conformational polymorphisms ("PCR-SSCP") analysis. The PCR technique can also be used to identify the level of expression of genes in extremely small samples of material, e.g., tissues or cells from a body. The technique is termed reverse transcription-PCR ("RT-PCR").

In another embodiment, this invention concerns a method of molecular breeding to obtain altered embryo/endosperm size during seed development and/or altered oil phenotypes in plants comprising: (a) crossing two plant varieties; and (b) evaluating genetic variations with respect to: (i) a nucleic acid sequence selected from the group consisting of SEQ ID NOS: 25, 28, 30, 32, 34, 36, 38, 40, 42, 44, 46, 48, 50, 52, and 72; or a nucleic acid sequence encoding a polypeptide selected from the group consisting of SEQ ID NOS:26, 29, 31, 33, 37, 39, 41, 43, 45, 47, 49, 51, and 53; in progeny plants resulting from the cross of step (a) wherein the evaluation is made using a method selected from the group consisting of RFLP analysis, SNP analysis, and PCR-based analysis.

The term "molecular breeding" defines the process of tracking molecular markers during the breeding process. It is common for the molecular markers to be linked to phenotypic traits that are desirable. By following the segregation of the molecular marker or genetic trait, instead of scoring for a phenotype, the breeding process can be accelerated by growing fewer plants and eliminating assaying or visual inspection for phenotypic variation. The molecular markers useful in this process include, but are not limited to, any marker useful in identifying mapable genetic variations previously mentioned, as well as any closely linked genes that display synteny across plant species. The term "synteny" refers to the conservation of gene placement/order on chromosomes between different organisms. This means that two or more genetic loci, that may or may not be closely linked, are found on the same chromosome among different species. Another term for synteny is "genome colinearity".

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those set forth and described herein will be apparent to those skilled in the art from the foregoing description. Such modifications are also intended to fall within the scope of the appended claims.

The disclosure of each reference set forth herein is incorporated herein by reference in its entirety.

Example 1

Mapping of the *Oryza sativa* RE2 Locus to a Single Chromosome

Identification of the chromosome comprising the *Oryza sativa* RE2 locus was performed using Cleaved Amplified Polymorphic Sequence markers (CAPS markers). The *Oryza sativa* RE2 locus comprises the polynucleotide that, when mutated, is responsible for a reduced embryo 2, or re2, mutant phenotype as exemplified by Hong et al. (1996, *Development* 122:2051-2058). Mutant rice grains displaying the re2 phenotype show a reduced embryo size and an increased endosperm size. CAPS markers covering the entire rice genome were developed and, as set forth below, were used to identify the portion of the chromosome comprising the *Oryza sativa* RE2 Locus.

Developing of CAPS Markers

Mapping of the RE2 locus to a single chromosome required first developing CAPS markers covering the entire rice genome. CAPS markers were developed as follows.

Oligonucleotide primer sets were designed based on rice genomic sequence information available in the NCBI database. Information relating to the position of the sequences in the rice chromosomes was retrieved from the web sites of the Rice Genome Research Program (RGP), Tsukuba, Japan, or the Clemson University Genomics Institute, Clemson, S.C. The oligonucleotide primer sets were used to amplify portions of genomic DNA prepared from Indica (cv. Kasalth), Japonica (cv. Taichung 65), and Japonica (cv. Kinmaze) rice. The amplified fragments were digested with restriction endonucleases and polymorphisms identified between the three wild type rice as follows.

Genomic DNA was prepared from leaves of the three rice cultivars as follows. A 3 g piece from the leaf blade was ground using a mortar and pestle and suspended in 8 mL DNA extraction buffer (0.1 M ethylenediaminetetraacetic acid [EDTA], 1% N-lauroylsarcosine, 100 µg/mL proteinase K). The suspended sample was incubated at 50° C. for 1 hour, and debris removed by centrifuging at 3,400 rpm for 15 minutes using a RT-7 Plus centrifuge (Sorvall®) and transferring the supernatant to a fresh tube. The DNA was precipitated by adding 2 volumes of 100% ethanol and separated by centrifuging at 10,000 rpm for 15 minutes at 4° C. using an RC-5B centrifuge (Sorvall®). The DNA pellet was resuspended in 8 mL TE (10 mM tris, 1 mM EDTA) and reprecipitated with 16 mL 100% ethanol. After separation of the DNA pellet by centrifugation, it was resuspended in 3.7 mL TE, 50 µL 10 mg/mL ethidium bromide were added, the volume was brought up to 4 mL with TE, and 4.4 g CsCl were added. The solution was transferred to an OptiSeal™ tube (Beckman) and centrifuged for 16 hours at 52,000 rpm at 25° C. using an NVT65.2 rotor in an L8-M centrifuge (Beckman). After centrifugation the DNA band was visualized using an UV lamp and 500 µL removed using an 18-gauge needle in a 1 mL syringe. The DNA band was transferred to a 1.5 mL tube and the ethidium bromide removed by adding 500 µL isopropanol saturated with 20×SSPE buffer and centrifuging at 14,000 rpm for 30 seconds using a using a 5415C centrifuge (Eppendorf) and discarding the isopropanol phase. Removal of the ethidium bromide was accomplished by repeating addition of isopropanol and centrifugation 6 times. The DNA was then precipitated by adding 100 µL TE and 500 µL 100% ethanol and separated by centrifuging at 14,000 rpm for 15 minutes. The recovered DNA pellet was resuspended in 400 µL TE and 40 µL 3 M NaOAC. The DNA was precipitated one more time with the addition of 1 ml 100% ethanol, separated by centrifuging at 14,000 rpm for 15 minutes, rinsed with 500 µL 70% ethanol, dried, and resuspended in water to a concentration of 10 ng/µL. The genomic DNA was amplified using the oligonucleotide primer sets designed above using the following PCR conditions:

Amplifications were performed in 30 µL reactions containing 1 µL DNA prepared above (at 10 ng/µL concentration), 2 µL of 2.5 mM dNTPs, 2 µL 25 mM MgCl$_2$, 10 pmole of each primer, 0.3 µL Amplitaq gold (Perkin Elmer, Wellsley, Mass.), and 3 µL 10×PCR buffer. Amplification of DNA was performed by heating the reactions at 95° C. for 10 minutes followed by 40 cycles of 94° C. for 30 seconds, 56° C. for 30 seconds, and 72° C. for 30 seconds. Termination of the amplification reactions was accomplished by heating the reactions at 72° C. for 5 minutes.

Amplified DNA fragments were then digested with restriction endonucleases having 4 or 5 base recognition sites. Restriction endonuclease digestions were performed in 15 µL digestion reactions containing 2 µL of amplified DNA, 1.5 µL 10× reaction buffer, and 0.5 µL restriction enzyme. The digestion reactions were incubated for 1 hour at either 37° C. or at 60° C. depending on restriction endonuclease being utilized. Digested DNA products were loaded on a 2.5% agarose gel and separated by electrophoresis to analyze polymorphisms. Comparison of the CAPS markers developed for Japonica and Indica rice allowed the development of 26 CAPS markers for wild type rice.

Mapping of the *Oryza sativa* RE2 Locus to a Single Chromosome

Linkage between CAPS markers obtained for wild type rice and those obtained for re2 mutant plants was then analyzed. CAPS markers were prepared with genomic DNA from F3 Japonica rice plants whose F2 seed showed re2 phenotype and were compared to the CAPS markers prepared above. Two markers on chromosome 10 (markers C10 7.7 and C10 15.9) showed co-segregation with the re2-1 phenotype and were identified as follows.

Plants displaying an re2 mutant phenotype were obtained by crossing a Japonica cv. Taichung 65 mutant plant showing the re2-1 mutant phenotype with a plant of the Indica cultivar Kasalath and scoring the embryo phenotype of F2 mature seeds using a dissecting microscope. Twenty eight (28) seeds showing re2 mutant phenotype were sterilized and sown in soil. Genomic DNA was extracted from the leaves of these 28 F3 re2 mutant plants as follows. Leaf samples, weighing 300 mg, were ground to powder in liquid Nitrogen using a mortar and pestle. Each sample was then suspended in 750 µL extraction buffer containing 1.5 M NaCl, 0.2 M EDTA, 1 M tris and 3% CTAB (cetytrimethylammonium bromide) and vortexed. Proteins were removed by adding 50 µL chloroform to the samples, shaking for 20 minutes, centrifuging briefly in a microfuge, and decanting the supernatant, containing the DNA, into a new tube. Genomic DNA was precipitated by adding 300 µL isopropanol, mixing by quick vortexing, and allowing the aqueous phase to precipitate. The pellet, containing the DNA, was recovered in H$_2$O and used in amplification reactions as follows.

Marker C10 7.7 was amplified using oligonucleotide primers C10 6-3 and C10 6-4. Oligonucleotide primers C10 6-3 and C10 6-4 were developed as described above, have the nucleotide sequences set forth in SEQ ID NO:1 and SEQ ID NO:2, respectively, and have the sequences set forth as follows:

```
SEQ ID NO:1:    5'-TAGCAGCTGGGAAGAACAACATG-3'

SEQ ID NO:2:    5'-CGTGCACCACGTAACGTTAAGC-3'
```

Polymorphism was observed on CAPS marker C10 7.7 when the amplified DNA was digested with the restriction endonuclease Dde I, loaded on a 2.5% agarose gel, and separated by electrophoresis. Comparison of C10 7.7 CAPS markers allowed the identification of 4 recombination breakpoints between DNA prepared from wild type plants and that obtained from re2 mutant plants.

Marker C10 15.9 was amplified using oligonucleotide primers C10 15.9-1 and C10 15.9-2. Oligonucleotide primers C10 15.9-1 and C10 15.9-2 were developed as described above, have the nucleotide sequences set forth in SEQ ID NO:3 and SEQ ID NO:4, respectively, and have the sequences set forth as follows:

```
SEQ ID NO:3:    5'-CAGGGTTGTGTAAGGATCGTTG-3'

SEQ ID NO:4:    5'-GATCATCGTGTAGTACCAGGAC-3'
```

Polymorphism was observed on CAPS marker C10 15.9 when the amplified DNA was digested with the restriction endonuclease Msp I. This digestion produced additional bands in the Indica (Kasalath) background. Comparison of marker C10 15.9 prepared from DNA obtained from wild type plants with marker C10 15.9 prepared from DNA obtained from re2 mutant plants allowed the identification of 4 recombination breakpoints different from the ones identified with CAPS marker C10 7.7.

As explained above, comparison of CAPS markers prepared from DNA obtained from wild type rice and that obtained from F3 rice plants whose F2 seed showed re2 phenotype allowed the identification of 4 recombination breakpoints in CAPS marker C10 7.7 and 4 different recombination breakpoints in CAPS marker C10 15.9. These results indicate that the RE2 locus which contains the polynucleotide that when mutated is responsible for a re2 mutant phenotype maps to a region on chromosome 10 flanked by markers C10 7.7 and C10 15.9.

Example 2

Map-Based Cloning of the *Oryza sativa* RE2 Gene

In Example 1 the RE2 locus, comprising the RE2 gene, was mapped to a region on chromosome 10 flanked by markers C10 7.7 and C10 15.9. This Example describes cloning of the RE2 gene from F2 recombinant plants produced by crossing a re2-1 mutant plant (Japonica cv. Taichung 65) with an Indica cultivar, Kasalath using CAPS markers as follows.

F2 seeds obtained from self-fertilized F1 plants were screened for the re2 mutant phenotype to obtain populations for cloning the RE2 gene. Seeds (308) displaying an re2 mutant phenotype were germinated on MS medium containing 0.3% gelrite and incubated in a growth chamber for 3 weeks with a 16 hour light/8 hour dark cycle. When the plants on the plates were at third leaf stage, 5-10 mm of the tip of the leaf was removed and used for DNA amplification. Direct PCR amplification reactions were carried out as described in Klimyuk et al. (1993 *Plant J.* 3:493-494) with a modification of extending the sample boiling time to 4 minutes after the neutralization step. Briefly, the leaf tissue was collected in a sterile vial containing 40 µL of 0.25 M NaOH and incubated 30 seconds in a boiling water bath. Samples were neutralized by adding 40 µL 0.25 M HCl and 20 µL 0.5 M Tris-HCL, pH 8.0 containing 0.25% (v/v) Nonidet P-40 and boiling for an additional 4 minutes. Tissue samples were used immediately for amplification or stored at 4° C. until needed. Each 30 µL amplification reaction contained 10 pmole of each primer, 2 µL of 2.5 mM dNTPs, 2 µL of 25 mM MgCl$_2$, 1 µL leaf extract, 0.3 µL Amplitaq gold (Perkin Elmer), and 3 µL PCR buffer. The thermal cycler was set to 95° C. for 10 minutes, followed by 40 cycles of 94° C. for 4 minutes, 50° C. for 30 seconds, and 72° C. for 30 seconds followed by heating at 72° C. for 5 minutes.

DNA obtained from 44 of these 308 F2 recombinant plants contained breakpoints between CAPS markers C10 7.7 and C10 15.9 and were identified using CAPS markers C10 7.7 Hpy, C10 11.5, C10 11.0, C10 9.6, E08 93K, and E08 46K which were developed as follows.

Marker C10 7.7 Hpy was amplified using oligonucleotide primers C10-7.7 2 HPYIVF and C10-7.7 2 HPYIVR. Oligonucleotide primers C10-7.7 2 HPYIVF and C10-7.7 2 HPYIVR were developed as described in Example 1, have the nucleotide sequences set forth in SEQ ID NO:5 and SEQ ID NO:6, respectively, and have the sequences set forth as follows:

SEQ ID NO:5: 5'-ATTGTCTCGTGTGACAGCGC-3'

SEQ ID NO:6: 5'-CCGCAATTAATATTCCGAGC-3'

Polymorphism was observed on the C10 7.7 Hpy CAPS marker when the amplified DNA was digested with the restriction endonuclease HpyCH4 IV.

Marker C10 11.5 was amplified using oligonucleotide primers 11.5 HpyV and C10 11.5-9. Oligonucleotide primers 11.5 HpyV and C10 11.5-9 were developed as described in Example 1, have the nucleotide sequences set forth in SEQ ID NO:7 and SEQ ID NO:8, respectively, and have the sequences set forth as follows:

SEQ ID NO:7: 5'-AAAGTGTGGTAGGTGTCATCCAGTTG-3'

SEQ ID NO:8: 5'-GCCACATGATCATCCACTACCAATG-3'

Polymorphism was observed on the C10 11.5 CAPS marker when the amplified DNA was digested with the restriction endonuclease HpyCH4 V.

Marker C10 11.0 was amplified using oligonucleotide primers C10 11-5 and 11 HinfR. Oligonucleotide primers C10 11-5 and 11 HinfR were developed as described in Example 1, have the nucleotide sequences set forth in SEQ ID NO:9 and SEQ ID NO:10, respectively, and have the sequences set forth as follows:

SEQ ID NO:9: 5'-CTTTTTCCGACCCACATGAAGGT-3'

SEQ ID NO:10: 5'-TACAAACGCTCCTAAACCACCATGT-3'

Polymorphism was observed on the C10 11.0 CAPS marker when the amplified DNA was digested with the restriction endonuclease Hinf I.

Marker C10 9.6 was amplified using oligonucleotide primers 9.6 DraIF and 9.6 DraIR. Oligonucleotide primers 9.6 DraIF and 9.6 DraIR were developed as described in Example 1, have the nucleotide sequences set forth in SEQ ID NO:11 and SEQ ID NO:12, respectively, and have the sequences set forth as follows:

SEQ ID NO:11: 5'-TTTGGGTGCATTAAAGTGGACCA-3'

SEQ ID NO:12: 5'-GGGGTAATTCGGATGACCATG-3'

Polymorphism was observed on the C10 9.6 CAPS marker when the amplified DNA was digested with the restriction endonuclease Dra I.

Marker E08 93K was amplified using oligonucleotide primers E08 93KF and E08 93KR. Oligonucleotide primers E08 93KF and E08 93KR were developed as described in Example 1, have the nucleotide sequences set forth in SEQ ID NO:13 and SEQ ID NO:14, respectively, and have the sequences set forth as follows:

SEQ ID NO:13: 5'-CTCATAGCCGCCTAGCCTCATAG-3'

SEQ ID NO:14: 5'-GAAGCAGAGAAACTCCAACCTGG-3'

Polymorphism was observed on the E08 93K CAPS marker when the amplified DNA was digested with the restriction endonuclease HpyCH4 V.

Marker E08 46K was amplified using oligonucleotide primers E08 46KF and E08 46KR. Oligonucleotide primers E08 46KF and E08 46KR were developed as described in Example 1, have the nucleotide sequences set forth in SEQ ID NO:15 and SEQ ID NO:16, respectively, and have the sequences set forth as follows:

SEQ ID NO:15: 5'-GTTCATAGGTGCCAAATTTGGGTG-3'

SEQ ID NO:16: 5'-CACAAGTAACCCAATGCCCAAAC-3'

Polymorphism was observed on the E08 46K CAPS marker when the amplified DNA was digested with the restriction endonuclease Rsa I.

Analysis of recombination breakpoints identified 6 recombination breakpoints between DNA obtained from re2 mutant plants and CAPS marker E08 93K and 3 recombination breakpoints between DNA obtained from re2 mutant plants and CAPS marker C10 9.6. Information relating to the position of the sequences of the CAPS markers in the rice chromosomes was retrieved from the web sites of the Rice Genome Research Program (RGP), Tsukuba, Japan, or the Clemson University Genomics Institute, Clemson, S.C. This information revealed that the sequences for CAPS markers E08 93K and C10 9.6 were derived from two overlapping BAC clones, OSJNBa0050EO8 and OSJNBb0042KO8, that cover 190 Kb on rice chromosome 10. At least 10 genes are found in this region.

An additional CAPS marker, K08 21K, and a single nucleotide polymorphism-based (SNP-based) marker were generated that were derived from BAC OSJNBb0042K08, and mapped 25 Kb apart.

Marker K08 21K was amplified using oligonucleotide primers K08 21KF and K08 21KR. Oligonucleotide primers K08 21KF and K08 21KR were developed as described in Example 1, have the nucleotide sequences set forth in SEQ ID NO:17 and SEQ ID NO:18, respectively, and have the sequences set forth as follows:

```
SEQ ID NO:17:   5'-GTTCACCCATTAGTGATGCCTGG-3'

SEQ ID NO:18:   5'-GTTCACTCGATAAGAGCAATCGAAC-3'
```

Polymorphism was observed on the K08 21K CAPS marker when the amplified DNA was digested with the restriction endonuclease Taq I.

SNP-based marker K08 46K was amplified using primers K08 46KF and K08 46KR. Oligonucleotide primers K08 46KF and K08 46KR were developed as described in Example 1, have the nucleotide sequences set forth in SEQ ID NO:19 and SEQ ID NO:20, respectively, and have the sequences set forth as follows:

```
SEQ ID NO:19:   5'-GTTATGTTGCACACCTCCAGTAGTTAC-3'

SEQ ID NO:20:   5'-GTCAAGCCTGCTGTTACCCTTTAAG-3'
```

Amplified DNA products were purified using a Qiagen PCR purification kit (Qiagen, Valencia, Calif.) and 100 ng of each purified DNA was used for direct sequencing. Of 9 recombination breakpoints analyzed 3 were found in marker K08 21K and 1 was found in marker K08 46K confining the RE2 gene to a 25 Kb region between these two markers.

This 25 Kb region contains DNA corresponding to two putative genes. One is gene OSJNBb0042K08.8 that is predicted to encode a myosin-like protein and is found in the NCBI database as Version ML77142.1 having NCBI General Identifier No. 18652508. The other one is gene OSJNBb0042K08.9 that is predicted to encode a protein of unknown function and is found in the NCBI database as Version AAL77143.1 having NCBI General Identifier No. 18652509.

The regions corresponding to these two genes were sequenced in genomic DNA obtained from mutant alleles re2-1, re2-2 and re2-3 to identify the RE2 gene. Amplification of exon 1 was performed using oligonucleotide primers LOB-82F and LOB R1 and amplification of exon 2 was performed using oligonucleotide primers LOB F2 and LOB R2. Oligonucleotide primers LOB-82F, LOB R1, LOB F2, and LOB R2 have the nucleotide sequences set forth in SEQ ID NO:21, SEQ ID NO:22, SEQ ID NO:23, and SEQ ID NO:24, respectively, and have the sequences set forth as follows:

```
SEQ ID NO:21:   5-GTCAAGCCTGCTGTTACCCTTTAAG-3'

SEQ ID NO:22:   5'-CCACCATGACGAACATCTAAATG-3'

SEQ ID NO:23:   5'-GTATAGCTCCCAACCATTTCTCCTC-3'

SEQ ID NO:24:   5'-CCAACATCACCATCATCGTCTTC-3'
```

Amplification reactions were carried out using the same conditions that were used for CAPS marker amplifications in Example 1 except that 20 ng of DNA was used per reaction and the annealing temperature was 55° C. Amplified DNA products were cloned into p-GEM T easy Vector (Promega, Madison, Wis.) and, for each amplification reaction, plasmid DNA was prepared from at least 4 independent colonies using a Qiagen miniprep kit (Qiagen, Valencia, Calif.). Plasmids were sequenced using the M13 forward and reverse sequencing primers.

No mutation was found in the portion of DNA corresponding to the gene encoding the myosin-like protein, but mutations were found in the region encoding the unknown protein. This means that the RE2 gene has the sequence found in NCBI having locus tag OSJNBb0042K08.9 that is predicted to encode a protein of unknown function and is found in the NCBI database as Version AAL77143.1 having NCBI General Identifier No. 18652509.

The nucleotide sequence of the *Oryza sativa* RE2 gene is set forth in SEQ ID NO:25 and the amino acid sequence deduced from translating nucleotides 1 through 807 of SEQ ID NO:25 is set forth in SEQ ID NO:26. Nucleotides 808-810 of SEQ ID NO:25 correspond to a stop codon. The nucleotide sequence set forth in SEQ ID NO:25 is the same as the one found in the NCBI database having locus tag OSJNBb0042K08.9 that is predicted to encode a protein of unknown function. The amino acid sequence set forth in SEQ ID NO:26 is the same as the one for the protein of unknown function found in the NCBI database as Version AAL77143.1 having NCBI General Identifier No. 18652509 that is set forth here in SEQ ID NO:27.

Identification of Mutations Responsible for an re2 Phenotype

Mutations in the RE2 gene responsible for the re2 phenotype were determined by comparing the nucleotide sequences obtained for DNA from wild-type rice with the nucleotide sequences obtained for DNA from rice exhibiting an re2 phenotype. Three re2 mutant alleles were identified and labeled re2-1, re2-2, and re2-3. The nucleotide sequence obtained for mutant allele re2-1 is set forth in SEQ ID NO:28 and the amino acid sequence obtained by translating nucleotides 1 through 807 of SEQ ID NO:28 is set forth in SEQ ID NO:29. Nucleotides 808 through 810 of SEQ ID NO:28 correspond to a stop codon. The nucleotide sequence obtained for mutant allele re2-2 is set forth in SEQ ID NO:30 and the amino acid sequence obtained by translating nucleotides 1 through 807 of SEQ ID NO:30 is set forth in SEQ ID NO:31. Nucleotides 808 through 810 of SEQ ID NO:30 correspond to a stop codon. The nucleotide sequence obtained for mutant allele re2-3 is set forth in SEQ ID NO:32 and the amino acid sequence obtained by translating nucleotides 1-378 of SEQ ID NO:32 is set forth in SEQ ID NO:33. Nucleotides 379 through 381 of SEQ ID NO:32 correspond to a stop codon.

FIG. 1A-C shows an alignment of the nucleotide sequences obtained for the coding regions of wild type RE2 (SEQ ID NO:25), and mutants re2-1 (SEQ ID NO:28), re2-2 (SEQ ID NO:30), and re2-3 (SEQ ID NO:32). Changes in the nucleotide sequence are indicated by a star below the alignment and by a box around the nucleotides at that position. As seen in FIG. 1, mutant allele re2-1 had a T residue at nucleotide 279, mutant allele re2-2 had a T residue at nucleotide 110, and mutant allele re2-3 had the C at nucleotide 75 deleted. These nucleotide changes result in changes in the amino acid sequence.

FIG. 2 shows an alignment of the amino acid sequences obtained for wild type RE2 protein (SEQ ID NO:26), and mutant proteins re2-1 (SEQ ID NO:29), and re2-2 (SEQ ID NO:31). Amino acids that change between the wild type and mutant are indicated by a box around the amino acids that are different at that position. As seen in FIG. 2, mutant allele re2-1 protein had an isoleucine at amino acid 93 instead of the highly conserved threonine, mutant allele re2-2 protein had a phenylalanine instead of the conserved cysteine at amino acid 37. The deletion of a nucleotide at position 75 in mutant allele re2-3 gene produced a frame shift that results in a 127 amino acid polypeptide (set forth in SEQ ID NO:33) that shares identity with the first 25 amino acids of wild type RE2 protein but whose remaining 102 amino acids share little or no homology with wild type RE2 protein or mutant proteins re2-1 or re2-2.

Example 3

Confirmation of the Function of the *Oryza sativa* RE2 Gene

Functional confirmation of the identity of the *Oryza sativa* RE2 gene identified in Example 2 was performed using genetic complementation. Rice callus cells derived from wild type and re2 mutant plants were transformed with a genomic DNA fragment comprising the RE2 gene. Restoration of the embryo size of the re2 mutant cells transformed with the genomic DNA fragment comprising the RE2 gene confirmed that the *Oryza sativa* RE2 gene identified in Example 2 is the sole target of mutations giving rise to the re2 phenotype. Cloning of the genomic fragment comprising the wild type RE2 gene and transformation into rice cells were performed as follows.

A genomic DNA fragment containing wild type *Oryza sativa* RE2 gene was obtained from a lambda rice genomic DNA library (Stratagene) as follows. The genomic library was screened using a DNA probe obtained using primers LOB F2 (SEQ ID NO:23) and LOB R2 (SEQ ID NO:24) that, as indicated in Example 2, above, may be used to amplify exon 2 of the RE2 gene. Of 8 clones identified, one clone, named RE2G4, contained a 15 Kb insert comprising an approximately 9 Kb fragment flanked by two BamH I sites and comprising the RE2 gene. One of the BamH I sites was located 4472 bp upstream of the ATG initiation codon in the RE2 gene and the other one was located 3089 bp downstream of the termination codon of the RE2 gene. Nucleotides 4473 through 4829 correspond to a first exon, nucleotides 4830 through 5660 correspond to an intron, and nucleotides 5661 through 6110 correspond to the second exon. Nucleotides 6111 through 6113 form a termination codon. The nucleotide sequence of this approximately 9 Kb BamH I fragment is set forth in SEQ ID NO:34.

The approximately 9 Kb BamH I fragment comprising the RE2 coding region (set forth in SEQ ID NO:34) was removed from clone RE2G4 by digestion with BamH I and was subcloned into the BamH I site of the pML18 transformation vector to produce vector OsRE2 pML18. Transformation vector pML18 is derived from the commercially available vector pGEM9z (obtained from Gibco-BRL which is owned by Invitrogen, Carlsbad, Calif.) and was modified by adding a cassette to express the bacterial hygromycin phosphotransferase gene. The bacterial hygromycin phosphotransferase gene confers resistance to the antibiotic used as selectable marker for rice transformation. A Sal I fragment, containing a cassette comprising the cauliflower mosaic virus 35S promoter, driving expression of the bacterial hygromycin phosphotransferase gene, followed by nucleotides 848 to 1550 of the 3' end of the nopaline synthase gene, was inserted at the Sal I site of vector pGEM9z to produce pML18. The nucleotide sequence of pML18 is set forth in SEQ ID NO:35.

Vector OsRE2 pML18 was introduced into callus derived from wild type rice plants and from re2 mutant plants using a Biolistic PDS-1000/He gun (BioRAD Laboratories, Hercules, Calif.) and the particle bombardment technique (Klein et al. (1987) *Nature* (London) 327:70-73) as follows.

Embryogenic callus cultures derived from the scutellum of germinating rice seeds were used as source material for transformation experiments. This material was generated by germinating sterile rice seeds on N6-2,4D media (N6 salts, N6 vitamins, 2.0 mg/l 2,4-D, 100 mg/L myo-inositol, 300 mg/L casamino acids, and 2.7 g/L proline) in the dark at 27-28° C. Embryogenic callus proliferating from the scutellum of the embryos was then transferred to fresh N6-2,4D media. Callus cultures were maintained by routine sub-culture at two-week intervals and used for transformation within 4 weeks of initiation. The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)).

Callus was prepared for transformation by arranging 0.5-1.0 mm callus pieces approximately 1 mm apart in a circular area of about 4 cm in diameter in the center of a circle of Whatman #541 paper placed on CM media and incubating in the dark at 27-28° C. for 3-5 days. Vector OsRE2pML 18 was introduced into wild type callus cells and re2 mutant rice callus cells using a Biolistic PDS-1000/He gun (BioRAD Laboratories, Hercules, Calif.).

Transformation of mutant callus with vector OsRE2pML 18 produced 16 transgenic plants of which 7 transgenic plants produced seed. T2 seed from 6 plants showed a wild type to re2 mutant phenotype segregating at a 3:1 ratio. Restoration of wild type phenotype in re2 mutant plants by vector OsRE2pML 18 indicates that the 9,203 bp rice genomic DNA fragment present in vector OsRE2pML 18 was capable of complementing an re2 mutation. This confirms that the *Oryza sativa* RE2 gene has the sequence found in NCBI having locus tag OSJNBb0042K08.9 that is predicted to encode a protein of unknown function found in the NCBI database as Version AAL77143.1 having NCBI General Identifier No. 18652509. These results also indicate that the 9,203 bp rice genomic DNA fragment in vector OsRE2pML 18 used in these transformations and set forth in SEQ ID NO:34 contains the complete set of regulatory elements required for proper complementation of an re2 mutant phenotype and involved in altering embryo/endosperm size during seed development.

Example 4

Composition of cDNA Libraries

Isolation and Sequencing of cDNA Clones Encoding Polypeptides Involved in Altering Embryo/Endosperm Size During Seed Development The sequence of the *Oryza sativa* RE2 gene was identified in Example 2 and its function was confirmed in Example 3 as being involved in altering embryo/endosperm size during seed development. Identification of genes from other crops involved in altering embryo/endosperm size during seed development is set forth in Examples 4 and 5. cDNAs encoding polypeptides homologous to rice RE2 protein were identified by electronically screening the Du Pont proprietary database using BLAST analysis (Basic Local Alignment Search Tool; Altschul et al. (1993) *J. Mol. Biol.* 215:403-410). Clones derived from cDNA libraries representing mRNAs from various corn (*Zea maize*), *Euphorbia lagascae*, columbine (*Aquilegia vulgaris*), guar (*Cyamopsis tetragonoloba*), rice (*Oryza sativa*), soybean (*Glycine max*), and wheat (*Triticum aestivum*) tissues were identified as encoding homologs to the rice RE2 protein. The libraries were prepared as described below. The characteristics of the libraries are described in Table 1.

TABLE 1

Libraries from Corn, *Euphorbia lagascae*, Columbine, Guar, Rice, Soybean, and Wheat

| Library | Tissue | Clone |
|---|---|---|
| ceflf | Corn entire fertilized ear 3 to 12 days after pollination | ceflf.pk001.f4:fis |
| cpf1c | Corn pooled BMS treated with chemicals related to protein synthesis[1] | cpf1c.pk006.d18a:fis |
| cpi1c | Corn pooled BMS treated with chemicals related to biochemical compound synthesis[2] | cpi1c.pk005.a12:fis |
| cr1n | Corn root from 7 day old seedlings[3] | cr1n.pk0028.h3a:fis |
| eel1c | *Euphorbia lagascae* developing seeds | eel1c.pk003.b10:fis |
| eav1c | Columbine developing seeds | eav1c.pk003.c9 |
| lds3c | Guar seeds harvested 32 days after flowering | lds3c.pk011.j11:fis |
| sdr1f | Soybean 10 day old root | sdr1f.pk005.d21.f:fis |
| wdr1f | Wheat entire developing root | wdr1f.pk002.l10:fis |

[1] Chemicals used included chloramphenicol, cyclohexamide, aurintricarboylic acid.
[2] Chemicals used included sorbitol, egosterol, taxifolin, methotrexate, D-mannose, D-galactose, alpha-amino adipic acid, ancymidol.
[3] This library was normalized essentially as described in U.S. Pat. No. 5,482,845 cDNA libraries representing mRNAs from the tissues described in Table 1 were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) Science 252:1651). The resulting ESTs were analyzed using a Perkin Elmer Model 377 fluorescent sequencer.

Full-insert sequence (FIS) data was generated utilizing a modified transposition protocol. Clones identified for FIS were recovered from archived glycerol stocks as single colonies, and plasmid DNAs were isolated via alkaline lysis. Isolated DNA templates were reacted with vector primed M13 forward and reverse oligonucleotides in a PCR-based sequencing reaction and loaded onto automated sequencers. Confirmation of clone identification was performed by sequence alignment to the original EST sequence from which the FIS request was made.

Confirmed templates were transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA was then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones were randomly selected from each transposition reaction, plasmid DNAs were prepared via alkaline lysis, and templates were sequenced (ABI Prism dye-terminator ReadyReaction mix) outward from the transposition event site, utilizing unique primers specific to the binding sites within the transposon.

Sequence data was collected (ABI Prism Collections) and assembled using Phred and Phrap (Ewing et al. (1998) *Genome Res.* 8:175-185; Ewing and Green (1998) *Genome Res.* 8:186-194). Phred re-reads the ABI sequence data, re-calls the bases, assigns quality values, and writes the base calls and quality values into editable output files. Phrap is a sequence assembly program that uses the quality values assigned by Phred to increase the accuracy of the assembled sequence contigs. Assemblies are viewed using the Consed sequence editor (Gordon et al. (1998) *Genome Res.* 8:195-202).

Example 5

Identification and Characterization of cDNA Clones Encoding Putative Homologs of the *Oryza sativa* RE2 Protein Clones containing cDNA inserts encoding polypeptides homologous to rice RE2 protein were identified by conducting BLAST (Basic Local Alignment Search Tool; Altschul et al. (1993) *J. Mol. Biol.* 215:403-410) searches for similarity to sequences contained in the Du Pont proprietary database. The sequences identified were also compared, using BLAST, to the Genbank database.

A BLASTX search was performed to identify cDNAs encoding proteins similar to those encoded by the RE2 gene. BLASTX compares the translation, in all six reading frames, of the nucleotide query sequence to a protein database. As mentioned in Example 2, the *Oryza sativa* RE2 gene has the sequence found in the NCBI database having locus tag OSJNBb0042K08.9 that is predicted to encode a protein of unknown function found in the NCBI database as Version AAL77143.1 having NCBI General Identifier No. 18652509. Thus, the polypeptides encoded by the cDNAs identified in the BLASTX search are similar to the protein of unknown function found in the NCBI database as Version AAL77143.1 having NCBI General Identifier No. 18652509.

The BLASTX search using the nucleotide sequences from the clones listed in Table 1 revealed that the polypeptides encoded by these cDNAs had similarity to the *Oryza sativa* protein having NCBI General Identifier No. 18652509 and the *Arabidopsis thaliana* LOB domain 18 protein having NCBI General Identifier No. 17227164. Set forth in Table 2 are the BLASTX results for individual ESTs ("EST"), or for the sequences of the entire cDNA inserts comprising the indicated cDNA clones ("FIS"):

TABLE 2

BLAST Results for Sequences Encoding Polypeptides Homologous To *O. sativa* RE2 Protein and *A. thaliana* LOB Domain 18 Protein

| | aa | | BLAST pLog Score | |
|---|---|---|---|---|
| Clone | SEQ ID NO: | Status | 18652509 | 17227164 |
| rice RE2 | 26 | FIS | >180.00 | 73.70 |
| cef1f.pk001.f4:fis | 37 | FIS | 58.00 | 58.30 |
| cpf1c.pk006.d18a:fis | 39 | FIS | 36.00 | 38.22 |
| cpi1c.pk005.a12:fis | 41 | FIS | 60.70 | 58.15 |
| cr1n.pk0028.h3a:fis | 43 | FIS | 34.22 | 34.40 |
| eel1c.pk003.b10:fis | 45 | FIS | 59.05 | 69.40 |
| eav1c.pk003.c9 | 47 | EST | 47.00 | 51.70 |
| lds3c.pk011.j11:fis | 49 | FIS | 53.10 | 56.40 |
| sdr1f.pk005.d21.f:fis | 51 | FIS | 39.15 | 41.10 |
| wdr1f.pk002.l10:fis | 53 | FIS | 36.30 | 33.70 |

The data set forth in Table 3 presents the percent identity, calculated using the Clustal V method of alignment, of the amino acid sequences set forth in SEQ ID NOS:26, 37, 39, 41, 43, 45, 47, 49, 51, and 53, with the *Oryza sativa* protein having NCBI General Identifier No. 18652509 (set forth in SEQ ID NO:27), and the *Arabidopsis thaliana* LOB domain 18 protein (NCBI General Identifier No. 17227164; set forth in SEQ ID NO:54).

TABLE 3

Percent Identity of Amino Acid Sequences Deduced From Nucleotide Sequences of cDNA Clones Encoding Putative *O. sativa* RE2 Homolog Polypeptides

| | | Percent Identity to | |
|---|---|---|---|
| | aa SEQ ID NO. | 18652509 | 17227164 |
| rice RE2 | 26 | 100.00 | 49.6 |
| cef1f.pk001.f4:fis | 37 | 59.1 | 56.9 |
| cpf1c.pk006.d18a:fis | 39 | 38.5 | 40.4 |
| cpi1c.pk005.a12:fis | 41 | 57.8 | 52.7 |
| cr1n.pk0028.h3a:fis | 43 | 45.8 | 47.6 |
| eel1c.pk003.b10:fis | 45 | 53.4 | 58.6 |
| eav1c.pk003.c9 | 47 | 79.2 | 85.4 |
| lds3c.pk011.j11:fis | 49 | 41.8 | 47.4 |
| sdr1f.pk005.d21.f:fis | 51 | 40.8 | 42.3 |
| wdr1f.pk002.l10:fis | 53 | 43.9 | 41.2 |

Sequence alignments and percent identity calculations were performed using the Megalign program of the LASERGENE bioinformatics computing suite (DNASTAR Inc., Madison, Wis.). Multiple alignment of the sequences was performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191.) and the default parameters (GAP PENALTY=10, GAP LENGTH PENALTY=10). Default parameters for pairwise alignments using the Clustal V method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode polypeptides with homology to the *O. sativa* RE2 protein and the *A. thaliana* LOB 18 domain protein.

Example 6

Structure of the *Oryza sativa* RE2 Protein and its Putative Homologs

As set forth on Table 3, Example 5, the amino acid sequence of the RE2 polypeptide (SEQ ID NO:26) set forth in Example 2, above, to be able to complement an re2 mutant phenotype was identical to the *Oryza sativa* protein having NCBI General Identifier No. 18652509 (SEQ ID NO:27) and had sequence similarity to the *Arabidopsis thaliana* LOB domain 18 protein having NCBI General Identifier No. 17227164 (set forth in SEQ ID NO:54).

The LOB domain 18 protein is considered to belong in the class I group of the Lateral Organ Boundaries (LOB) domain protein plant-specific gene family. The Class I LOB domain proteins contain a C-block, a GAS-block, and a leucine zipper motif (Shuai, B. et al., 2002, *Plant Phys.* 129:747-761). Thus, it is expected that the *Oryza sativa* RE2 protein and its homologs also contain a C-block, a GAS-block, and a leucine zipper motif. The consensus sequences of these motifs were identified using a Clustal V alignment and are indicated in FIG. 3A-C.

FIG. 3A-C depicts the Clustal V alignment obtained for the amino acid sequences from the wild type rice RE2 protein (SEQ ID NO:26), the *O. sativa* protein having NCBI General Identifier No. 18652509 (SEQ ID NO:27), the *A. thaliana* LOB domain 18 protein having NCBI General Identifier No. 17227164 (SEQ ID NO:54), and the amino acid sequences of the polypeptides encoded by corn clones cef1f.pk001.f4:fis (SEQ ID NO:37), cpf1c.pk006.d18a:fis (SEQ ID NO:39), cpi1c.pk005.a12:fis (SEQ ID NO:41), and cr1n.pk0028.h3a:fis (SEQ ID NO:43), *Euphorbia lagascae* clone eel1c.pk003.b10:fis (SEQ ID NO:45), columbine clone eav1c.pk003.c9 (SEQ ID NO:47), guar clone lds3c.pk011.j11:fis (SEQ ID NO:49), soybean clone sdr1f.pk005.d21.f:fis (SEQ ID NO:51), and wheat clone wdr1f.pk002.l10:fis (SEQ ID NO:53). The program uses dashes to maximize the alignment. An asterisk (*) below the alignment indicates amino acids conserved among all the sequences. The C-block, a GAS-block, and a leucine zipper conserved motifs are set forth boxed.

Table 4 sets forth the amino acid position of the C-block, Gas Block, and leucine zipper conserved amino acid domains in SEQ ID NOS:26, 54, 37, 39, 41, 43, 45, 47, 49, 51, and 53. The amino acids in each domain are indicated in FIG. 1 and the consensus sequence for each domain described below the table.

TABLE 4

Location of the Conserved Domains in *Oryza sativa* RE2 and its Putative Homologs

| SEQ ID NO: | C-Block | Gas Block | | Leu Zipper |
|---|---|---|---|---|
| | | N-end | C-end | |
| 26/27 | 33-54 | 63-74 | 103-111 | 116-134 |
| 54 | 37-58 | 67-78 | 107-115 | 120-138 |
| 37 | 34-55 | 64-75 | 104-112 | 117-135 |
| 39 | 24-45 | 54-65 | 94-102 | 107-125 |
| 41 | 32-53 | 62-73 | 102-110 | 115-133 |
| 43 | 24-45 | 44-55 | 84-92 | 97-115 |
| 45 | 30-51 | 60-71 | 100-108 | 113-131 |

TABLE 4-continued

Location of the Conserved Domains in *Oryza sativa* RE2 and its Putative Homologs

| SEQ ID NO: | C-Block | Gas Block | | Leu Zipper |
| | | N-end | C-end | |
| --- | --- | --- | --- | --- |
| 47 | | 22-33 | 62-70 | 75-93 |
| 49 | 20-41 | 50-61 | 90-98 | 103-121 |
| 51 | 16-37 | 46-57 | 86-94 | 99-117 |
| 53 | 12-33 | 42-53 | 82-90 | 95-113 |

In the following consensus sequences the amino acids are indicated with their one letter code, positions where more than one amino acid is found at that position are indicated in parenthesis and the amino acids separated by a slash. An X is used in cases where at a certain position any amino acid may be present. The amino acids comprising the C-Block, GAS Block N-end and C-end, and Leu Zipper identified here follow:

The C block consensus sequence found in RE2 homologs is set forth in SEQ ID NO:55 and corresponds to:

```
SEQ ID NO:55:
    PCGACKFLRR(K/R)C(V/Q/A)X(G/D/E)C(V/I)FAP(Y/H)F
```

The GAS block has 49 amino acids that have an N-end consensus sequence set forth in SEQ ID NO:56 and a C-end C-end consensus sequence set forth in SEQ ID NO:57.

```
SEQ ID NO:56:      FAA(V/I)HKVFGASN

SEQ ID NO:57:      RDP(V/I)(F/Y)GCV(A/S)
```

The consensus sequence for the Leucine Zipper domain is set forth in SEQ ID NO:58 and corresponds to:

```
SEQ ID NO:58:
LQ(Q/H)QV(A/V/G)XLQX(E/Q)(L/V)X(Y/Q/H)(L/A/V)

(Q/K/R)X(H/Q/Y)(L/V)
```

The C-Block, GAS Block N-end and C-end, and Leu Zipper consensus sequences set forth above were identified in a Clustal V alignment of polypeptides similar to the *Oryza sativa* RE2, thus, they should be present in any polypeptide having the same function in altering embryo/endosperm size during seed development as the *Oryza sativa* RE2 polypeptide.

Example 7

Cloning and Sequencing of a Genomic Fragment Encoding a Maize Putative RE2 Homolog and Preparation of a Recombinant DNA Construct to Complement re2 Mutant Plants A genomic DNA fragment encoding a corn RE2 homolog was amplified from a maize genomic library, cloned and sequenced. Then, the portion of DNA from the initiator ATG to the terminator codon of the fragment encoding the maize RE2 homolog was used to replace the portion of DNA from the initiator ATG to the terminator codon encoding the rice RE2 protein in vector OsRE2 pML18 as follows.

Cloning and Sequencing of a Genomic Fragment Encoding a Maize RE2 Homolog

The polynucleotide in cDNA clone cpi1c.pk005.a12 was identified in Example 5 as encoding a polypeptide with similarity to the *Oryza sativa* RE2 protein. A genomic fragment comprising the open reading frame in clone cpi1c.pk005.a12 was amplified from a maize genomic library (Stratagene, Catalog No. 946102) using oligonucleotide primers Cpi Bbs1 F and Cpi Bsa1 R. Oligonucleotide primers Cpi Bbs1 F and Cpi Bsa1 R were designed based on the sequence of clone cpi1c.pk005.a12, are set forth in SEQ ID NO:59 and SEQ ID NO:60, respectively, and have the sequences set forth as follows:

```
SEQ ID NO:59:
5'-GAAGACCAATGAGCGCTGGCGGCGGCAGCAG-3'

SEQ ID NO:60:
5'-GGTCTCCTCATCTTGAGTGTGGCGGCGGGTGCTC-3'
```

Amplification was performed using the conditions suggested by the manufacturer of the library. The amplified DNA product comprising a maize RE2 homolog gene was named ZmRE2 ORF, was cloned into vector pGEM-T-easy, and was sequenced. The nucleotide sequence obtained for ZmRE2 ORF is set forth in SEQ ID NO:61. Nucleotides 79 through 429 correspond to the first exon, nucleotides 430 through 1363 correspond to an intron, and nucleotides 1364 through 1784 correspond to the second exon, and nucleotides 1785 to 1787 correspond to a stop codon.

A. Preparation of a Recombinant DNA Construct Encoding a Putative Maize RE2 Homolog A recombinant DNA construct was prepared in which a genomic DNA fragment encoding a maize RE2 homolog present in ZmRE2 ORF was used to replace the *Oryza sativa* RE2 coding region in vector OsRE2pML 18 (prepared in Example 3, above). The resulting chimeric construct comprises the genomic DNA fragment encoding a maize RE2 homolog (referred to as ZmRE2 ORF) surrounded by the sequences upstream of the initiator ATG and downstream of the termination codon from vector OsRE2pML 18. This chimeric construct was prepared by amplifying portions upstream of the initiator ATG and downstream of the termination signal in vector OsRE2pML 18, adding these portions to the pGEM-T-easy vector containing ZmRE2 ORF and then replacing the *Oryza sativa* RE2 coding sequence with this chimeric fragment in vector OsRE2pML 18 as follows.

B. Amplification of a Fragment 5' of the *O. sativa* RE2 Gene in Vector OsRE2pML 18

A portion of the DNA fragment 5' of the initiator ATG in vector OsRE2pML 18 was amplified using oligonucleotide primers RE2 pro Bst 2F and RE2 PRO R Bbs. Oligonucleotide primers RE2 pro Bst 2F and RE2 PRO R Bbs are set forth in SEQ ID NO:62 and SEQ ID NO:63, respectively, and have the sequences set forth as follows:

```
SEQ ID NO:62:
5'-CACCATCATGTCAGTGTGCCAATACGCTAAACTTAGAAGA-3'

SEQ ID NO:63:
5'-GAAGACGCTCATTCTTGGAATGAGCCCCCA-3'
```

The amplified fragment comprises a portion of the *Oryza sativa* RE2 promoter and was cloned in pGEM-T-easy (Promega) to create plasmid RE2PRO whose sequence is set forth in SEQ ID NO:64.

C. Preparation of a Chimera Comprising the Fragments Amplified in A and B Above

Digestion of the pGEM-T-easy vector containing ZmRE2 ORF (prepared in A above) with Bbs I and Aat II produced a 1760 bp fragment. Restriction endonuclease Bbs I cuts the pGEM-T-easy vector containing ZmRE2 ORF immediately upstream of the initiator ATG and Aat II cuts in the vector, downstream of the maize stop codon. Plasmid RE2PRO was digested with Bbs I which cuts immediately upstream of the initiator ATG, and with Sal I which cuts in the vector's multiple cloning region. The 4316 bp fragment obtained from plasmid RE2PRO was ligated to the 1760 bp fragment obtained from the pGEM-T-easy vector containing ZmRE2 ORF by introducing the fragments in DH10B competent cells (Invitrogen). The resulting plasmid contains a portion of the *Oryza sativa* RE2 promoter region operably linked to the first codon of the genomic fragment encoding a maize RE2 homolog in ZmRE2 ORF.

D. Amplification of a Fragment 3' of the *O. sativa* RE2 Gene in Vector OsRE2pML 18

A portion of the DNA fragment 3' of the termination signal in vector OsRE2pMl18 was amplified using oligonucleotide primers RE2 TERM XbaI R and RE2 TERM EcoBspml. Oligonucleotide primers RE2 TERM XbaI R and RE2 TERM EcoBspml are set forth in SEQ ID NO:65 and SEQ ID NO:66, respectively, and have the sequences set forth as follows:

```
SEQ ID NO:65:
5'-GTAAAAGGATCTAGACACCTGGCTCTAGCCTCCAAGTA-3'

SEQ ID NO:66:
5'-TGGAGCGAATTCACCTGCCAAGATGATCCTCCTCACTGTGTGTGATC
ATC-3'
```

The amplified DNA product comprising a portion of the *Oryza sativa* RE2 terminator region was cloned into vector pGEM9z to produce plasmid pRE2TERGEM whose sequence is set forth in SEQ ID NO:67.

E. Addition of the Fragment Amplified in D Above to the Chimera of C Above

The maize sequences 3' of the termination signal were replaced for rice sequences as follows.

Plasmid pRE2TERGEM was digested with Xba I and Eco RI to remove a 758 bp fragment containing only sequences from the termination region of the rice RE2 gene. This 758 bp fragment was cloned into vector pGEM7 that had been digested with Xba I and Eco RI to produce plasmid RE2TERMpGEM7.

Plasmid RE2TERMpGEM7 was digested with Bsp HI and Eco RI and an approximately 3.7 Kb fragment was recovered. The chimera prepared in C, above, was digested with Bsa I and Eco RI to remove the fragment comprising a portion of the *Oryza sativa* RE2 promoter region operably linked to the genomic fragment encoding a maize RE2 homolog. These two fragments were ligated to form a plasmid comprising a portion of the rice RE2 promoter operably linked to the genomic fragment encoding a maize RE2 homolog operably linked to a portion of the rice RE2 terminator region.

F. Preparation of a Vector Comprising a Genomic Fragment Encoding a Maize RE2 Homolog Under the Control of the *Oryza sativa* RE2 Promoter and Terminator A vector comprising the genomic fragment encoding the maize RE2 homolog under the control of the *Oryza sativa* RE2 promoter and terminator regions was assembled from vector OsRE2pML 18 and the chimeric fragment prepared in part E above, as follows.

Vector OsRE2pML 18 and the chimeric fragment prepared in part E above were digested with restriction endonucleases Bst EII and SexAI. Digestion of vector OsRE2pML 18 removed the *Oryza sativa* RE2 coding region and portions of the promoter and terminator regions from vector OsRE2pML 18 leaving a 12.1 Kb DNA fragment. Digestion of the fragment prepared in part E above, produced a 3.1 Kb fragment comprising a fragment encoding a maize RE2 homolog between portions of the *Oryza sativa* RE2 promoter and terminator regions. Ligation of the 12.1 and 3.1 Kb fragments produced a vector comprising a fragment encoding a maize RE2 homolog under the control of the *Oryza sativa* RE2 promoter and terminator. The vector comprising the maize RE2 homolog open reading frame under the control of the *Oryza sativa* RE2 promoter and terminator regions was named ZmRE2pML 18.

Example 8

Genetic Complementation of a Rice re2 Mutant Plant with an RE2 Homolog from Corn Confirmation of the function of the corn RE2 homolog, identified in Example 5 above, was performed using genetic complementation. Rice callus cells derived from rice re2 mutant plants were transformed with vector ZmRE2pML 18 prepared as described in Example 7 above. Transformations were performed using a Biolistic PDS-1000/He gun and the particle bombardment technique as in Example 3 above.

Transformation of re2-1 mutant cells with vector ZmRE2pML 18 produced 14 transgenic plants. Thirteen of these fourteen plants produced seeds of which ten plants produced seeds having wild type appearance. Some of the seeds produced by these 10 plants had a wild-type phenotype and some had an re2 mutant phenotype. The ratio of seeds having a wild-type appearance to seeds having an re2 mutant phenotype varied in each plant. Approximately 25% to 70% of the seeds obtained from individual re2-1 mutant plants transformed with vector ZmRE2pML 18 had a wild-type appearance. Restoration of a wild-type appearance in seeds from plants regenerated from re2 mutant cells transformed with the vector comprising the fragment encoding the corn RE2 homolog indicates that the corn RE2 homolog, encoded by ZmRE2 (SEQ ID NO:61), is capable of complementing an re2 mutation. These results suggest that the corn RE2 homolog performs the same function in corn as the rice RE2 protein performs in rice.

Example 9

Identification of a cDNA Clone Encoding OsRE2

A cDNA clone encoding OsRE2 was identified by screening a rice phage cDNA library using an RE2-specific probe.

The phage cDNA library was prepared from total RNA extracted from developing rice seeds harvested 2-5 days after pollination as follows. Total RNA was extracted using a TRIazol® Reagent containing phenol and guanidine thiocyanate (Life Technologies Inc., Rockville, Md.). Poly(A) mRNA was purified from the total RNA using mRNA Purification kits which consist of oligo (dT)-cellulose spin columns (Amersham Pharmacia Biotech Inc., Piscataway, N.J.). cDNA was synthesized using 5.5 µg of poly(A) mRNA and cDNA synthesis kits (Stratagene, La Jolla, Calif.), following manufacturer's protocol with the exception of using Superscript® reverse transcriptase (Life Technologies Inc.) in the first step instead of Moloney murine leukemia virus reverse transcriptase. The cDNA was size-fractionated using BRL cDNA Size Fraction Columns (GIBCO-BRL). Fractions 1 to 13 were precipitated, resuspended, and ligated with 1 μg Uni-ZAP XR vector following the manufacturer's instructions. After incubation for two days at 4° C. the ligated DNA was packaged using Gigapack III Gold® packaging extract (Stratagene, La Jolla, Calif.). The titer of the resulting library was approximately $7.8 \times 10^5$ plaque forming units per mL (pfu/mL). The cDNA phage library was amplified following the manufacturer's instructions and 150 mL of phage cDNA library were obtained. The amplified library had a $5.5 \times 10^8$ pfu/mL titer.

Screening for the RE2 cDNA was performed following standard protocols well known to those skilled in the art (Ausubel et al. 1993, "Current Protocols in Molecular Biology" John Wiley & Sons, USA, or Sambrook et al. 1989. Molecular Cloning: A Laboratory Manual, Cold Spring Harbor Laboratory Press). Briefly, $1.0 \times 10^6$ pfu were plated, transferred to nylon membranes, and subjected to hybridization with radioactively-labeled RE2 second exon probe. The nucleotide sequence of RE2 second exon probe is shown in SEQ ID NO:71. Following hybridization the membranes were exposed to film where approximately 1 positive plaque was detected per 100,000 plaques plated. Eight plaques that gave a positive signal were isolated after a second round of screening. Lambda phage DNA was prepared from all 8 plaques, converted into plasmid DNA, and sequenced. Six of the eight clones contained a cDNA sequence encoding OsRE2. One of these six clones, RE2 cDNA C1, had a 5'UTR that extended 196 nucleotides upstream of the ATG start codon predicted from the genomic sequence. The nucleotide sequence of clone RE2 cDNA C1 is shown in SEQ ID NO:72.

---

What is claimed is:

1. An isolated polynucleotide comprising:
   (a) the nucleic acid sequence set forth in SEQ ID NO:25 wherein said sequence comprises at least one of the following modifications:
      (i) nucleotide 278 is a T residue instead of a C;
      (ii) nucleotide 110 is a T residue instead of a G; or,
      (iii) nucleotide 75 is deleted; or
   (b) the full complement of (a).

2. A recombinant DNA construct comprising the isolated polynucleotide of claim 1 operably linked to at least one regulatory sequence.

3. A plant comprising in its genome the recombinant DNA construct of claim 2.

4. Seeds and progeny thereof obtained from the plant of claim 3, wherein the seeds comprise the recombinant construct.

5. The plant of claim 3 wherein said plant is selected from the group consisting of rice, corn, sorghum, millet, rye, soybean, canola, wheat, barley, oat, beans, and nuts.

6. Transformed plant tissue or plant cells comprising the recombinant DNA construct of claim 2.

7. The transformed plant tissue or plant cells of claim 6 wherein the plant is selected from the group consisting of rice, corn, sorghum, millet, rye, soybean, canola, wheat, barley, oat, beans, and nuts.

* * * * *

SEQUENCE LISTING

```
<160> NUMBER OF SEQ ID NOS: 72

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide primer C10 6-3

<400> SEQUENCE: 1
tagcagctgg gaagaacaac atg                                              23

<210> SEQ ID NO 2
<211> LENGTH: 22
<212> TYPE: DNA
<213> ORGANISM: artificial sequence
<220> FEATURE:
<223> OTHER INFORMATION: Oligonucleotide primer C10 6-4

<400> SEQUENCE: 2
cgtgcaccac gtaacgttaa gc                                               22

<210> SEQ ID NO 3
<211> LENGTH: 22
<212> TYPE: DNA
<213> ORGANISM: artificial sequence
<220> FEATURE:
<223> OTHER INFORMATION: oligonucleotide primer C10 15.9-1

<400> SEQUENCE: 3
cagggttgtg taaggatcgt tg                                               22

<210> SEQ ID NO 4
<211> LENGTH: 22
<212> TYPE: DNA
<213> ORGANISM: artificial sequence
<220> FEATURE:
<223> OTHER INFORMATION: Oligonucleotide primer C10 15.9-2

<400> SEQUENCE: 4
gatcatcgtg tagtaccagg ac                                               22

<210> SEQ ID NO 5
<211> LENGTH: 20
<212> TYPE: DNA
<213> ORGANISM: artificial sequence
<220> FEATURE:
```

```
<223> OTHER INFORMATION: Oligonucleotide primer C10-7.7 2 HPYIVF

<400> SEQUENCE: 5
attgtctcgt gtgacagcgc                                               20

<210> SEQ ID NO 6
<211> LENGTH: 20
<212> TYPE: DNA
<213> ORGANISM: artificial sequence
<220> FEATURE:
<223> OTHER INFORMATION: Oligonucleotide primer C10-7.7 2 HPYIVR

<400> SEQUENCE: 6
ccgcaattaa tattccgagc                                               20

<210> SEQ ID NO 7
<211> LENGTH: 26
<212> TYPE: DNA
<213> ORGANISM: artificial sequence
<220> FEATURE:
<223> OTHER INFORMATION: Oligonucleotide primer 11.5 HpyV

<400> SEQUENCE: 7
aaagtgtggt aggtgtcatc cagttg                                        26

<210> SEQ ID NO 8
<211> LENGTH: 25
<212> TYPE: DNA
<213> ORGANISM: artificial sequence
<220> FEATURE:
<223> OTHER INFORMATION: Oligonucleotide primer C10 11.5-9

<400> SEQUENCE: 8
gccacatgat catccactac caatg                                         25

<210> SEQ ID NO 9
<211> LENGTH: 23
<212> TYPE: DNA
<213> ORGANISM: artificial sequence
<220> FEATURE:
<223> OTHER INFORMATION: Oligonucleotide primer C10 11-5

<400> SEQUENCE: 9 cttttttccga cccacatgaa ggt                                          23

<210> SEQ ID NO 10
<211> LENGTH: 25
<212> TYPE: DNA
<213> ORGANISM: artificial sequence
<220> FEATURE:
<223> OTHER INFORMATION: Oligonucleotide primer 11 HinfR

<400> SEQUENCE: 10
tacaaacgct cctaaaccac catgt                                         25

<210> SEQ ID NO 11
<211> LENGTH: 23
<212> TYPE: DNA
<213> ORGANISM: artificial sequence
<220> FEATURE:
<223> OTHER INFORMATION: Oligonucleotide primer 9.6 DraIF

<400> SEQUENCE: 11
tttgggtgca ttaaagtgga cca                                           23
```

```
<210> SEQ ID NO 12
<211> LENGTH: 21
<212> TYPE: DNA
<213> ORGANISM: artificial sequence
<220> FEATURE:
<223> OTHER INFORMATION: Oligonucleotide primer 9.6 DraIR

<400> SEQUENCE: 12
ggggtaattc ggatgaccat g                                             21

<210> SEQ ID NO 13
<211> LENGTH: 23
<212> TYPE: DNA
<213> ORGANISM: Artificial sequence
<220> FEATURE:
<223> OTHER INFORMATION: Oligonucleotide primer E08 93KF

<400> SEQUENCE: 13
ctcatagccg cctagcctca tag                                           23

<210> SEQ ID NO 14
<211> LENGTH: 23
<212> TYPE: DNA
<213> ORGANISM: artificial sequence
<220> FEATURE:
<223> OTHER INFORMATION: Oligonucleotide primer E08 93KR

<400> SEQUENCE: 14
gaagcagaga aactccaacc tgg                                           23

<210> SEQ ID NO 15
<211> LENGTH: 24
<212> TYPE: DNA
<213> ORGANISM: Artificial sequence
<220> FEATURE:
<223> OTHER INFORMATION: Oligonucleotide primer E08 46KF

<400> SEQUENCE: 15
gttcataggt gccaaatttg ggtg                                          24

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer E08 46KR

<400> SEQUENCE: 16
cacaagtaac ccaatgccca aac                                           23

<210> SEQ ID NO 17
<211> LENGTH: 23
<212> TYPE: DNA
<213> ORGANISM: Artificial sequence
<220> FEATURE:
<223> OTHER INFORMATION: Oligonucleotide primer K08 21KF

<400> SEQUENCE: 17
gttcacccat tagtgatgcc tgg                                           23

<210> SEQ ID NO 18
<211> LENGTH: 25
<212> TYPE: DNA
<213> ORGANISM: Artificial sequence
<220> FEATURE:
<223> OTHER INFORMATION: Oligonucleotide primer K08 21KR
```

```
<400> SEQUENCE: 18
gttcactcga taagagcaat cgaac                                              25

<210> SEQ ID NO 19
<211> LENGTH: 27
<212> TYPE: DNA
<213> ORGANISM: artificial sequence
<220> FEATURE:
<223> OTHER INFORMATION: Oligonucleotide primer K08 46KF

<400> SEQUENCE: 19
gttatgttgc acacctccag tagttac                                            27

<210> SEQ ID NO 20
<211> LENGTH: 25
<212> TYPE: DNA
<213> ORGANISM: Artificial sequence
<220> FEATURE:
<223> OTHER INFORMATION: Oligonucleotide primer K08 46KR

<400> SEQUENCE: 20
gtcaagcctg ctgttaccct ttaag                                              25

<210> SEQ ID NO 21
<211> LENGTH: 25
<212> TYPE: DNA
<213> ORGANISM: Artificial sequence
<220> FEATURE:
<223> OTHER INFORMATION: Oligonucleotide primer LOB-82F

<400> SEQUENCE: 21
gtcaagcctg ctgttaccct ttaag                                              25

<210> SEQ ID NO 22
<211> LENGTH: 23
<212> TYPE: DNA
<213> ORGANISM: Artificial sequence
<220> FEATURE:
<223> OTHER INFORMATION: Oligonucleotide primer LOB R1

<400> SEQUENCE: 22
ccaccatgac gaacatctaa atg                                                23

<210> SEQ ID NO 23
<211> LENGTH: 25
<212> TYPE: DNA
<213> ORGANISM: Artificial sequence
<220> FEATURE:
<223> OTHER INFORMATION: Oligonucleotide primer LOB F2

<400> SEQUENCE: 23
gtatagctcc caaccatttc tcctc                                              25

<210> SEQ ID NO 24
<211> LENGTH: 23
<212> TYPE: DNA
<213> ORGANISM: Artificial sequence
<220> FEATURE:
<223> OTHER INFORMATION: Oligonucleotide primer LOB R2

<400> SEQUENCE: 24
ccaacatcac catcatcgtc ttc                                                23

<210> SEQ ID NO 25
<211> LENGTH: 810
```

```
<212> TYPE: DNA
<213> ORGANISM: Oryza sativa

<400> SEQUENCE: 25
atgagctcgt cggtggttgt gagcgcgagc ggcagcggca gcggcggcgg aggaggagga      60
ggaggtggcg gcgccggagg tggaggagga ggtgggccgt gcggggcgtg caagttcttg     120
cggcggaagt gcgtgcaggg gtgcatcttc gcgccctact cgactcgga ggccggggcg      180 gcgcacttcg cggcggtgca aaggtgttc ggcgccagca acgtgtccaa gctgctgcag      240
cagatcccgg cgcaccgccg cctcgacgcc gtcgtcacca tctgctacga ggcccaggcc     300
cgcctccgcg accccgtcta cggctgcgtc gcccacatct ccacctcca acaccaggtg      360 gcaggtctcc agtccgagct gaactacctg caaggtcacc tctcgacgat ggagctgccg     420
tcgccgccgc cctacgtcgc cgggccgacc ctggcgccgc acagccaca gccactgatg      480 ccgatgaccg ccgccgccaa cttcaacttc tccgacctgc catcgtcgtc ggcggccaac     540
attccggtca ccgccgacct gtccaccctc tttgacccac tgccggcggc gcagccgcag     600
tggggactat accagcagca gcaacaccac caccagcagc tgcatcatca cccctatgac     660
cggatgggcg acggctcgtc gagcagcaga ggcggcgacg acgatggcag cgacggcggc     720
gacttgcaag cgctggcgag ggagcttctt gaccgccatg acggtcgtc gtcgagctcc      780 aagctggagc cgccacctca cacacagtga                                       810

<210> SEQ ID NO 26
<211> LENGTH: 269
<212> TYPE: PRT
<213> ORGANISM: Oryza sativa

<400> SEQUENCE: 26

Met Ser Ser Ser Val Val Ser Ala Ser Gly Ser Gly Ser Gly Gly
1               5                   10                  15

Gly Gly Gly Gly Gly Gly Gly Ala Gly Gly Gly Gly Gly Gly
            20                  25                  30

Pro Cys Gly Ala Cys Lys Phe Leu Arg Arg Lys Cys Val Gln Gly Cys
            35                  40                  45

Ile Phe Ala Pro Tyr Phe Asp Ser Glu Ala Gly Ala Ala His Phe Ala
        50                  55                  60

Ala Val His Lys Val Phe Gly Ala Ser Asn Val Ser Lys Leu Leu Gln
65                  70                  75                  80

Gln Ile Pro Ala His Arg Arg Leu Asp Ala Val Val Thr Ile Cys Tyr
                85                  90                  95

Glu Ala Gln Ala Arg Leu Arg Asp Pro Val Tyr Gly Cys Val Ala His
            100                 105                 110

Ile Phe His Leu Gln His Gln Val Ala Gly Leu Gln Ser Glu Leu Asn
        115                 120                 125

Tyr Leu Gln Gly His Leu Ser Thr Met Glu Leu Pro Ser Pro Pro
    130                 135                 140

Tyr Val Ala Gly Pro Thr Leu Ala Pro Gln Pro Gln Pro Leu Met
145                 150                 155                 160

Pro Met Thr Ala Ala Ala Asn Phe Asn Phe Ser Asp Leu Pro Ser Ser
                165                 170                 175

Ser Ala Ala Asn Ile Pro Val Thr Ala Asp Leu Ser Thr Leu Phe Asp
            180                 185                 190

Pro Leu Pro Ala Ala Gln Pro Gln Trp Gly Leu Tyr Gln Gln Gln Gln
        195                 200                 205
```

His His His Gln Gln Leu His His Pro Tyr Asp Arg Met Gly Asp
    210                 215                 220

Gly Ser Ser Ser Arg Gly Gly Asp Asp Gly Ser Asp Gly Gly
225                 230                 235                 240

Asp Leu Gln Ala Leu Ala Arg Glu Leu Leu Asp Arg His Gly Arg Ser
                245                 250                 255

Ser Ser Ser Lys Leu Glu Pro Pro His Thr Gln
            260                 265

<210> SEQ ID NO 27
<211> LENGTH: 269
<212> TYPE: PRT
<213> ORGANISM: Oryza sativa
<220> FEATURE:
<221> NAME/KEY: MISC_FEATURE
<223> OTHER INFORMATION: NCBI General Identification No. 18652509

<400> SEQUENCE: 27

Met Ser Ser Ser Val Val Ser Ala Ser Gly Ser Gly Ser Gly Gly
1               5                   10                  15

Gly Gly Gly Gly Gly Gly Gly Ala Gly Gly Gly Gly Gly Gly
            20                  25                  30

Pro Cys Gly Ala Cys Lys Phe Leu Arg Arg Lys Cys Val Gln Gly Cys
            35                  40                  45

Ile Phe Ala Pro Tyr Phe Asp Ser Glu Ala Gly Ala Ala His Phe Ala
    50                  55                  60

Ala Val His Lys Val Phe Gly Ala Ser Asn Val Ser Lys Leu Leu Gln
65                  70                  75                  80

Gln Ile Pro Ala His Arg Arg Leu Asp Ala Val Val Thr Ile Cys Tyr
                85                  90                  95

Glu Ala Gln Ala Arg Leu Arg Asp Pro Val Tyr Gly Cys Val Ala His
            100                 105                 110

Ile Phe His Leu Gln His Gln Val Ala Gly Leu Gln Ser Glu Leu Asn
    115                 120                 125

Tyr Leu Gln Gly His Leu Ser Thr Met Glu Leu Pro Ser Pro Pro
130                 135                 140

Tyr Val Ala Gly Pro Thr Leu Ala Pro Gln Pro Gln Pro Leu Met
145                 150                 155                 160

Pro Met Thr Ala Ala Ala Asn Phe Asn Phe Ser Asp Leu Pro Ser Ser
                165                 170                 175

Ser Ala Ala Asn Ile Pro Val Thr Ala Asp Leu Ser Thr Leu Phe Asp
            180                 185                 190

Pro Leu Pro Ala Ala Gln Pro Gln Trp Gly Leu Tyr Gln Gln Gln Gln
    195                 200                 205

His His His Gln Gln Leu His His Pro Tyr Asp Arg Met Gly Asp
    210                 215                 220

Gly Ser Ser Ser Arg Gly Gly Asp Asp Gly Ser Asp Gly Gly
225                 230                 235                 240

Asp Leu Gln Ala Leu Ala Arg Glu Leu Leu Asp Arg His Gly Arg Ser
                245                 250                 255

Ser Ser Ser Lys Leu Glu Pro Pro His Thr Gln
            260                 265

<210> SEQ ID NO 28
<211> LENGTH: 810
<212> TYPE: DNA

<213> ORGANISM: Oryza sativa

<400> SEQUENCE: 28

| | | | | | |
|---|---|---|---|---|---|
| atgagctcgt | cggtggttgt | gagcgcgagc | ggcagcggca | gcggcggcgg | aggaggagga | 60 |
| ggaggtggcg | gcgccggagg | tggaggagga | ggtgggccgt | gcggggcgtg | caagttcttg | 120 |
| cggcggaagt | gcgtgcaggg | gtgcatcttc | gcgccctact | tcgactcgga | ggccggggcg | 180 |
| gcgcacttcg | cggcggtgca | caaggtgttc | ggcgccagca | acgtgtccaa | gctgctgcag | 240 |
| cagatcccgg | cgcaccgccg | cctcgacgcc | gtcgtcatca | tctgctacga | ggcccaggcc | 300 |
| cgcctccgca | ccccgtcta | cggctgcgtc | gcccacatct | tccacctcca | acaccaggtg | 360 |
| gcaggtctcc | agtccgagct | gaactacctg | caaggtcacc | tctcgacgat | ggagctgccg | 420 |
| tcgccgccgc | cctacgtcgc | cgggccgacc | ctggcgccgc | acagccaca | gccactgatg | 480 |
| ccgatgaccg | ccgccgccaa | cttcaacttc | tccgacctgc | catcgtcgtc | ggcggccaac | 540 |
| attccggtca | ccgccgacct | gtccaccctc | tttgacccac | tgccggcggc | gcagccgcag | 600 |
| tggggactat | accagcagca | gcaacaccac | caccagcagc | tgcatcatca | ccctatgac | 660 |
| cggatgggcg | acggctcgtc | gagcagcaga | ggcggcgacg | acgatggcag | cgacggcggc | 720 |
| gacttgcaag | cgctggcgag | ggagcttctt | gaccgccatg | gacggtcgtc | gtcgagctcc | 780 |
| aagctggagc | cgccacctca | cacacagtga | | | | 810 |

<210> SEQ ID NO 29
<211> LENGTH: 269
<212> TYPE: PRT
<213> ORGANISM: Oryza sativa

<400> SEQUENCE: 29

Met Ser Ser Ser Val Val Ser Ala Ser Gly Gly Ser Gly Gly
1               5                   10                  15

Gly Gly Gly Gly Gly Gly Gly Ala Gly Gly Gly Gly Gly Gly
            20                  25                  30

Pro Cys Gly Ala Cys Lys Phe Leu Arg Arg Lys Cys Val Gln Gly Cys
            35                  40                  45

Ile Phe Ala Pro Tyr Phe Asp Ser Glu Ala Gly Ala Ala His Phe Ala
    50                  55                  60

Ala Val His Lys Val Phe Gly Ala Ser Asn Val Ser Lys Leu Leu Gln
65                  70                  75                  80

Gln Ile Pro Ala His Arg Arg Leu Asp Ala Val Val Ile Ile Cys Tyr
                85                  90                  95

Glu Ala Gln Ala Arg Leu Arg Asp Pro Val Tyr Gly Cys Val Ala His
                100                 105                 110

Ile Phe His Leu Gln His Gln Val Ala Gly Leu Gln Ser Glu Leu Asn
        115                 120                 125

Tyr Leu Gln Gly His Leu Ser Thr Met Glu Leu Pro Ser Pro Pro
    130                 135                 140

Tyr Val Ala Gly Pro Thr Leu Ala Pro Gln Pro Gln Pro Leu Met
145                 150                 155                 160

Pro Met Thr Ala Ala Ala Asn Phe Asn Phe Ser Asp Leu Pro Ser Ser
                165                 170                 175

Ser Ala Ala Asn Ile Pro Val Thr Ala Asp Leu Ser Thr Leu Phe Asp
            180                 185                 190

Pro Leu Pro Ala Ala Gln Pro Gln Trp Gly Leu Tyr Gln Gln Gln Gln
        195                 200                 205

```
His His His Gln Gln Leu His His His Pro Tyr Asp Arg Met Gly Asp
    210                 215                 220

Gly Ser Ser Ser Ser Arg Gly Gly Asp Asp Gly Ser Asp Gly Gly
225                 230                 235                 240

Asp Leu Gln Ala Leu Ala Arg Glu Leu Leu Asp Arg His Gly Arg Ser
                245                 250                 255

Ser Ser Ser Ser Lys Leu Glu Pro Pro Pro His Thr Gln
                260                 265
```

<210> SEQ ID NO 30
<211> LENGTH: 810
<212> TYPE: DNA
<213> ORGANISM: Oryza sativa

<400> SEQUENCE: 30

```
atgagctcgt cggtggttgt gagcgcgagc ggcagcggca gcggcggcgg aggaggagga      60
ggaggtggcg gcgccggagg tggaggagga ggtgggccgt gcggggcgtt caagttcttg     120
cggcggaagt gcgtgcaggg gtgcatcttc gcgccctact tcgactcgga ggccggggcg     180
gcgcacttcg cggcggtgca caaggtgttc ggcgccagca acgtgtccaa gctgctgcag     240
cagatcccgg cgcaccgccg cctcgacgcc gtcgtcacca tctgctacga ggcccaggcc     300
cgcctccgcg accccgtcta cggctgcgtc gcccacatct tccacctcca acaccaggtg     360
gcaggtctcc agtccgagct gaactacctg caaggtcacc tctcgacgat ggagctgccg     420
tcgccgccgc cctacgtcgc cgggccgacc ctggcgccgc acagccaca gccactgatg      480
ccgatgaccg ccgccgccaa cttcaacttc tccgacctgc atcgtcgtc ggcggccaac      540
attccggtca ccgccgacct gtccaccctc tttgacccac tgccggcggc gcagccgcag     600
tggggactat accagcagca gcaacaccac caccagcagc tgcatcatca ccctatgac      660
cggatgggcg acggctcgtc gagcagcaga ggcggcgacg acgatggcag cgacggcggc     720
gacttgcaag cgctggcgag ggagcttctt gaccgccatg gacggtcgtc gtcgagctcc     780
aagctggagc cgccacctca cacacagtga                                      810
```

<210> SEQ ID NO 31
<211> LENGTH: 269
<212> TYPE: PRT
<213> ORGANISM: Oryza sativa

<400> SEQUENCE: 31

```
Met Ser Ser Ser Val Val Val Ser Ala Ser Gly Ser Gly Ser Gly Gly
1               5                   10                  15

Gly Gly Gly Gly Gly Gly Gly Gly Ala Gly Gly Gly Gly Gly Gly
                20                  25                  30

Pro Cys Gly Ala Phe Lys Phe Leu Arg Arg Lys Cys Val Gln Gly Cys
            35                  40                  45

Ile Phe Ala Pro Tyr Phe Asp Ser Glu Ala Gly Ala His Phe Ala
    50                  55                  60

Ala Val His Lys Val Phe Gly Ala Ser Asn Val Ser Lys Leu Leu Gln
65                  70                  75                  80

Gln Ile Pro Ala His Arg Arg Leu Asp Ala Val Val Thr Ile Cys Tyr
                85                  90                  95

Glu Ala Gln Ala Arg Leu Arg Asp Pro Val Tyr Gly Cys Val Ala His
            100                 105                 110

Ile Phe His Leu Gln His Gln Val Ala Gly Leu Gln Ser Glu Leu Asn
        115                 120                 125
```

Tyr Leu Gln Gly His Leu Ser Thr Met Glu Leu Pro Ser Pro Pro Pro
    130                 135                 140

Tyr Val Ala Gly Pro Thr Leu Ala Pro Pro Gln Pro Gln Pro Leu Met
145                 150                 155                 160

Pro Met Thr Ala Ala Ala Asn Phe Asn Phe Ser Asp Leu Pro Ser Ser
                165                 170                 175

Ser Ala Ala Asn Ile Pro Val Thr Ala Asp Leu Ser Thr Leu Phe Asp
            180                 185                 190

Pro Leu Pro Ala Ala Gln Pro Gln Trp Gly Leu Tyr Gln Gln Gln Gln
        195                 200                 205

His His His Gln Gln Leu His His His Pro Tyr Asp Arg Met Gly Asp
    210                 215                 220

Gly Ser Ser Ser Ser Arg Gly Gly Asp Asp Asp Gly Ser Asp Gly Gly
225                 230                 235                 240

Asp Leu Gln Ala Leu Ala Arg Glu Leu Leu Asp Arg His Gly Arg Ser
                245                 250                 255

Ser Ser Ser Ser Lys Leu Glu Pro Pro Pro His Thr Gln
            260                 265

<210> SEQ ID NO 32
<211> LENGTH: 809
<212> TYPE: DNA
<213> ORGANISM: Oryza sativa

<400> SEQUENCE: 32
atgagctcgt cggtggttgt gagcgcgagc ggcagcggca gcggcggcgg aggaggagga      60
ggaggtggcg gcgcggaggt ggaggaggag gtgggccgtg cggggcgtgc aagttcttgc     120
ggcggaagtg cgtgcagggg tgcatcttcg cgccctactt cgactcggag gccggggcgg     180
cgcacttcgc ggcggtgcac aaggtgttcg gcgccagcaa cgtgtccaag ctgctgcagc     240
agatcccggc gcaccgccgc tcgacgccgt cgtcaccat ctgctacgag gcccaggccc      300
gcctccgcga ccccgtctac ggctgcgtcg cccacatctt ccacctccaa caccaggtgg     360
caggtctcca gtccgagctg aactacctgc aaggtcacct ctcgacgatg gagctgccgt     420
cgccgccgcc ctacgtcgcc gggccgaccc tggcgccgcc acagccacag ccactgatgc     480
cgatgaccgc cgccgccaac ttcaacttct ccgacctgcc atcgtcgtcg gcggccaaca     540
ttccggtcac cgccgacctg tccaccctct tgaccccact gccggcggcg cagccgcagt     600
ggggactata ccagcagcag caacaccacc accagcagct gcatcatcac ccctatgacc     660
ggatgggcga cggctcgtcg agcagcagag gcggcgacga cgatggcagc gacggcggcg     720
acttgcaagc gctggcgagg gagcttcttg accgccatgg acggtcgtcg tcgagctcca     780
agctggagcc gccacctcac acacagtga                                       809

<210> SEQ ID NO 33
<211> LENGTH: 126
<212> TYPE: PRT
<213> ORGANISM: Oryza sativa

<400> SEQUENCE: 33

Met Ser Ser Ser Val Val Val Ser Ala Ser Gly Ser Gly Ser Gly Gly
1               5                   10                  15

Gly Gly Gly Gly Gly Gly Gly Ala Glu Val Glu Glu Glu Val Gly
                20                  25                  30

Arg Ala Gly Arg Ala Ser Ser Cys Gly Gly Ser Ala Cys Arg Gly Ala

```
                  35                  40                  45
Ser Ser Arg Pro Thr Ser Thr Arg Arg Pro Gly Arg Arg Thr Ser Arg
     50                  55                  60

Arg Cys Thr Arg Cys Ser Ala Pro Ala Thr Cys Pro Ser Cys Cys Ser
65                  70                  75                  80

Arg Ser Arg Arg Thr Ala Ala Ser Thr Pro Ser Ser Pro Ser Ala Thr
                85                  90                  95

Arg Pro Arg Pro Ala Ser Ala Thr Pro Ser Thr Ala Ala Ser Pro Thr
            100                 105                 110

Ser Ser Thr Ser Asn Thr Arg Trp Gln Val Ser Ser Pro Ser
            115                 120                 125

<210> SEQ ID NO 34
<211> LENGTH: 9203
<212> TYPE: DNA
<213> ORGANISM: Oryza sativa

<400> SEQUENCE: 34
ggatccatcc aacagtttct cctaaatatc agaataaagt tgaagtaact gctttgctgc      60
cgtccaagat atattgcaaa ggacaaaagg ttcaggagca atgcaagaca aaaaaatgtg     120
atctcaactg tatgtacatc catatatatg cctggagttc acttgacctg taaagtagta     180
gtaccaaatt ctgttgctga ccaattcatt ttaattatct taattccttg cataaaagaa     240
taaataattc agcagatgct tgctaaggaa ttaatgtgta atatatataa gcacaactaa     300
taaagcaatg gatactttca accaaaaaaa gtggtttaat ttgtctatag tagttctgtg     360
gaaatggaga acttaagaaa ggacaaaaag gaaataacca cttttggatc tatttgatgc     420
atggtatttc ttcaactcca ggggtatttt tgatatatgt atatatttag ggtataagct     480
aaatatgtac gcatattctc catatgaaag agtgcagtac tatttagcag cattctccat     540
atggatggtt agtactgaca ttgaagaatt ttgtagctag gactccatgt ttttttttat     600
cagtgataca gttgtacgtt gtcaattatt gatcatgaat tccagtttga tgtgacaatt     660
aatttgatga ttagtataac tagaaattaa cgatggatca atggacacct ggcccataat     720
taattaatta aattgtgata agattgtgtg tttgagtcac aaaaaacttt aagtggtgaa     780
tttgagaggt gtggtcaagc atgcaagttt cttacctagc cagggtgccg tcttttggct     840
tccacgcatc catctataga tctcagatgc acattatatt ctctgtgtgt atgggagaga     900
gagagagaga gaaagaaggg tttgcttggt acacactctc ctgatcaatc aggccatact     960
gtacagtgat cacacagtcc atgcatgcca gctctagtgc tgcatctacc tagaagctag    1020
catatgcttt ggttcaaact gtgcacacat cattcacaca tatttacatg ttactatatc    1080
ttacccaagg aagaggtact ctttgctgta ataacacatg tgattatgga aaaactgata    1140
aaatcattgt ccatacatat atttatgtat gacatgtttg aaaattgggt ttgagaagta    1200
ttatctcact cttttaaagga taagttttaa cctccaccgc accccatatt atcccgaccc    1260
tgcatctatt tttatttcac aatcacatcc tttgtaaccc attatcttga tatctcatac    1320
atattataca tgtattatat gtatatgaga aaatctttca tataaaaatt aaactactgc    1380
atgattatat atacgtgtta cgcgtatatg atcttggtca aatgtaacct caaggaaaca    1440
taaagttttg taagtcgtaa ctgcaggcgg tgaagtgtct agagctgatg gctggcggtg    1500
attcccatgc atgtctgggc atgcatggat cgatccatcg atgcctcgaa attcacgcaa    1560
gctctgcaac ggtttccgga tacagatggt cattgtcgtg tccttttttat ttttctcttt    1620
```

```
catttgcttt aattttcttc tctctgtttg gcttaacatg tgtggtacgt acactttgta    1680
acggatgtga gatgagcaat gcagtaagct taaggtagct agcgcgttgc agaatgcaga    1740
tcagagccac acatttactt tacttctcac ctgatcgatc gatcactgaa tgaagagagt    1800
ccaaagctag gcagcagttc ataacatgca tacgttgaca acgtacggac gcagctggca    1860
gctagctata tatttaatta agccttcata ctcaaagaat aacttttggg agctcttgaa    1920
tttctatcct tgcgttagct agatagatac gtcgaaaaaa ataactgcac ttttttagtg    1980
atacaatcca aagccagcaa aaaataataa attatatacg ctatttatga tggtaatata    2040
ttactgatac ataatccagc ccattttgct ctccatctaa ctttagatgt tcatatcaac    2100
cacttcggtt atattgcgga aattttgatt gaatgtatat atgtggcatt atagattata    2160
tctatgtctg aaaaatcata tcaccacata ttggttataa tgtgcgaaaa tatagaacaa    2220
aaaactgata ttgtcgatta gaggatgcca cctacaagct atagttttac atatattatt    2280
ttatgctgtc tactaaaaga acaataaaac catttactta caccactgca ttcaaacagt    2340
aaattggaga agttggcttt ctaccttgac actactagtc cttgctaaga taaaagtaaa    2400
acaacattac catcttatat caaatctact aattaaacca ctccatatta gatgaaatcc    2460
atgttaaaga gtctatatct atgcagtcgc tctcatgata tgtcattata tcttgatcta    2520
tctatgttaa tttagaagtt tacacccaca atcgctctaa ttttatagga ccatcgatga    2580
tatataatat ttttttcatc aggaatgaaa tagattacgt acacagttac attacgactc    2640 atgcacactag aactatatct atgtttagaa gtttatctag atatggcatg attaatagaa    2700
tgtatttgtg ttagagctct aagtttagaa tatgtgaccg ataaacctac cgttttattc    2760
tttttaacta catgttttgc aaaagattaa attgttatct tacaattcat atagcactag    2820
cattatgatc tggtgtatca tatatgtcat tatccatcta tgtttagaag tttatatcca    2880
cggctctaat tatgtggaac gattaaatga tgatatatat agttgttaag aggtatggaa    2940
tagattaaat aattagttac gttacgattc gtaacactag tgctatctat atttagaagt    3000
ttacatccac aatcgctcta attatgtggg attattaaac gatgaatata tttttctgtg    3060
aggaatgaat tgaaatagat taaatagtta cgttacgatt cgtaacatta gttctatcta    3120
tgtttagaag tttatctgga caatcaccat catgtcagtg tgccaatacg ctaaacttag    3180
aagatgcctc cgataatcgt agcattagta ttatttgggg aatgaattaa aaaatataaa    3240
taatgatata ttacaattga taatctatgt ttagaaactt ttgtcggtta ctcgctcaaa    3300
ttgtatgggg taataaatcg gtgaagtata cttttatact gaatggacaa gataagctac    3360
cattgatagc attagcggtt ctatttggta tattatcccg attatccacc ctcaatttgt    3420
gctaaaataa gattttttaca tcatcctagt caatatttgg ggttaccctg tctgcattat    3480
aatttatttt tgtgcttaac tataatatat acatacacta taatttatct aaataaaagt    3540
tctggtatga ttaaaaaaac taacaatttt gtgtgtggcg tattgagtgg aagaatgtca    3600
tgttaggatc acatgggaga gagtgcatgc gacgagatca tccttgttgg tctgtgcagg    3660
tggtgtgaaa tgtgatcaat atatatggtg gtgacagaga gagaaactaa cccaaaaaaa    3720
caaaaaaaga gagatgagag cgaatggatg gatgcaattg gcattaattt tcggtctttg    3780
ctgttctccc ccagccaggc cagtttgctt cacgcaatat tctaacccct tgagaaagag    3840
aagtgtactt gttgccaagg ccaattgcaa gcatttgcct tggctttaaa gtctcatcaa    3900
tacaacggca ccaaaaagaa aacacagaga tagaaaacca cctagtagct gatatacatt    3960
tatatatgac ctaaataaaa aaattccatt aatatgtata attccagcaa caacataaag    4020
```

```
aaataaaaat gcatttaaga aaacatagaa agaaataaaa ataaagtaaa taaagctagc    4080
taggcccaaa attggcagta attaagtagg gactagtata gaaatatatg gatatataca    4140
ccagcctcca ccaatgggat tgcaaacagc ctacttatca ctttgctgct gtatttacgc    4200
ttttgccctt cttccctcct atatgtacag ccgcccccac ctcattcctc cattcttact    4260
ccacacacac actctctctc tctctaccat ttgtgagaaa gaaatcgat tcagttctag     4320 agagagaaac aaacaatttt cgctgtctat ctctctcttg ctactagtcg gtcgatcttg    4380
agttagtttt aaccctacac aagccaaggt aacaacatct agcaggtagg agaagagagc    4440
tagagactag gtggtggggg ctcattccaa gaatgagctc gtcggtggtt gtgagcgcga    4500
gcggcagcgg cagcggcggc ggaggaggag gaggaggtgg cggcgccgga ggtgaggag    4560 gaggtgggcc gtgcggggcg tgcaagttct tgcggcggaa gtgcgtgcag gggtgcatct    4620
tcgcgcccta cttcgactcg gaggccgggg cggcgcactt cgcggcggtg cacaaggtgt    4680
tcggcgccag caacgtgtcc aagctgctgc agcagatccc ggcgcaccgc cgcctcgacg    4740
ccgtcgtcac catctgctac gaggcccagg cccgcctccg cgaccccgtc tacggctgcg    4800
tcgcccacat cttccacctc caacaccagg tatatactac tcatactcac tcgatctcct    4860
cctcctcatc gtcgccgtcg gtggcggcga gtcatttaga tgttcgtcat ggtggttgtg    4920
cgatcgatcg agcttctatt ttggttttgg ttttggtttt ggtttcttgg gtttgatttg    4980
gttggttttt ggaggaagga tggatgtctt tttcttgaag aaggcaaagg agtccttttt    5040
tggggaggag agaaggctag caagctaagc aagggagtta atctggagaa atggacttct    5100
ctctttctgt tactactcac tactactcag gcctaccagt gatgatgtgc acatctcatc    5160
atccatctca tcattaaatc ccatcatcta ctctctctct tgttcttgct ttctcttctt    5220
tcattctttc tctgaatctt ctgatagata gattgataga tagatgcatg atgatatccc    5280
catttatcac atcattttat atcatgcatc aggttgttgt ccccccccc cctctctctc     5340 tcttgctctg aaatcaagga gggtatgcat acatgcttgg atttcacacc cacaaaagaa    5400
aaatggtaat ttagcaagcc ctagctagga attaggatgc atcaatctct agtagttctt    5460
gaagctgcag ctagtatagc tcccaaccat ttctcctctt cctttctttt actaatatga    5520
tcagcatttc attaagattt ttttgtatat agtatagcta cctacatttt ctcttgatct    5580
gattatgcca agtactaatt ttctgtccat tttactgatg atgatctggt tcaattcccc    5640
atgtgtatat gtactctcag gtggcaggtc tccagtccga gctgaactac ctgcaaggtc    5700
acctctcgac gatggagctg ccgtcgccgc cgccctacgt cgccgggccg accctggcgc    5760
cgccacagcc acagccactg atgccgatga ccgccgccgc caacttcaac ttctccgacc    5820
tgccatcgtc gtcggcggcc aacattccgg tcaccgccga cctgtccacc ctctttgacc    5880
cactgccggc ggcgcagccg cagtggggac tataccagca gcagcaacac caccaccagc    5940
agctgcatca tcacccctat gaccggatgg gcgacggctc gtcgagcagc agaggcggcg    6000
acgacgatgg cagcgacggc ggcgacttgc aagcgctggc gagggagctt cttgaccgcc    6060
atggacggtc gtcgtcgagc tccaagctgg agccgccacc tcacacacag tgatcctcct    6120
cactgtgtgt gatcatcaat tcagcttagc tagctagctc atggactaat tgatcaggtg    6180
ttaatcattc atgaatgcat tggttgaggc aagaagagaa tttaatccca atggtgaaat    6240
ttttttcacc aaatcctcca tgtcgttgag gcgaaaaatc gaacgacgac gacgacgatg    6300
gcgaggaaga cgatgatggt gatgttgggg atggagatgg taggtaacag gcattgcccg    6360
```

```
gttttcgcgt atcatctttg ttcttgggct agggtgcaag gggtgcccac ttgcaccatt    6420
ttataatgct tgggagtttg ctccaaaaga ggaagcttgg ggatgagttc ttgttagctt    6480
agctgtagcc ctgatcactg ttccattgca acagttctaa ttgcaaaaaa caaaacctgg    6540
tctaatttag ttcaatatac aaaaaaaaaa tctttgtctc atcgcagatt aattacggtt    6600
gtgtttgaag tttgtttgat ttctgtttca aggttctaac tgaacatctg aagtgaagtg    6660
tagtcagtct taatttggga cttttctgatc tctctatgac aaatgagctt ttttttttg     6720 ccataatata tacaacagct agcaagtagc aaaatgagca ttttggggt taatggtaac     6780 tgaacatata tgtatggtgg caactgaata aagtgtgaac atatgtgagt acttggaggc    6840
tagagccagg tgttggtttc cttttacttg cttcgtgctt ctacaactac aataatgcaa    6900
gtattcatat ggtgcaacct tagtcttaga ttcagtctgg ctagctagct agctatttct    6960
aatgggacac agtacattta aaacaagcct aattaaacta gtttatttct ctatgaagag    7020
tcgtggtata tctggggcta aatgattggc aggggattat attttagagt ttgatatata    7080
gatgagtgag agacagacag gaagcatagc tttggtggga catctttgac taagaccatg    7140
cagcatgcac acaacaatgt tttctctcct tatgtttctt gaagttatat catatgccct    7200
tgtattcagg gactcctttg ttatcaattg ttggaaaatg acaagcggtt gggatatgaa    7260
taatatgatg ccataggaaa gtacatgttt cagtttagct agctctttaa tgtgtccaaa    7320
ccgcattgaa aagtttcatg attactacta gtccatgtag gtaactaatt attaccgtaa    7380
tgaacatgca tatgcatatg agttaatttt ggcatgtact ctaagctaat ttaagatgat    7440
gtttctgtgg cgaccggcca tgcgtgcaaa tacatggtac tatatatgca taataatagg    7500
gatactgcta ctagttaagt aagttaatta tgtgtctcta cattactctt tgattcgtta    7560
attaattaga caggtctttt ttttcttaag gaagatcgtc actaccgtaa attatcaaag    7620
cagggtaaat ttgacatgta actatggtaa gttagtaact attataacta gctggtacct    7680
agcatcaata atattccttg taacaatatt atttctgcaa cttttgcaca agtaagaata    7740
taaacattaa taggaaacaa gtattatttg tacaaactaa agaatgtaat aattagttgg    7800
atcattagta atgcatttaa ttagctttct tagaaataag agcattaatc aacagttgtc    7860
atatatgcaa tgaatcgtgt cattaatgtg tacattttgc gtgcaaggat cgcaaaagtt    7920
ccatatagct gttactattc tttgcaaatt tatcgtgcgt gatatcaaat gtattggatt    7980
ctcctactat tagaattgat acataagcga caccatcaca catgagaacg tcttttctta    8040
atatatataa gcacaagata ttagctagat gccaaattaa atacttgatt tccagcactt    8100
catagatatt agttaccttt ctcaagtttg gtgtgaaaaa aatgcatatc tatatatatt    8160
tgacagtatt ttagtagaat aatgtgagta gctagctgga aaagaatata tttctgcatg    8220
ctgcaaatat atggtaccaa ctgttcagtg ctaccctgaa ctgaagtaaa tgtcttatta    8280
atgaagagcc atcttatgtt gttttagaaa ttctatatgt agtgttggca ttgacttgat    8340
ttacacacta tagtgttata tatgcttgta gctgcacaaa agtagctttt agttgctggc    8400
atgtcaattt accaaacaga aaagagacg ttcaatttgt ggatgaaaaa aaaggaata     8460 tttttttaaag acgcaagttt aacacaattc aaaatgaagc ctttcgatgt tgagtttaag    8520
taatctttaa tttaaatata aagaataat ggtagtcagg gttaacactg cacaaaaaag     8580
tgaccttggt cctggtccta atgaagcggt ttccttaaaa cctgctagta accacctcac    8640
agttctcaat gctatgaaga aattaaaaag tcggttctaa atcaattaag gtaaatcatg    8700
gaagaatata gatgtcttac gaaagtaatc tgccccaata agcaatagta cagtggtcag    8760
```

-continued

```
tggagatcag agaaataatt ttgtgatatg gagtttaaac attggggtag cggaattaaa    8820
ctactatttg gtgtgaaatt atattaagta ggtcagaagc atccatacat agtacttctt    8880
ctgtcccaaa atataaagag tttcggttga atgggggcat atctaagtat tgcgagtttg    8940
gacaggctac atcccgcatg gaaaaaaatt gttgttttc ataccttttt gacaggcggg    9000
tgagccaacc acgtgaaaaa agttttttt tcgtagtgta tccagtagac tgacatgtta    9060
gcccaatggc gaaatcggcc ctagagcaaa taacgttgga ggcaatataa tggatcaaac    9120
agagatggtg tagcagctag ccgtgtgggg gccaagggct tttggaggcg gctattgcaa    9180
tttcggtttg aaatttcgga tcc                                            9203
```

<210> SEQ ID NO 35
<211> LENGTH: 6157
<212> TYPE: DNA
<213> ORGANISM: Artificial sequence
<220> FEATURE:
<223> OTHER INFORMATION: Vector pML18
<220> FEATURE:
<221> NAME/KEY: misc_feature
<222> LOCATION: (2549)..(2549)
<223> OTHER INFORMATION: n is a, c, g, or t

<400> SEQUENCE: 35

```
gaatatgcat cactagtaag ctttgctcta gactggaatt cgtcgactct agaggatcca      60
attccaatcc cacaaaaatc tgagcttaac agcacagttg ctcctctcag agcagaatcg    120
ggtattcaac accctcatat caactactac gttgtgtata acggtccaca tgccggtata    180
tacgatgact ggggttgtac aaaggcggca acaaacggcg ttcccggagt tgcacacaag    240
aaatttgcca ctattacaga ggcaagagca gcagctgacg cgtacacaac aagtcagcaa    300
acagacaggt tgaacttcat ccccaaagga gaagctcaac tcaagcccaa gagctttgct    360
aaggccctaa caagcccacc aaagcaaaaa gcccactggc tcacgctagg aaccaaaagg    420
cccagcagtg atccagcccc aaaagagatc tcctttgccc cggagattac aatggacgat    480
ttcctctatc tttacgatct aggaaggaag ttcgaaggtg aaggtgacga cactatgttc    540
accactgata atgagaaggt tagcctcttc aatttcagaa agaatgctga cccacagatg    600
gttagagagg cctacgcagc aggtctcatc aagacgatct acccgagtaa caatctccag    660
gagatcaaat accttcccaa gaaggttaaa gatgcagtca aaagattcag gactaattgc    720
atcaagaaca cagagaaaga catatttctc aagatcagaa gtactattcc agtatggacg    780
attcaaggct tgcttcataa accaaggcaa gtaatagaga ttggagtctc taaaaaggta    840
gttcctactg aatctaaggc catgcatgga gtctaagatt caaatcgagg atctaacaga    900
actcgccgtg aagactggcg aacagttcat acagagtctt ttacgactca atgacaagaa    960
gaaaatcttc gtcaacatgg tggagcacga cactctggtc tactccaaaa atgtcaaaga   1020
tacagtctca gaagaccaaa gggctattga cttttcaa caaggataaa tttcgggaaa    1080
cctcctcgga ttccattgcc cagctatctg tcacttcatc gaaaggacag tagaaaagga   1140
aggtggctcc tacaaatgcc atcattgcga taaaggaaag gctatcattc aagatgcctc   1200
tgccgacagt ggtcccaaag atggaccccc acccacgagg agcatcgtgg aaaaagaaga   1260
cgttccaacc acgtcttcaa agcaagtgga ttgatgtgac atctccactg acgtaaggga   1320
tgacgcacaa tcccactatc cttcgcaaga cccttcctct atataaggaa gttcatttca   1380
tttggagagg acacgctcga gctcatttct ctattacttc agccataaca aaagaactct   1440
```

```
tttctcttct tattaaacca tgaaaaagcc tgaactcacc gcgacgtctg tcgagaagtt    1500
tctgatcgaa aagttcgaca gcgtctccga cctgatgcag ctctcggagg gcgaagaatc    1560
tcgtgctttc agcttcgatg taggaggcg tggatatgtc ctgcgggtaa atagctgcgc    1620
cgatggtttc tacaaagatc gttatgttta tcggcacttt gcatcggccg cgctcccgat    1680
tccggaagtg cttgacattg gggaattcag cgagagcctg acctattgca tctcccgccg    1740
tgcacagggt gtcacgttgc aagacctgcc tgaaaccgaa ctgcccgctg ttctgcagcc    1800
ggtcgcggag gccatggatg cgatcgctgc ggccgatctt agccagacga gcgggttcgg    1860
cccattcgga ccgcaaggaa tcggtcaata cactacatgg cgtgatttca tatgcgcgat    1920
tgctgatccc catgtgtatc actggcaaac tgtgatggac gacaccgtca gtgcgtccgt    1980
cgcgcaggct ctcgatgagc tgatgctttg gccgaggac tgccccgaag tccggcacct    2040
cgtgcacgcg gatttcggct ccaacaatgt cctgacggac aatggccgca taacagcggt    2100
cattgactgg agcgaggcga tgttcgggga ttcccaatac gaggtcgcca acatcttctt    2160
ctggaggccg tggttggctt gtatggagca gcagacgcgc tacttcgagc ggaggcatcc    2220
ggagcttgca ggatcgccgc ggctccgggc gtatatgctc cgcattggtc ttgaccaact    2280
ctatcagagc ttggttgacg gcaatttcga tgatgcagct tgggcgcagg gtcgatgcga    2340
cgcaatcgtc cgatccggag ccgggactgt cgggcgtaca caaatcgccc gcagaagcgc    2400
ggccgtctgg accgatggct gtgtagaagt actcgccgat agtggaaacc gacgcccag    2460 cactcgtccg agggcaaagg aatagtgagg tacctaatag tgagatccaa cacttacgtt    2520
tgcaacgtcc aagagcaaat agaccacgna cgccggaagg ttgccgcagc gtgtggattg    2580
cgtctcaatt ctctcttgca ggaatgcaat gatgaatatg atactgacta tgaaactttg    2640
agggaatact gcctagcacc gtcacctcat aacgtgcatc atgcatgccc tgacaacatg    2700
gaacatcgct atttttctga agaattatgc tcgttggagg atgtcgcggc aattgcagct    2760
attgccaaca tcgaactacc cctcacgcat gcattcatca atattattca tgcggggaaa    2820
ggcaagatta tccaactgg caaatcatcc agcgtgattg gtaacttcag ttccagcgac    2880
ttgattcgtt ttggtgctac ccacgttttc aataaggacg agatggtgga gtaaagaagg    2940
agtgcgtcga agcagatcgt tcaaacattt ggcaataaag tttcttaaga ttgaatcctg    3000
ttgccggtct tgcgatgatt atcatataat ttctgttgaa ttacgttaag catgtaataa    3060
ttaacatgta atgcatgacg ttatttatga gatgggtttt tatgattaga gtcccgcaat    3120
tatacattta atacgcgata gaaaacaaaa tatagcgcgc aaactaggat aaattatcgc    3180
gcgcggtgtc atctatgtta ctagatcgat caaacttcgg tactgtgtaa tgacgatgag    3240
caatcgagag gctgactaac aaaaggtaca tcggtcgacg agctccctat agtgagtcgt    3300
attagaggcc gacttggcca aattcgtaat catggtcata gctgtttcct gtgtgaaatt    3360
gttatccgct cacaattcca cacaacatac gagccggaag cataaagtgt aaagcctggg    3420
gtgcctaatg agtgagctaa ctcacattaa ttgcgttgcg ctcactgccc gctttccagt    3480
cgggaaacct gtcgtgccag ctgcattaat gaatcggcca acgcgcgggg agaggcggtt    3540
tgcgtattgg gcgctcttcc gcttcctcgc tcactgactc gctgcgctcg tcgttcggc    3600 tgcggcgagc ggtatcagct cactcaaagg cggtaatacg ttatccaca gaatcagggg    3660 ataacgcagg aaagaacatg tgagcaaaag gccagcaaaa ggccaggaac cgtaaaaagg    3720
ccgcgttgct ggcgtttttc cataggctcc gcccccctga cgagcatcac aaaaatcgac    3780
gctcaagtca gaggtggcga aacccgacag gactataaag ataccaggcg tttccccctg    3840
```

```
gaagctccct cgtgcgctct cctgttccga ccctgccgct taccggatac ctgtccgcct   3900
ttctcccttc gggaagcgtg gcgctttctc atagctcacg ctgtaggtat ctcagttcgg   3960
tgtaggtcgt tcgctccaag ctgggctgtg tgcacgaacc ccccgttcag cccgaccgct   4020
gcgccttatc cggtaactat cgtcttgagt ccaacccggt aagacacgac ttatcgccac   4080
tggcagcagc cactggtaac aggattagca gagcgaggta tgtaggcggt gctacagagt   4140
tcttgaagtg gtggcctaac tacggctaca ctagaaggac agtatttggt atctgcgctc   4200
tgctgaagcc agttaccttc ggaaaaagag ttggtagctc ttgatccggc aaacaaacca   4260
ccgctggtag cggtggtttt tttgtttgca agcagcagat tacgcgcaga aaaaaggat    4320 ctcaagaaga tcctttgatc ttttctacgg ggtctgacgc tcagtggaac gaaaactcac   4380
gttaagggat tttggtcatg agattatcaa aaaggatctt cacctagatc cttttaaatt   4440
aaaaatgaag ttttaaatca atctaaagta tatatgagta aacttggtct gacagttacc   4500
aatgcttaat cagtgaggca cctatctcag cgatctgtct atttcgttca tccatagttg   4560
cctgactccc cgtcgtgtag ataactacga tacgggaggg cttaccatct ggccccagtg   4620
ctgcaatgat accgcgagac ccacgctcac cggctccaga tttatcagca ataaaccagc   4680
cagccggaag ggccgagcgc agaagtggtc ctgcaacttt atccgcctcc atccagtcta   4740
ttaattgttg ccgggaagct agagtaagta gttcgccagt taatagtttg cgcaacgttg   4800
ttgccattgc tacaggcatc gtggtgtcac gctcgtcgtt tggtatggct tcattcagct   4860
ccggttccca acgatcaagg cgagttacat gatcccccat gttgtgcaaa aaagcggtta   4920
gctccttcgg tcctccgatc gttgtcagaa gtaagttggc cgcagtgtta tcactcatgg   4980
ttatggcagc actgcataat tctcttactg tcatgccatc cgtaagatgc ttttctgtga   5040
ctggtgagta ctcaaccaag tcattctgag aatagtgtat gcggcgaccg agttgctctt   5100
gcccggcgtc aatacgggat aataccgcgc cacatagcag aactttaaaa gtgctcatca   5160
ttggaaaacg ttcttcgggg cgaaaactct caaggatctt accgctgttg agatccagtt   5220
cgatgtaacc cactcgtgca cccaactgat cttcagcatc ttttactttc accagcgttt   5280
ctgggtgagc aaaaacagga aggcaaaatg ccgcaaaaaa gggaataagg gcgacacgga   5340
aatgttgaat actcatactc ttcctttttc aatattattg aagcatttat cagggttatt   5400
gtctcatgag cggatacata tttgaatgta tttagaaaaa taaacaaata ggggttccgc   5460
gcacatttcc ccgaaaagtg ccacctgacg cgcctgtag cggcgcatta agcgcggcgg    5520
gtgtggtggt tacgcgcagc gtgaccgcta cacttgccag cgccctagcg cccgctcctt   5580
tcgctttctt cccttccttt ctcgccacgt tcgccggctt tccccgtcaa gctctaaatc   5640
ggggcatccc tttagggttc cgatttagtg ctttacggca cctcgacccc aaaaaacttg   5700
attagggtga tggttcacgt agtgggccat cgccctgata cggttttt cgccctttga     5760 cgttggagtc cacgttcttt aatagtggac tcttgttcca aactggaaca cactcaacc    5820 ctatctcggt ctattctttt gatttataag ggattttgcc gatttcggcc tattggttaa   5880
aaaatgagct gatttaacaa aaatttaacg cgaatttaa caaatatta acaaatatt      5940 aacgttaca atttcccatt cgccattcag gctgcgcaac tgttgggaag ggcgatcggt    6000
gcgggcctct tcgctattac gccagctggc gaaagggga tgtgctgcaa ggcgattaag    6060
ttgggtaacg ccagggtttt cccagtcacg acgttgtaaa acgacggcca gtgccaagct   6120
gacttggtca gcggccgcag atttaggtga cactata                            6157
```

<210> SEQ ID NO 36
<211> LENGTH: 1130
<212> TYPE: DNA
<213> ORGANISM: Zea mays
<220> FEATURE:
<221> NAME/KEY: misc_feature
<223> OTHER INFORMATION: cef1f.pk001.f4:fis

<400> SEQUENCE: 36

```
cggcaggcac gcacgcaggg agagagatag ataaaaggtc gccccttga ggacagggca    60
gggcagctga gggcaatgag cgctggcgga ggcggcggcg gcaccagcac gcttggcggc   120
gggggcccga gcggcagcgg cagcggaggc cctggaggaa gcggcggcgg cgggccttgc   180
ggcgcgtgca agttcctccg gcgcaagtgc gtcagcggct gcatcttcgc gccctacttc   240
gactcggagc agggcgcggc gcacttcgcg gccgtgcaca aggtgttcgg cgccagcaac   300
gtgtccaagc tgctgctcca gatcccggcg cacaagcgcc tcgacgccgt cgtcaccatc   360
tgctacgagg cccaggcgcg gctccgcgac cccgtctacg gctgcgtcgc ccacatcttc   420
gcgctccagc agcaggtggt gaatctccag gccgagctga cctacctgca agcacacctc   480
gccacgctcg agctgccggc cccgcccccg ctgccggccc cgccgcagat gcccatgcca   540
ggcccgttct ccatctcgga cctgccgttg tcgaccagcg tccccaccac cgtcgacctg   600
tccgcgctct tcgacccgcc accaccgcag tgggcgacgg cgcagcagcc gcaccaccac   660
catcaacagc cgccgcagca ccaccagctc cggcaaccgg cgccgtatgg cgctggcgcg   720
tccgtcaggt ccggcggcgt gaagctcgag cacccgccgc cacactcaag atgagctgga   780
tgggggagta gaaggatcaa aaacccgtgc agaacaaggt gagagttggc gcccggcagt   840
atcgagggag atagggggtcg gtgacgggcg atgtccagca cagcaggagt aggtaagcag   900
cattggccgg ttttcgcgta cccagcaccc ctgttgttaa tcggctgggg tgcaatggcg   960
gcgcccactt gcttgatata ttctccagtt tgatcatatt tgctccaaga caaagaaag   1020
agtgctgggg atcgacgaga gtattactag aattgacatg tattagtaaa aaaaaaaaa  1080
aaaaaaaaaa aaaaaaaaaa aaaaaaaaaa aaaaaaaaa aaaaaaaaaa              1130
```

<210> SEQ ID NO 37
<211> LENGTH: 232
<212> TYPE: PRT
<213> ORGANISM: Zea mays
<220> FEATURE:
<221> NAME/KEY: MISC_FEATURE
<223> OTHER INFORMATION: cef1f.pk001.f4:fis

<400> SEQUENCE: 37

```
Met Ser Ala Gly Gly Gly Gly Gly Thr Ser Thr Leu Gly Gly Gly
1               5                   10                  15

Gly Pro Ser Gly Ser Gly Ser Gly Gly Pro Gly Gly Ser Gly Gly Gly
            20                  25                  30

Gly Pro Cys Gly Ala Cys Lys Phe Leu Arg Arg Lys Cys Val Ser Gly
        35                  40                  45

Cys Ile Phe Ala Pro Tyr Phe Asp Ser Glu Gln Gly Ala Ala His Phe
    50                  55                  60

Ala Ala Val His Lys Val Phe Gly Ala Ser Asn Val Ser Lys Leu Leu
65                  70                  75                  80

Leu Gln Ile Pro Ala His Lys Arg Leu Asp Ala Val Val Thr Ile Cys
                85                  90                  95

Tyr Glu Ala Gln Ala Arg Leu Arg Asp Pro Val Tyr Gly Cys Val Ala
```

```
              100                 105                 110
His Ile Phe Ala Leu Gln Gln Val Val Asn Leu Gln Ala Glu Leu
        115                 120                 125
Thr Tyr Leu Gln Ala His Leu Ala Thr Leu Glu Leu Pro Ala Pro
130                 135                 140
Pro Leu Pro Ala Pro Pro Gln Met Pro Met Pro Gly Pro Phe Ser Ile
145                 150                 155                 160
Ser Asp Leu Pro Leu Ser Thr Ser Val Pro Thr Val Asp Leu Ser
                165                 170                 175
Ala Leu Phe Asp Pro Pro Pro Gln Trp Ala Thr Ala Gln Gln Pro
        180                 185                 190
His His His His Gln Gln Pro Pro Gln His His Gln Leu Arg Gln Pro
        195                 200                 205
Ala Pro Tyr Gly Ala Gly Ala Ser Val Arg Ser Gly Gly Val Lys Leu
210                 215                 220
Glu His Pro Pro Pro His Ser Arg
225                 230

<210> SEQ ID NO 38
<211> LENGTH: 1038
<212> TYPE: DNA
<213> ORGANISM: Zea mays
<220> FEATURE:
<221> NAME/KEY: misc_feature
<223> OTHER INFORMATION: cpf1c.pk006.d18a:fis

<400> SEQUENCE: 38
agaagcaggg cgcaagtcct accatagcaa tatagcatag ctagcacacc agtagctagc      60
atcggagacg atctatcgac tagctctcta tagctagtta gctcttccct tgctagccgt     120
ttgcgccggt gactgacgac gaccgacgac atggccaacg aaggggccgc cgctgccgct     180
gccgctgccg ctgctgctgc cgcgacgggc gcggggtctc cgtgcggcgc gtgcaagttc     240
ctgcgccggc ggtgcgtgcc ggagtgcgtg ttcgcgccct acttcagcag cgaccagggc     300
gccgcgcgct cgccgccat ccacaaggtg ttcggcgcca gcaacgcctc caagctgctg     360
tcccacctcc ccgtggccga ccgctgcgag ccgtcgtca ccatcaccta cgaggcgcag     420
gccaggctcc gggaccccgt ctacggctgc gtcgcccaga tcttcgccct ccagcagcag     480
gtcgccatcc tgcaagcgca gctgatgcag gccaaggcgc agctggcgtg cggcgtccag     540
ggcgccgccg cgcactcgcc ggcgagccac caccaccacc agtggccgga cagcgccagc     600
atcagcgccc tgctccgcca ggacgcggcg tgtagcgcca ggaggcccgg cgggcccctc     660
gacgacttct tcactccgga gctcgtggcc gggttcaggg acgacgtcgc cgccgccgcc     720
gggcagcatt gcgcaggcaa ggtggatgcc ggagagctcc agtacctggc ccaggccatg     780
atgaggagcc ccaactactc cctgtagccg tagctgtagc tgcctaggaa ggatgatgag     840
aatcagacac catgcgtttt ggagccatgc catgctgtgc catctcatct cgatctccac     900
tccgctaatg caagtgttga gagatgagct agaaattcct gcaaaggaa gataacaact      960
tgtaccagct agtgatgaag tactctcctt gtctctctca aaaaaaaaaa aaaaaaaaaa    1020
aaaaaaaaaa aaaaaaaa                                                  1038

<210> SEQ ID NO 39
<211> LENGTH: 218
<212> TYPE: PRT
<213> ORGANISM: Zea mays
<220> FEATURE:
```

<221> NAME/KEY: MISC_FEATURE
<223> OTHER INFORMATION: cpf1c.pk006.d18a:fis

<400> SEQUENCE: 39

```
Met Ala Asn Glu Gly Ala Ala Ala Ala Ala Ala Ala Ala Ala Ala
1               5                   10                  15

Ala Ala Thr Gly Ala Gly Ser Pro Cys Gly Ala Cys Lys Phe Leu Arg
            20                  25                  30

Arg Arg Cys Val Pro Glu Cys Val Phe Ala Pro Tyr Phe Ser Ser Asp
            35                  40                  45

Gln Gly Ala Ala Arg Phe Ala Ile His Lys Val Phe Gly Ala Ser
    50                  55                  60

Asn Ala Ser Lys Leu Leu Ser His Leu Pro Val Ala Asp Arg Cys Glu
65                  70                  75                  80

Ala Val Val Thr Ile Thr Tyr Glu Ala Gln Ala Arg Leu Arg Asp Pro
                85                  90                  95

Val Tyr Gly Cys Val Ala Gln Ile Phe Ala Leu Gln Gln Gln Val Ala
                100                 105                 110

Ile Leu Gln Ala Gln Leu Met Gln Ala Lys Ala Gln Leu Ala Cys Gly
            115                 120                 125

Val Gln Gly Ala Ala Ala His Ser Pro Ala Ser His His His His Gln
    130                 135                 140

Trp Pro Asp Ser Ala Ser Ile Ser Ala Leu Leu Arg Gln Asp Ala Ala
145                 150                 155                 160

Cys Ser Ala Arg Arg Pro Gly Gly Pro Leu Asp Asp Phe Phe Thr Pro
                165                 170                 175

Glu Leu Val Ala Gly Phe Arg Asp Asp Val Ala Ala Ala Gly Gln
            180                 185                 190

His Cys Ala Gly Lys Val Asp Ala Gly Glu Leu Gln Tyr Leu Ala Gln
        195                 200                 205

Ala Met Met Arg Ser Pro Asn Tyr Ser Leu
    210                 215
```

<210> SEQ ID NO 40
<211> LENGTH: 1262
<212> TYPE: DNA
<213> ORGANISM: Zea mays
<220> FEATURE:
<221> NAME/KEY: misc_feature
<223> OTHER INFORMATION: cpi1c.pk005.a12:fis

<400> SEQUENCE: 40

```
gcggcacgca cgcacgctcg cagggagaga gatagataaa aggtcgcccc cttgagggca      60
gggcagggca gctgagggca atgagcgctg gcggcggcag cagcacgctt ggcggcgggg     120
ggccgagcgg cagcagcagc ggaggccctg gaggaagcgg cggcggcggc gggccttgcg     180
gcgcgtgcaa gttcctccgg cgcaagtgcg tcagcggctg catcttcgcg ccctacttcg     240
actcggagca gggcgcggcg cacttcgcgg ccgtgcacaa ggtgttcggc gccagcaacg     300
tgtccaagct gctgctccag atcccggcgc acaagcgcct cgacgccgtc gtcaccatct     360
gctacgaggc ccaggcgcgg ctccgcgacc ccgtctacgg ctgcgtcgcc cacatcttcg     420
cgctccagca gcaggtggtg aatctccagg ccgagctgac ctacctgcaa gcacacctcg     480
ccacgctcga gctgccggcc cgcccccgc tgccggcccc gccgcagatg cccatgccag     540
gcccgttctc catctcggac ctgccgttgt cgaccagcgt ccccaccacc gtcgacctgt     600
ccgcgctctt cgacccgcca ccaccgcagt gggcgacggc gcagcagccg caccaccacc     660
```

-continued

```
atcaacagcc gccgcagcac caccagctcc ggcaaccggc gccgtatggc gctggcgcgt    720
ccgtcaggcc cggcggcggc cccggcatgg cagagagctc aggcggagac gagctgcagt    780
cgctggcgag ggagctcctg gaccgccacc ggtccggcgg cgtgaagctc gagcacccgc    840
cgccacactc aagatgagct ggatggggga gtagaaggat caaaaacccg tgcagaacaa    900
ggtgagagtt ggcgcccggc agtatcgagg gagataggggg tcggtgacgg gcgatgtcca    960
gcacagcagg agtaggtaag cagcattggc cggttttcgc gtacccagca ccctgttgt    1020
taatcggctg gggtgcaatg gcggcgccca cttgcttgat atattctcca gtttgatcat    1080
atttgctcca agacaaaaga aagagtgctg gggatcgacg agagtattac tagaattgac    1140
atgtattagt aacattattg ttacctttga taccgttcca ttagttgcaa gattttatt    1200
aagaaaagaa tctcaacatg gtttctaaaa aaaaaaaaaa aaaaaaaaa aaaaaaaaa    1260
aa                                                                1262
```

<210> SEQ ID NO 41
<211> LENGTH: 258
<212> TYPE: PRT
<213> ORGANISM: Zea mays
<220> FEATURE:
<221> NAME/KEY: MISC_FEATURE
<223> OTHER INFORMATION: cpi1c.pk005.a12:fis

<400> SEQUENCE: 41

```
Met Ser Ala Gly Gly Gly Ser Ser Thr Leu Gly Gly Gly Gly Pro Ser
1               5                  10                  15

Gly Ser Ser Ser Gly Gly Pro Gly Gly Ser Gly Gly Gly Gly Gly Pro
            20                  25                  30

Cys Gly Ala Cys Lys Phe Leu Arg Arg Lys Cys Val Ser Gly Cys Ile
        35                  40                  45

Phe Ala Pro Tyr Phe Asp Ser Glu Gln Gly Ala Ala His Phe Ala Ala
    50                  55                  60

Val His Lys Val Phe Gly Ala Ser Asn Val Ser Lys Leu Leu Leu Gln
65                  70                  75                  80

Ile Pro Ala His Lys Arg Leu Asp Ala Val Val Thr Ile Cys Tyr Glu
                85                  90                  95

Ala Gln Ala Arg Leu Arg Asp Pro Val Tyr Gly Cys Val Ala His Ile
            100                 105                 110

Phe Ala Leu Gln Gln Gln Val Val Asn Leu Gln Ala Glu Leu Thr Tyr
        115                 120                 125

Leu Gln Ala His Leu Ala Thr Leu Glu Leu Pro Ala Pro Pro Leu
    130                 135                 140

Pro Ala Pro Pro Gln Met Pro Met Pro Gly Pro Phe Ser Ile Ser Asp
145                 150                 155                 160

Leu Pro Leu Ser Thr Ser Val Pro Thr Thr Val Asp Leu Ser Ala Leu
                165                 170                 175

Phe Asp Pro Pro Pro Gln Trp Ala Thr Ala Gln Pro His His
            180                 185                 190

His His Gln Gln Pro Pro Gln His His Gln Leu Arg Gln Pro Ala Pro
        195                 200                 205

Tyr Gly Ala Gly Ala Ser Val Arg Pro Gly Gly Pro Gly Met Ala
    210                 215                 220

Glu Ser Ser Gly Gly Asp Glu Leu Gln Ser Leu Ala Arg Glu Leu Leu
225                 230                 235                 240
```

```
Asp Arg His Arg Ser Gly Gly Val Lys Leu Glu His Pro Pro Pro His
                245                 250                 255

Ser Arg

<210> SEQ ID NO 42
<211> LENGTH: 977
<212> TYPE: DNA
<213> ORGANISM: Zea mays
<220> FEATURE:
<221> NAME/KEY: misc_feature
<223> OTHER INFORMATION: cr1n.pk0028.h3a:fis

<400> SEQUENCE: 42
gcaacttgca gtaggtgaca ggtgttaaca ggagctggct gagcttctct tgcttctgca      60
agtagtagct gtagccgccc tgtaggcaga gagaggagag acgacgtacg tgagggagcg     120
agcgagcgac gacagcatca ggcaggcgtt gacggccatg gcttcctccg gcagcggtgg     180
cggctcgccg gggtccccgt gtggcgcctg caagttcctg cggcgcaagt gcgcggcgga     240
gtgcgtgttc gctccccact tctgcgccga ggacggggcg gcgcagttcg cggccatcca     300
caaggtgttc ggcgccagca acgcggccaa gctgctgcag caggtggccc ccgccgaccg     360
gagcgaggcg gcggccaccg tcacctacga ggcgcaggcc aggctgcgcg accccatcta     420
cggctgcgtc gcccacatct cgcgctgca gcaacaggtg gcgagcttgc agatgcaggt     480
gctgcaggcg aaggcgcagg tggcgcagac gatggcggcg gccgggccgc aggggggcag     540
cagccctctc ctgcagcggt ggccgctgga gcctgagtcg ctgtcgacgc agagctccgg     600
gtgctacagc gacatgtact gcggcttcgg cgaccaggag aaggcagct acacgagatg     660 aataatgaat ggatcattcg cgcgcgcgcg cgcacgcatc gacacagata ctttcttcta     720
ttagcgccaa gagacaacaa caaccgaggg cctcaacttt cttgttggtt tgcagtgcgt     780
tttgttcagt tcagcagcta gctctccggt ttggggagga gcttaatttc gatgagattt     840
cgtgcgatcc ataaacttgt atttcttgcc ggttcgagct gtaaaatgga agtgcagctc     900
atcatcatgt gtgtggttat taaacggagg cacaaatcga ggataatttc atattcccta     960
aaaaaaaaaa aaaaaaa                                                     977

<210> SEQ ID NO 43
<211> LENGTH: 167
<212> TYPE: PRT
<213> ORGANISM: Zea mays
<220> FEATURE:
<221> NAME/KEY: MISC_FEATURE
<223> OTHER INFORMATION: cr1n.pk0028.h3a:fis

<400> SEQUENCE: 43

Met Ala Ser Ser Gly Ser Gly Gly Gly Ser Pro Gly Ser Pro Cys Gly
1               5                   10                  15

Ala Cys Lys Phe Leu Arg Arg Lys Cys Ala Ala Glu Cys Val Phe Ala
                20                  25                  30

Pro His Phe Cys Ala Glu Asp Gly Ala Ala Gln Phe Ala Ala Ile His
            35                  40                  45

Lys Val Phe Gly Ala Ser Asn Ala Ala Lys Leu Leu Gln Gln Val Ala
        50                  55                  60

Pro Ala Asp Arg Ser Glu Ala Ala Ala Thr Val Thr Tyr Glu Ala Gln
65                  70                  75                  80

Ala Arg Leu Arg Asp Pro Ile Tyr Gly Cys Val Ala His Ile Phe Ala
                85                  90                  95
```

```
Leu Gln Gln Gln Val Ala Ser Leu Gln Met Gln Val Leu Gln Ala Lys
                100                 105                 110

Ala Gln Val Ala Gln Thr Met Ala Ala Gly Pro Gln Gly Gly Ser
        115                 120                 125

Ser Pro Leu Leu Gln Arg Trp Pro Leu Glu Pro Glu Ser Leu Ser Thr
    130                 135                 140

Gln Ser Ser Gly Cys Tyr Ser Asp Met Tyr Cys Gly Phe Gly Asp Gln
145                 150                 155                 160

Glu Glu Gly Ser Tyr Thr Arg
                165

<210> SEQ ID NO 44
<211> LENGTH: 1058
<212> TYPE: DNA
<213> ORGANISM: Euphorbia lagascae
<220> FEATURE:
<221> NAME/KEY: misc_feature
<223> OTHER INFORMATION: eel1c.pk003.b10:fis

<400> SEQUENCE: 44
gcttcttctt catattctgc gtctcataaa ccctaattat gctctcttct ctctccaaat      60
tcgatccgaa atgagttcga cggtgcatcc tagcagcagc ggcagcagcg gcggagccgg     120
aggaggagga agtggtggaa gtggcggagg gagtgggccg tgtggagcgt gtaaattttt     180
gaggagaaaa tgtgtgccgg ggtgtatatt tgcgccgtac tttgattccg agcagggagc     240
ggcgcatttt gcggcggtgc ataaggtttt tggtgcgagt aacgtttcga aacttcttct     300
gcatattccg gtacataaac gccttgatgc ggtggttact atttgttatg aagctcaagc     360
tcggcttcga gatcctgttt atggctgcgt tgctcatata ttcgctctgc aacaacaggt     420
ggtgaactta caggcagagc tcacatattt gcaagcccat ttagcaacac tagagcttcc     480
gtcaccaccg ccgcctcctc tcccaccaca aacactattg acaccaccac ctctatcaat     540
atccgacctc ccatcatcct cttctgctcc cggttcatat gacttgcaat cgcttttga     600 tccgatggca caaaattcat ggtcaatgca acaaaggcta atagatccac gccatcaatt     660
cataggttcg actagtggtt catcgtcgtt aaccaccaca ggcagtggga gtggtgatct     720
tcatacattg gcacgtgagc ttctccatag acatggttct ccgtcacatg gttcaatgcc     780
atgtagcggc gctttatctt catctccgtc ttctatctca aaatgaaact gaccctattg     840
atagaagttg ttgcaacata atttgtacta attttcaatg ggatgctagc cgaaagagct     900
taagttttca tggtatttta gtttagagat ctagtgtttt aataactggt cactaatttt     960
tttggccttc tgtttattat attattcatt ttctcttaaa aaaaaaaaa aaaaaaaaa    1020 aaaaaaaaa aaaaaaaaa aaaaaaaaa aaaaaaa                              1058

<210> SEQ ID NO 45
<211> LENGTH: 251
<212> TYPE: PRT
<213> ORGANISM: Euphorbia lagascae
<220> FEATURE:
<221> NAME/KEY: MISC_FEATURE
<223> OTHER INFORMATION: eel1c.pk003.b10:fis

<400> SEQUENCE: 45

Met Ser Ser Thr Val His Pro Ser Ser Ser Gly Ser Ser Gly Gly Ala
1               5                   10                  15

Gly Gly Gly Gly Ser Gly Gly Ser Gly Gly Gly Ser Gly Pro Cys Gly
            20                  25                  30
```

```
Ala Cys Lys Phe Leu Arg Arg Lys Cys Val Pro Gly Cys Ile Phe Ala
        35                  40                  45

Pro Tyr Phe Asp Ser Glu Gln Gly Ala Ala His Phe Ala Ala Val His
 50                  55                  60

Lys Val Phe Gly Ala Ser Asn Val Ser Lys Leu Leu His Ile Pro
 65                  70                  75                  80

Val His Lys Arg Leu Asp Ala Val Val Thr Ile Cys Tyr Glu Ala Gln
                85                  90                  95

Ala Arg Leu Arg Asp Pro Val Tyr Gly Cys Val Ala His Ile Phe Ala
        100                 105                 110

Leu Gln Gln Gln Val Val Asn Leu Gln Ala Glu Leu Thr Tyr Leu Gln
        115                 120                 125

Ala His Leu Ala Thr Leu Glu Leu Pro Ser Pro Pro Pro Pro Pro Leu
    130                 135                 140

Pro Pro Gln Thr Leu Leu Thr Pro Pro Leu Ser Ile Ser Asp Leu
145                 150                 155                 160

Pro Ser Ser Ser Ser Ala Pro Gly Ser Tyr Asp Leu Gln Ser Leu Phe
                165                 170                 175

Asp Pro Met Ala Gln Asn Ser Trp Ser Met Gln Gln Arg Leu Ile Asp
            180                 185                 190

Pro Arg His Gln Phe Ile Gly Ser Thr Ser Gly Ser Ser Ser Leu Thr
        195                 200                 205

Thr Thr Gly Ser Gly Ser Gly Asp Leu His Thr Leu Ala Arg Glu Leu
    210                 215                 220

Leu His Arg His Gly Ser Pro Ser His Gly Ser Met Pro Cys Ser Gly
225                 230                 235                 240

Ala Leu Ser Ser Ser Pro Ser Ser Ile Ser Lys
                245                 250

<210> SEQ ID NO 46
<211> LENGTH: 484
<212> TYPE: DNA
<213> ORGANISM: Aquilegia vulgaris
<220> FEATURE:
<221> NAME/KEY: misc_feature
<223> OTHER INFORMATION: eav1c.pk003.c9
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
```

-continued

```
<400> SEQUENCE: 46
gcganagtgc gttgttggnt gtattttcgc cccatatttt gattcagaac aaggtgcaac    60
acactttgca gctgttcata aggtgtttgg tgcaagtaat gtgtccaagc ttctttttaca   120 cataccctgtt cataagcgtt tggatgcagt tgttactatt tgttatgaag ctcaagcacg   180
tttaagagat ccagtttatg ggtgtgttgc taatatcttt gctcttcaac aacaggtggg   240
aaatttacaa gctgagttat cctacttgca aacatatccta gcatcattgg gngcttccaa   300
ctccaccanc aagctccgcc aacaccaatg cttattacaa caacacctct ctccaaaagc   360 aaatttttcca tcaagcttcc actaagncan gcaaaacttt tgacttggtc aactcctttt   420
cganccccca aaggaacaaa tcggggggaca cttcaacaaa agacaaatgg attttttaaac  480 aaat                                                                 484

<210> SEQ ID NO 47
<211> LENGTH: 127
<212> TYPE: PRT
<213> ORGANISM: Aquilegia vulgaris
<220> FEATURE:
<221> NAME/KEY: MISC_FEATURE
<223> OTHER INFORMATION: eav1c.pk003.c9
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid

<400> SEQUENCE: 47

Arg Xaa Cys Val Val Gly Cys Ile Phe Ala Pro Tyr Phe Asp Ser Glu
 1               5                  10                  15

Gln Gly Ala Thr His Phe Ala Ala Val His Lys Val Phe Gly Ala Ser
            20                  25                  30

Asn Val Ser Lys Leu Leu Leu His Ile Pro Val His Lys Arg Leu Asp
        35                  40                  45

Ala Val Val Thr Ile Cys Tyr Glu Ala Gln Ala Arg Leu Arg Asp Pro
    50                  55                  60

Val Tyr Gly Cys Val Ala Asn Ile Phe Ala Leu Gln Gln Gln Val Gly
65                  70                  75                  80

Asn Leu Gln Ala Glu Leu Ser Tyr Leu Gln Thr Tyr Leu Ala Ser Leu
                85                  90                  95

Gly Ala Ser Asn Ser Thr Xaa Lys Leu Arg Gln His Gln Cys Leu Leu
            100                 105                 110

Gln Gln His Leu Ser Pro Lys Ala Asn Phe Pro Ser Ser Phe His
        115                 120                 125

<210> SEQ ID NO 48
<211> LENGTH: 1077
<212> TYPE: DNA
<213> ORGANISM: Cyamopsis tetragonoloba
<220> FEATURE:
<221> NAME/KEY: misc_feature
<223> OTHER INFORMATION: lds3c.pk011.j11:fis

<400> SEQUENCE: 48
gacaacacat cttgctctca catgatacag gtagagagag aaagttgaaa ggatgatgag    60
ttgtgttgca taaattgacg aggaaggagt agcgagggca aaaaggaat taaatttaaa   120 gattaagatt cagttaaggt ggaagatgag ttcgaaagct ggaaatggaa gtggaagtgg   180
```

```
aagtggcagt ggaggcggga gcccttgtgg ggcttgtaag tttcttcgaa ggaagtgtgt    240
ggcaggatgt gtgtttgctc catactttga ctcagagcaa ggagccactc attttgcagc    300
tgtgcataag gtgtttggtg caagcaacgt ttctaaactt ctcctcaacc ttccgctcaa    360
caaaaggctt gatgctgtta ttaccatttg ctatgaagct cagtcaagga tcagagatcc    420
cgtcttcggc tgcgttgctc acatctttgc tctccagcaa caggtggtaa gtttacaaac    480
agaagtgtcg tacttacaaa gccaccttgc tgcaatggag ttacctcagc caccacctcc    540
tcctcctcca caggagacag tggtgcaggc accggtattc tcgattgcag acataccggc    600
agcaacggta gcgggcatgc cggcgagcta tgacctgtct tcactttttg agccgacggg    660
gcaacaaaat tcatgggggg gcggcggcat agacccgcgt caattttttgg cagttggccc    720 atcatcaact actgatgctg atctccaagc aatggcacgt gacctttctg aaagacttgc    780
ctctctacct ccacctgcac ccgcacctgc atttgctcct ctacctccac ttccacctgc    840
acctgcacct gcacctgcac catcatgccc caatgcacct catctttat cactttctta    900 attaatcatc atcatcatca tacatgcatc tatcttcaga cttttcttca ctttttattt    960
tcatcgaaaa ctagtcaggg atcttcaatt tcgtacacgc tctaatttat gtgcgtgcgg   1020
atatttcttt taattttcgc gcttctgcct ttcaaaaaaa aaaaaaaaaa aaaaaaa     1077
```

<210> SEQ ID NO 49
<211> LENGTH: 251
<212> TYPE: PRT
<213> ORGANISM: Cyamopsis tetragonoloba
<220> FEATURE:
<221> NAME/KEY: MISC_FEATURE
<223> OTHER INFORMATION: lds3c.pk011.j11:fis

<400> SEQUENCE: 49

```
Met Ser Ser Lys Ala Gly Asn Gly Ser Gly Ser Gly Ser Gly
1               5                   10                  15

Gly Gly Ser Pro Cys Gly Ala Cys Lys Phe Leu Arg Arg Lys Cys Val
            20                  25                  30

Ala Gly Cys Val Phe Ala Pro Tyr Phe Asp Ser Glu Gln Gly Ala Thr
        35                  40                  45

His Phe Ala Ala Val His Lys Val Phe Gly Ala Ser Asn Val Ser Lys
    50                  55                  60

Leu Leu Leu Asn Leu Pro Leu Asn Lys Arg Leu Asp Ala Val Ile Thr
65                  70                  75                  80

Ile Cys Tyr Glu Ala Gln Ser Arg Ile Arg Asp Pro Val Phe Gly Cys
                85                  90                  95

Val Ala His Ile Phe Ala Leu Gln Gln Gln Val Val Ser Leu Gln Thr
            100                 105                 110

Glu Val Ser Tyr Leu Gln Ser His Leu Ala Ala Met Glu Leu Pro Gln
        115                 120                 125

Pro Pro Pro Pro Pro Pro Gln Glu Thr Val Val Gln Ala Pro Val
    130                 135                 140

Phe Ser Ile Ala Asp Ile Pro Ala Ala Thr Val Ala Gly Met Pro Ala
145                 150                 155                 160

Ser Tyr Asp Leu Ser Ser Leu Phe Glu Pro Thr Gly Gln Gln Asn Ser
                165                 170                 175

Trp Gly Gly Gly Gly Ile Asp Pro Arg Gln Phe Leu Ala Val Gly Pro
            180                 185                 190

Ser Ser Thr Thr Asp Ala Asp Leu Gln Ala Met Ala Arg Asp Leu Ser
```

```
                195                 200                 205
Glu Arg Leu Ala Ser Leu Pro Pro Ala Pro Ala Pro Ala Phe Ala
    210                 215                 220

Pro Leu Pro Pro Leu Pro Pro Ala Pro Ala Pro Ala Pro Ala Pro Ser
225                 230                 235                 240

Cys Pro Asn Ala Pro Ser Ser Leu Ser Leu Ser
                245                 250

<210> SEQ ID NO 50
<211> LENGTH: 1847
<212> TYPE: DNA
<213> ORGANISM: Glycine max
<220> FEATURE:
<221> NAME/KEY: misc_feature
<223> OTHER INFORMATION: sdr1f.pk005.d21:fis

<400> SEQUENCE: 50
gtacgaggac ccctcactct tccatactat agtcctcaga ttttagttt gcaccatttc      60
ctagtgtgcc cgtgtgccta caaattttat tcacttcctc ccactcaggt cctttctttt    120
caaacataaa atacatatct ttctctctct cggtaatgac tccaacttat tgatagtgtt    180
ttatgttcag ataatgcccg atgactttgt catgcagctc caccgatttt gagaacgaca    240
gcgacttccg tccagccgt gccaggtgct gcctcagatt caggttatgc cgctcaattc     300
gctgcgtata tcgcttgctg attacgtgca gctttcccct caggcgggat tcatacagcg    360
gccagccatc cgtcatccat atcaccacgt caaagggtga cagcaggctc ataagacgcc    420
ccagcgtcgc catagtgcgt tcaccgaata cgtgcgcaac aaccgtcttc cggagactgt    480
catacgcgta aaacagccag cgctggcgcg atttagcccc gacatagccc cactgttcgt    540
ccatttccgc gcagacgatg acgtcactgc ccggctgtat gcgcgaggtt accgactgcg    600
gcctgagttt tttaagtgac gtaaaatcgt gttgaggcca acgccataa tgcgggctgt     660
tgcccggcat ccaacgccat tcatggccat atcaatgatt ttctggtgcg taccgggttg    720
agaagcggtg taagtgaact gcagttgcca tgttttacgg cagtgagagc agagatagcg    780
ctgatgtccg gcggtgcttt tgccgttacg caccacccg tcagtagctg aacaggaggg     840
acagctgata gaaacagaag ccactggagc acctcaaaaa caccatcata cactaaatca    900
gtaagttggc agcatcaccc tctctctctt tgtgtgttgg ttattagtac aattatacta    960
ctactatact atggcttctg ctagtggaaa tggtgtctct aatggctctg gctctccttg   1020
cggggcatgc aagttcctca gaagaaggtg tgcttctgat tgtatctttg caccttactt   1080
ttgttcagaa cagggccctg ctagattgc agccatacac aaggtatttg gtgccagcaa    1140
cgtttcaaag ttgcttttgc acataccagc tcatgatcgt tgtgaagcgg ttgtcacaat   1200
cacttatgag gctcaggctc gtattagaga ccctgtctat ggctgtgtct ctcacatttt   1260
tgccttacaa caacaggtgg cacgcttgca ggcacagctg atgcaggtaa agctcagct    1320
gactcagaac ctagtggagt ccaggaacat agagaataat catcatttgc aagggaataa   1380
taacaatgtt acaggacaac taatgaatca tccattttgt ccccccttaca tgaatcctat  1440
atctcctcaa agctcacttg aatcaattga tcacagcagc atcaatgatg aatgagcat   1500
gcaagatata caaagcagag aggatttcca aatccaagct aaagaaagac catacaacaa   1560
caatgacttg ggggagctgc aagaactggc actaaggatg atgaggaact gattaattat   1620
gactaggtta gcaccaaagc tagccttttc attttctaga agggtgttcc ttgatgttta   1680
gggggggatg gtcttttgct agtgttgtat atataatgag tgtcatgaag aaaaactggt   1740
```

```
cataactgat aataagccta aagtttaaac taagcattag gcttttttct gtttgtggat   1800
tcaatccaaa agaaaattaa ttttttgcaa aaaaaaaaaa aaaaaaa                1847

<210> SEQ ID NO 51
<211> LENGTH: 213
<212> TYPE: PRT
<213> ORGANISM: Glycine max
<220> FEATURE:
<221> NAME/KEY: MISC_FEATURE
<223> OTHER INFORMATION: sdr1f.pk005.d21:fis

<400> SEQUENCE: 51

Met Ala Ser Ala Ser Gly Asn Gly Val Ser Asn Gly Ser Gly Ser Pro
1               5                   10                  15

Cys Gly Ala Cys Lys Phe Leu Arg Arg Arg Cys Ala Ser Asp Cys Ile
            20                  25                  30

Phe Ala Pro Tyr Phe Cys Ser Glu Gln Gly Pro Ala Arg Phe Ala Ala
        35                  40                  45

Ile His Lys Val Phe Gly Ala Ser Asn Val Ser Lys Leu Leu Leu His
    50                  55                  60

Ile Pro Ala His Asp Arg Cys Glu Ala Val Val Thr Ile Thr Tyr Glu
65                  70                  75                  80

Ala Gln Ala Arg Ile Arg Asp Pro Val Tyr Gly Cys Val Ser His Ile
                85                  90                  95

Phe Ala Leu Gln Gln Gln Val Ala Arg Leu Gln Ala Gln Leu Met Gln
            100                 105                 110

Val Lys Ala Gln Leu Thr Gln Asn Leu Val Glu Ser Arg Asn Ile Glu
        115                 120                 125

Asn Asn His His Leu Gln Gly Asn Asn Asn Val Thr Gly Gln Leu
    130                 135                 140

Met Asn His Pro Phe Cys Pro Pro Tyr Met Asn Pro Ile Ser Pro Gln
145                 150                 155                 160

Ser Ser Leu Glu Ser Ile Asp His Ser Ser Ile Asn Asp Gly Met Ser
                165                 170                 175

Met Gln Asp Ile Gln Ser Arg Glu Asp Phe Gln Ile Gln Ala Lys Glu
            180                 185                 190

Arg Pro Tyr Asn Asn Asn Asp Leu Gly Glu Leu Gln Glu Leu Ala Leu
        195                 200                 205

Arg Met Met Arg Asn
    210

<210> SEQ ID NO 52
<211> LENGTH: 852
<212> TYPE: DNA
<213> ORGANISM: Triticum aestivum
<220> FEATURE:
<221> NAME/KEY: misc_feature
<223> OTHER INFORMATION: wdr1f.pk002.l10:fis

<400> SEQUENCE: 52
gcagagctcg atcataagct agctagtcag gccaggcggg cgatcggacg atcgggctat     60
aatttcgact acggcgacga tggccggcgc gggcgtgacg acgacggggt cgccgtgcgg    120
ggcgtgcaag ttcctgcggc gccggtgcgc ggcggagtgc gtgttcgcgc cctacttctg    180
cgccgaggac ggcgcgtcgc agttcgcggc catccacaag gtgttcgggg ccagcaacgc    240
ggccaagctg ctgcagcagg tggcccccgg cgaccggagc gaggcggccg ccacagtgac    300
```

```
ctacgaggcg caggcccggc tgcgcgaccc cgtctacggc tgcgtcgccc acatcttcgc    360
gctgcagcag caggttgtgg cgctgcaggc gcaggtggcg cacgccagga cgcaggcgca    420
gctgggggcg gcgacggcga tgcacccgct gctccagcag cagctgcagc agcaggcgtg    480
gcaggtggcc gccgccgcgg atcagcacga ccaccagtcc atgacgtcca cgcagagcag    540
ctccggctgc tacagcggcg cccaccagcc ctccgacggc tcgtcgctgc acggcgccga    600
gatgtactgc ggctacggcg agcaggagga aggcagctac taaccccag atgattgatt    660
cactcgttcc tcgttcgttc ccctgagaaa cctgagacat gtgccatgaa agtttctcc    720
tttgcaacgc gcgttcgctt gagttggttc aactcttgcc ggtctcggct gtaaaggcat    780
caatcggtct tgtgttgttt ggggctcaag acgaacccat aatttccaac tttgcaaaaa    840
aaaaaaaaaa aa                                                         852
```

<210> SEQ ID NO 53
<211> LENGTH: 187
<212> TYPE: PRT
<213> ORGANISM: Triticum aestivum
<220> FEATURE:
<221> NAME/KEY: MISC_FEATURE
<223> OTHER INFORMATION: wdr1f.pk002.l10:fis

<400> SEQUENCE: 53

```
Met Ala Gly Ala Gly Val Thr Thr Thr Gly Ser Pro Cys Gly Ala Cys
 1               5                  10                  15

Lys Phe Leu Arg Arg Arg Cys Ala Ala Glu Cys Val Phe Ala Pro Tyr
            20                  25                  30

Phe Cys Ala Glu Asp Gly Ala Ser Gln Phe Ala Ala Ile His Lys Val
        35                  40                  45

Phe Gly Ala Ser Asn Ala Ala Lys Leu Leu Gln Gln Val Ala Pro Gly
    50                  55                  60

Asp Arg Ser Glu Ala Ala Thr Val Thr Tyr Glu Ala Gln Ala Arg
65                  70                  75                  80

Leu Arg Asp Pro Val Tyr Gly Cys Val Ala His Ile Phe Ala Leu Gln
                85                  90                  95

Gln Gln Val Val Ala Leu Gln Ala Gln Val Ala His Ala Arg Thr Gln
            100                 105                 110

Ala Gln Leu Gly Ala Ala Thr Ala Met His Pro Leu Leu Gln Gln Gln
        115                 120                 125

Leu Gln Gln Gln Ala Trp Gln Val Ala Ala Ala Asp Gln His Asp
    130                 135                 140

His Gln Ser Met Thr Ser Thr Gln Ser Ser Ser Gly Cys Tyr Ser Gly
145                 150                 155                 160

Ala His Gln Arg Ser Asp Gly Ser Ser Leu His Gly Ala Glu Met Tyr
                165                 170                 175

Cys Gly Tyr Gly Glu Gln Glu Glu Gly Ser Tyr
            180                 185
```

<210> SEQ ID NO 54
<211> LENGTH: 262
<212> TYPE: PRT
<213> ORGANISM: Arabidopsis thaliana
<220> FEATURE:
<221> NAME/KEY: MISC_FEATURE
<223> OTHER INFORMATION: NCBI General Identifier No. 17227164

<400> SEQUENCE: 54

Met Ser Gly Gly Gly Asn Thr Ile Thr Ala Val Gly Gly Gly Gly Gly

```
                1               5                   10                  15
Gly Cys Gly Gly Gly Ser Ser Gly Gly Gly Ser Ser Gly Gly
                    20                  25                  30

Gly Gly Gly Gly Pro Cys Gly Ala Cys Lys Phe Leu Arg Arg Lys Cys
                    35                  40                  45

Val Pro Gly Cys Ile Phe Ala Pro Tyr Phe Asp Ser Glu Gln Gly Ser
            50                  55                  60

Ala Tyr Phe Ala Ala Val His Lys Val Phe Gly Ala Ser Asn Val Ser
65                  70                  75                  80

Lys Leu Leu Leu His Ile Pro Val His Arg Arg Ser Asp Ala Val Val
                    85                  90                  95

Thr Ile Cys Tyr Glu Ala Gln Ala Arg Ile Arg Asp Pro Ile Tyr Gly
                    100                 105                 110

Cys Val Ala His Ile Phe Ala Leu Gln Gln Gln Val Val Asn Leu Gln
                    115                 120                 125

Ala Glu Val Ser Tyr Leu Gln Ala His Leu Ala Ser Leu Glu Leu Pro
            130                 135                 140

Gln Pro Gln Thr Arg Pro Gln Pro Met Pro Gln Pro Gln Pro Leu Phe
145                 150                 155                 160

Phe Thr Pro Pro Pro Leu Ala Ile Thr Asp Leu Pro Ala Ser Val
                    165                 170                 175

Ser Pro Leu Pro Ser Thr Tyr Asp Leu Ala Ser Ile Phe Asp Gln Thr
                    180                 185                 190

Thr Ser Ser Ser Ala Trp Ala Thr Gln Gln Arg Arg Phe Ile Asp Pro
            195                 200                 205

Arg His Gln Tyr Gly Val Ser Ser Ser Ser Ser Val Ala Val Gly
            210                 215                 220

Leu Gly Gly Glu Asn Ser His Asp Leu Gln Ala Leu Ala His Glu Leu
225                 230                 235                 240

Leu His Arg Gln Gly Ser Pro Pro Ala Ala Thr Asp His Ser Pro
                    245                 250                 255

Ser Arg Thr Met Ser Arg
                    260

<210> SEQ ID NO 55
<211> LENGTH: 22
<212> TYPE: PRT
<213> ORGANISM: Artificial Sequence
<220> FEATURE:
<223> OTHER INFORMATION: C-block consensus
<220> FEATURE:
<221> NAME/KEY: MISC_FEATURE
<222> LOCATION: (11)..(11)
<223> OTHER INFORMATION: Lys or Arg
<220> FEATURE:
<221> NAME/KEY: MISC_FEATURE
<222> LOCATION: (13)..(13)
<223> OTHER INFORMATION: Val, Gln, or Ala
<220> FEATURE:
<221> NAME/KEY: MISC_FEATURE
<222> LOCATION: (14)..(14)
<223> OTHER INFORMATION: Any amino acid
<220> FEATURE:
<221> NAME/KEY: MISC_FEATURE
<222> LOCATION: (15)..(15)
<223> OTHER INFORMATION: Gly, Asp, or Glu
<220> FEATURE:
<221> NAME/KEY: MISC_FEATURE
<222> LOCATION: (17)..(17)
<223> OTHER INFORMATION: Val or Ile
<220> FEATURE:
<221> NAME/KEY: MISC_FEATURE
```

```
<222> LOCATION: (20)..(20)
<223> OTHER INFORMATION: Tyr or His
<220> FEATURE:
<221> NAME/KEY: misc_feature
<222> LOCATION: (21)..(21)
<223> OTHER INFORMATION: Xaa can be any naturally occurring amino acid

<400> SEQUENCE: 55

Pro Cys Gly Ala Cys Lys Phe Leu Arg Arg Xaa Cys Xaa Xaa Xaa Cys
1               5                   10                  15

Xaa Phe Ala Pro Xaa Phe
            20

<210> SEQ ID NO 56
<211> LENGTH: 12
<212> TYPE: PRT
<213> ORGANISM: Artificial Sequence
<220> FEATURE:
<223> OTHER INFORMATION: N-terminus of the GAS block 49 amino acids
<220> FEATURE:
<221> NAME/KEY: MISC_FEATURE
<222> LOCATION: (4)..(4)
<223> OTHER INFORMATION: Val or Ile

<400> SEQUENCE: 56

Phe Ala Ala Xaa His Lys Val Phe Gly Ala Ser Asn
1               5                   10

<210> SEQ ID NO 57
<211> LENGTH: 9
<212> TYPE: PRT
<213> ORGANISM: Artificial Sequence
<220> FEATURE:
<223> OTHER INFORMATION: C-terminus of GAS block 49 amino acids
<220> FEATURE:
<221> NAME/KEY: MISC_FEATURE
<222> LOCATION: (4)..(4)
<223> OTHER INFORMATION: Val or Ile
<220> FEATURE:
<221> NAME/KEY: MISC_FEATURE
<222> LOCATION: (5)..(5)
<223> OTHER INFORMATION: Phe or Tyr
<220> FEATURE:
<221> NAME/KEY: MISC_FEATURE
<222> LOCATION: (9)..(9)
<223> OTHER INFORMATION: Ala OR Ser

<400> SEQUENCE: 57

Arg Asp Pro Xaa Xaa Gly Cys Val Xaa
1               5

<210> SEQ ID NO 58
<211> LENGTH: 19
<212> TYPE: PRT
<213> ORGANISM: Artificial Sequence
<220> FEATURE:
<223> OTHER INFORMATION: Leucine zipper motif
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (5)..(7)
<223> OTHER INFORMATION: any amino acid
<220> FEATURE:
<221> NAME/KEY: MISC_FEATURE
<222> LOCATION: (10)..(11)
<223> OTHER INFORMATION: any amino acid
<220> FEATURE:
<221> NAME/KEY: MISC_FEATURE
<222> LOCATION: (12)..(12)
```

```
<223> OTHER INFORMATION: Leu or Val
<220> FEATURE:
<221> NAME/KEY: MISC_FEATURE
<222> LOCATION: (13)..(18)
<223> OTHER INFORMATION: any amino acid
<220> FEATURE:
<221> NAME/KEY: MISC_FEATURE
<222> LOCATION: (19)..(19)
<223> OTHER INFORMATION: Leu, Val, or Ala

<400> SEQUENCE: 58

Leu Gln Xaa Gln Xaa Xaa Xaa Leu Gln Xaa Xaa Xaa Xaa Xaa Xaa Xaa
1               5                   10                  15

Xaa Xaa Xaa

<210> SEQ ID NO 59
<211> LENGTH: 31
<212> TYPE: DNA
<213> ORGANISM: Artificial Sequence
<220> FEATURE:
<223> OTHER INFORMATION: Oligonucleotide primer cpi BbsI F

<400> SEQUENCE: 59
gaagaccaat gagcgctggc ggcggcagca g                              31

<210> SEQ ID NO 60
<211> LENGTH: 34
<212> TYPE: DNA
<213> ORGANISM: Artificial Sequence
<220> FEATURE:
<223> OTHER INFORMATION: Oligonucleotide primer Cpi BsaI R

<400> SEQUENCE: 60
ggtctcctca tcttgagtgt ggcggcgggt gctc                           34

<210> SEQ ID NO 61
<211> LENGTH: 1855
<212> TYPE: DNA
<213> ORGANISM: Zea mays

<400> SEQUENCE: 61
tatgcatcca acgcgttggg agctctccca tatggtcgac ctgcaggcgg ccgcgaattc    60
actagtgatt gaagaccaat gagcgctggc ggcggcagca gcacgcttgg cggcggggc   120 ccgagcggca gcggcagcgg aggccctgga ggaagcggcg gcggcgggcc ttgcggcgcg   180
tgcaagttcc tccggcgcaa gtgcgtcagc ggctgcatct tcgcgcccta cttcgactcg   240
gagcagggcg cggcgcactt cgcggccgtg cacaaggtgt tcggcgccag caacgtgtcc   300
aagctgctgc tccagatccc ggcgcacaag cgcctcgacg ccgtcgtcac catctgctac   360
gaggcccagg cgcggctccg cgaccccgtc tacggctgcg tcgcccacat cttcgcgctc   420
cagcagcagg tatatatatg agatgctagg atgatcgatt atctttgggt tgggttatat   480
atatattcgg tccatccatc catgcaagat ccatccatgg gctcgctcgc tagtagcttg   540
gcatgcatgc acgcatgcat ggatcgatca tggatagacg atgcctgcta gtagtaggcc   600
ggcaggcgct accagcgatt attgctgcat gatttcccct tcgcattcgc gtgtggatct   660
gggtcttttc tgaatccgcc gtctctgcga taagattctg ggagcggcca ggcgtgtttc   720
tttctcgagg aaggcaagtc cgtccccgtc ccccccttc acgaggaaat caacactgac   780
aagccaagca acggcagtgc aaaaagaagc acgccaagcg ctaatccggg aggcctgcct   840
gcggcgatga atgatatgca cttctcatcc gtcgcatccg tgccgtcgat cgcattcctc   900
```

-continued

```
ttctacccgt caaggcagca gccacgtaca ccatgcggat gcatgtgatg tgtgtgtgtg    960
tgtgtgtgta tctccttcta tcttgggctc tgcacaaagc cttccaatgc cagtggcggt   1020
gtggtgcttc ccgatctgat cgatcgatga ctcgatgagc tagccctcct tgaaaagaat   1080
agaacgtcag cgccaatctc tagtattggt agcagcagta gccgtcctcc tcctaggtag   1140
aagatccaaa cctgcattct tttttgtcaa tcgtgcgatg gacacctttc atttcgatcg   1200
catatttgca tccgtgtgtg tgatgtgtct tttttttct tccatattat atgcatctgt    1260
atcgtgtaca aacaatgatg gcttttggtg gttccaagtt tgcacgtaac aatttactgt   1320
tggatcgtcg acggtgcatg aatgtcacgt cattattccc caggtggtga atctccaggc   1380
cgagctgacc tacctgcaag cacacctcgc cacgctcgag ctgccggccc cgcccccgct   1440 gccggcccg ccgcagatgc ccatgccagg cccgttctcc atctcggacc tgccgttgtc    1500
gaccagcgtc cccaccaccg tcgacctgtc cgcgctcttc gacccgccac caccgcagtg   1560
ggcgacggcg cagcagccgc accaccacca tcaacagccg ccgcagcacc accagctccg   1620
gcaaccggcg ccgtatggcg ctggcgcgtc cgtcaggccc ggcggcggcc ccggcatggc   1680
agagagctca ggcggagacg agctgcagtc gctggcgagg gagctcctgg accgccaccg   1740
gtccggcggc gtgaagctcg agcacccgcc gccacactca agatgaggag accaatcgaa   1800
ttcccgcggc cgccatggcg gcccgggagc atgcgacgtc gggcccaatt cgccc         1855
```

<210> SEQ ID NO 62
<211> LENGTH: 40
<212> TYPE: DNA
<213> ORGANISM: Artificial Sequence
<220> FEATURE:
<223> OTHER INFORMATION: Oligonucleotide primer RE2 pro Bst 2F

<400> SEQUENCE: 62

```
caccatcatg tcagtgtgcc aatacgctaa acttagaaga                            40
```

<210> SEQ ID NO 63
<211> LENGTH: 30
<212> TYPE: DNA
<213> ORGANISM: Artificial Sequence
<220> FEATURE:
<223> OTHER INFORMATION: Oligonucleotide primer RE2 PRO R BbsI

<400> SEQUENCE: 63

```
gaagacgctc attcttggaa tgagcccca                                        30
```

<210> SEQ ID NO 64
<211> LENGTH: 4359
<212> TYPE: DNA
<213> ORGANISM: Artificial
<220> FEATURE:
<223> OTHER INFORMATION: pGEMT-easy vector with portion of rice RE2
      promoter

<400> SEQUENCE: 64

```
gggcgaattg ggcccgacgt cgcatgctcc cggccgccat ggcggccgcg ggaattcgat      60
tcaccatcat gtcagtgtgc caatacgcta aacttagaag atgcctccga taatcgtagc    120
atttgtatta tttggggaat gaattaaawa atataaataa tgatatatta caattgataa    180
tctatgttta gaaactttg tcggttactc gctcaaattg tatggggtaa taaatcggtg    240
aagtatattt ttatactgaa tggaaaagat aagctaccat tgatagcatt agcggttcta    300
tttcgtatat tatcccgatt atccaccctc aatttgtgct aaaataagat ttttacatca    360
```

```
tcctagtcaa tatttggggt tacccctgtct gcattataat ttattttgt gcttaactat    420
aatatataca tacactataa tttatctaaa taaaagttct ggtatgattg aaaaaaacta    480
acaattttgt gtgtggcgta ttgagtggaa gaatgtcatg ttaggatcac atgggagaga    540
gtgcatgcga cgagatcatc cttgttggtc tgtgcaggtg gtgtgaaatg tgatcaatat    600
atatggtggt gacagagaga gaaactaacc caaaaaaaca aaaaagaga gatgagagcg    660
aatggatgga tgcaattggc attaattttc ggtctttgct gttctccccc agccaggcca    720
gtttgcttca cgcaatattc taaccctttg agaaagagaa gtgtacttgt tgccaaggcc    780
aattgcaagc atttgccttg gctttaaagt ctcatcaata caacggcacc aaaaagaaaa    840
cacatagaga tagaaaacca cctagtagct gatatacatt tatatatgac ctaaataaaa    900
aaattccatt aatatrtata attccagcaa caacataaag aaataaaaat gcatttaaga    960
aaacatagaa agaaataaaa ataaagtaaa taaagctagc taggcccaaa attggcagta   1020
attaagtagg gactagtata gaaatatatg gatatataca ccagcctcca ccaatgggat   1080
tgcaaacagc ctacttatca ctttgctgct gtatttacgc ttttgcccctt cttccctcct   1140
atatgtacag ccgcccccmac ctcattccct ccattcttac tccacacaca cactctctct   1200
ctctaccatt tgtgagaaag aaaatcgatt cagttctaga gagagaaaca aacaattttc   1260
gctgtctatc tctctcttgc tactagtcgg tcgatcttga gttagtttta accctacaca   1320
agccaaggta acaacatcta gcaggtagga gaagagtgct agagactagg tggtggggc    1380
tcattccaag aatgagcgtc ttcaatcact agtgaattcg cggccgcctg caggtcgacc   1440
atatgggaga gctcccaacg cgttggatgc atagcttgag tattctatag tgtcacctaa   1500
atagcttggc gtaatcatgg tcatagctgt ttcctgtgtg aaattgttat ccgctcacaa   1560
ttccacacaa catacgagcc ggaagcataa agtgtaaagc ctggggtgcc taatgagtga   1620
gctaactcac attaattgcg ttgcgctcac tgcccgcttt ccagtcggga aacctgtcgt   1680
gccagctgca ttaatgaatc ggccaacgcg cggggagagg cggtttgcgt attgggcgct   1740
cttccgcttc ctcgctcact gactcgctgc gctcggtcgt tcggctgcgg cgagcggtat   1800
cagctcactc aaaggcggta atacggttat ccacagaatc aggggataac gcaggaaaga   1860
acatgtgagc aaaaggccag caaaaggcca ggaaccgtaa aaaggccgcg ttgctggcgt   1920
ttttccatag gctccgcccc cctgacgagc atcacaaaaa tcgacgctca agtcagaggt   1980
ggcgaaaccc gacaggacta taaagatacc aggcgtttcc ccctggaagc tccctcgtgc   2040
gctctcctgt tccgaccctg ccgcttaccg gatacctgtc cgcctttctc ccttcgggaa   2100
gcgtggcgct ttctcatagc tcacgctgta ggtatctcag ttcggtgtag gtcgttcgct   2160
ccaagctggg ctgtgtgcac gaaccccccg ttcagcccga ccgctgcgcc ttatccggta   2220
actatcgtct tgagtccaac ccggtaagac acgacttatc gccactggca gcagccactg   2280
gtaacaggat tagcagagcg aggtatgtag gcggtgctac agagttcttg aagtggtggc   2340
ctaactacgg ctacactaga agaacagtat ttggtatctg cgctctgctg aagccagtta   2400
ccttcggaaa aagagttggt agctcttgat ccggcaaaca aaccaccgct ggtagcggtg   2460
gtttttttgt ttgcaagcag cagattacgc gcagaaaaaa aggatctcaa gaagatcctt   2520
tgatcttttc tacggggtct gacgctcagt ggaacgaaaa ctcacgttaa gggattttgg   2580
tcatgagatt atcaaaaagg atcttcacct agatcctttt aaattaaaaa tgaagtttta   2640
aatcaatcta agtatatat gagtaaactt ggtctgacag ttaccaatgc ttaatcagtg   2700
aggcacctat ctcagcgatc tgtctatttc gttcatccat agttgcctga ctccccgtcg   2760
```

```
tgtagataac tacgatacgg gagggcttac catctggccc cagtgctgca atgataccgc    2820
gagacccacg ctcaccggct ccagatttat cagcaataaa ccagccagcc ggaagggccg    2880
agcgcagaag tggtcctgca actttatccg cctccatcca gtctattaat tgttgccggg    2940
aagctagagt aagtagttcg ccagttaata gtttgcgcaa cgttgttgcc attgctacag    3000
gcatcgtggt gtcacgctcg tcgtttggta tggcttcatt cagctccggt tcccaacgat    3060
caaggcgagt tacatgatcc cccatgttgt gcaaaaaagc ggttagctcc ttcggtcctc    3120
cgatcgttgt cagaagtaag ttggccgcag tgttatcact catggttatg gcagcactgc    3180
ataattctct tactgtcatg ccatccgtaa gatgcttttc tgtgactggt gagtactcaa    3240
ccaagtcatt ctgagaatag tgtatgcggc gaccgagttg ctcttgcccg gcgtcaatac    3300
gggataatac cgcgccacat agcagaactt taaaagtgct catcattgga aaacgttctt    3360
cggggcgaaa actctcaagg atcttaccgc tgttgagatc cagttcgatg taacccactc    3420
gtgcacccaa ctgatcttca gcatctttta ctttcaccag cgtttctggg tgagcaaaaa    3480
caggaaggca aaatgccgca aaaaagggaa taagggcgac acggaaatgt tgaatactca    3540
tactcttcct ttttcaatat tattgaagca tttatcaggg ttattgtctc atgagcggat    3600
acatatttga atgtatttag aaaaataaac aaatagggt tccgcgcaca tttccccgaa    3660
aagtgccacc tgatgcggtg tgaaataccg cacagatgcg taaggagaaa ataccgcatc    3720
aggaaattgt aagcgttaat attttgttaa aattcgcgtt aaattttttgt taaatcagct    3780 cattttttaa ccaataggcc gaaatcggca aaatccctta taaatcaaaa gaatagaccg    3840
agatagggtt gagtgttgtt ccagtttgga acaagagtcc actattaaag aacgtggact    3900
ccaacgtcaa agggcgaaaa accgtctatc agggcgatgg cccactacgt gaaccatcac    3960
cctaatcaag ttttttgggg tcgaggtgcc gtaaagcact aaatcggaac cctaaaggga    4020
gcccccgatt tagagcttga cggggaaagc cggcgaacgt ggcgagaaag gaagggaaga    4080
aagcgaaagg agcgggcgct agggcgctgg caagtgtagc ggtcacgctg cgcgtaacca    4140
ccacacccgc cgcgcttaat gcgccgctac agggcgcgtc cattcgccat tcaggctgcg    4200
caactgttgg gaagggcgat cggtgcgggc ctcttcgcta ttacgccagc tggcgaaagg    4260
gggatgtgct gcaaggcgat taagttgggt aacgccaggg ttttcccagt cacgacgttg    4320
taaaacgacg gccagtgaat tgtaatacga ctcactata                           4359
```

<210> SEQ ID NO 65
<211> LENGTH: 38
<212> TYPE: DNA
<213> ORGANISM: Artificial Sequence
<220> FEATURE:
<223> OTHER INFORMATION: Oligonucleotide primer RE2 TERM XbaI R

<400> SEQUENCE: 65

```
gtaaaaggat ctagacacct ggctctagcc tccaagta                             38
```

<210> SEQ ID NO 66
<211> LENGTH: 50
<212> TYPE: DNA
<213> ORGANISM: Artificial Sequence
<220> FEATURE:
<223> OTHER INFORMATION: Oligonucleotide primer RE2 TERM EcoBspmI

<400> SEQUENCE: 66

```
tggagcgaat tcacctgcca agatgatcct cctcactgtg tgtgatcatc                50
```

<210> SEQ ID NO 67
<211> LENGTH: 3745
<212> TYPE: DNA
<213> ORGANISM: Artificial
<220> FEATURE:
<223> OTHER INFORMATION: pGEM9z plasmid containing portion of rice RE2
      terminator

<400> SEQUENCE: 67

```
gggcgaattg ggcccgacgt cgcatgctcc tctagacacc tggctctagc ctccaagtac      60
tcacatatgt tcacactttta ttcagttgcc accatacata tatgttcagt taccattaac    120
```
(Note: line 2 reads as printed)

```
gggcgaattg ggcccgacgt cgcatgctcc tctagacacc tggctctagc ctccaagtac      60
tcacatatgt tcacacttta ttcagttgcc accatacata tatgttcagt taccattaac     120
cccaaaaatg ctcattttgc tacttgctag ctgttgtata tattatggca aaaaaaaaa      180
gctcatttgt catagagaga tcagaaagtc ccaaattaag actgactaca cttcacttca     240
gatgttcagt tagaaccttg aaacagaaat caaacaaact tcaaacacaa ccgtaattaa     300
tctgcgatga gacaaagatt ttttttttgt atattgaact aaattagacc aggttttgtt     360
ttttgcaatt agaactgttg caatggaaca gtgatcaggg ctacagctaa gctaacaaga     420
actcatcccc aagcttcctc ttttggagca aactcccaag cattataaaa tggtgcaagt     480
gggcacccct tgcaccctag cccaagaaca agatgatac gcgaaaaccg ggcaatgcct      540
gttacctacc atctccatcc ccaacatcac catcatcgtc ttcctcgcca tcgtcgtcgt     600
cgtcgttcga tttttcgcct caacgacatg gaggatttgg tgaaaaaaat ttcaccattg     660
ggattaaatt ctcttcttgc ctcaaccaat gcattcatga atgattaaca cctgatcaat     720
tagtccatga gctagctagc taagctgaat tgatgatcac acacagtgag gaggatcatc     780
ttggcaggtg aattcggtac cccgggttcg aaatcgataa gcttggatcc ggagagctcc     840
caacgcgttg gatgcatagc ttgagtattc tatagtgtca cctaaatagc ttggcgtaat     900
catggtcata gctgtttcct gtgtgaaatt gttatccgct cacaattcca cacaacatac     960
gagccggaag cataaagtgt aaagcctggg gtgcctaatg agtgagctaa ctcacattaa    1020
ttgcgttgcg ctcactgccc gctttccagt cgggaaacct gtcgtgccag ctgcattaat    1080
gaatcggcca acgcgcgggg agaggcggtt tgcgtattgg gcgctcttcc gcttcctcgc    1140
tcactgactc gctgcgctcg gtcgttcggc tgcggcgagc ggtatcagct cactcaaagg    1200
cggtaatacg gttatccaca gaatcagggg ataacgcagg aaagaacatg tgagcaaaag    1260
gccagcaaaa ggccaggaac cgtaaaaagg ccgcgttgct ggcgtttttc cataggctcc    1320
gcccccctga cgagcatcac aaaaatcgac gctcaagtca gaggtggcga acccgacag     1380
gactataaag ataccaggcg tttccccctg gaagctccct cgtgcgctct cctgttccga    1440
ccctgccgct taccggatac ctgtccgcct ttctcccttc gggaagcgtg gcgctttctc    1500
atagctcacg ctgtaggtat ctcagttcgg tgtaggtcgt tcgctccaag ctgggctgtg    1560
tgcacgaacc ccccgttcag cccgaccgct gcgccttatc cggtaactat cgtcttgagt    1620
ccaacccggt aagacacgac ttatcgccac tggcagcagc cactggtaac aggattagca    1680
gagcgaggta tgtaggcggt gctacagagt tcttgaagtg gtggcctaac tacggctaca    1740
ctagaagaac agtatttggt atctgcgctc tgctgaagcc agttaccttc ggaaaaagag    1800
ttggtagctc ttgatccggc aaacaaacca ccgctggtag cggtggtttt ttgtttgca     1860
agcagcagat tacgcgcaga aaaaaaggat ctcaagaaga tcctttgatc ttttctacgg    1920
ggtctgacgc tcagtggaac gaaaactcac gttaagggat tttggtcatg agattatcaa    1980
aaaggatctt cacctagatc cttttaaatt aaaaatgaag ttttaaatca atctaaagta    2040
```

```
tatatgagta aacttggtct gacagttacc aatgcttaat cagtgaggca cctatctcag    2100
cgatctgtct atttcgttca tccatagttg cctgactccc cgtcgtgtag ataactacga    2160
tacgggaggg cttaccatct ggccccagtg ctgcaatgat accgcgagac ccacgctcac    2220
cggctccaga tttatcagca ataaaccagc cagccggaag ggccgagcgc agaagtggtc    2280
ctgcaacttt atccgcctcc atccagtcta ttaattgttg ccgggaagct agagtaagta    2340
gttcgccagt taatagtttg cgcaacgttg ttgccattgc tacaggcatc gtggtgtcac    2400
gctcgtcgtt tggtatggct tcattcagct ccggttccca acgatcaagg cgagttacat    2460
gatcccccat gttgtgcaaa aaagcggtta gctccttcgg tcctccgatc gttgtcagaa    2520
gtaagttggc cgcagtgtta tcactcatgg ttatggcagc actgcataat tctcttactg    2580
tcatgccatc cgtaagatgc ttttctgtga ctggtgagta ctcaaccaag tcattctgag    2640
aatagtgtat gcggcgaccg agttgctctt gcccggcgtc aatacgggat aataccgcgc    2700
cacatagcag aactttaaaa gtgctcatca ttggaaaacg ttcttcgggg cgaaaactct    2760
caaggatctt accgctgttg agatccagtt cgatgtaacc cactcgtgca cccaactgat    2820
cttcagcatc ttttactttc accagcgttt ctgggtgagc aaaaacagga aggcaaaatg    2880
ccgcaaaaaa gggaataagg gcgacacgga aatgttgaat actcatactc ttcctttttc    2940
aatattattg aagcatttat cagggttatt gtctcatgag cggatacata tttgaatgta    3000
tttagaaaaa taaacaaata ggggttccgc gcacatttcc ccgaaaagtg ccacctgtat    3060
gcggtgtgaa ataccgcaca gatgcgtaag gagaaaatac cgcatcagga cgcgccctgt    3120
agcggcgcat taagcgcggc gggtgtggtg gttacgcgca gcgtgaccgc tacacttgcc    3180
agcgccctag cgcccgctcc tttcgctttc ttcccttcct ttctcgccac gttcgccggc    3240
tttccccgtc aagctctaaa tcgggggctc cctttagggt tccgatttag tgctttacgg    3300
cacctcgacc ccaaaaaact tgattagggt gatggttcac gtagtgggcc atcgccctga    3360
tagacggttt ttcgcccttt gacgttggag tccacgttct ttaatagtgg actcttgttc    3420
caaactggaa caacactcaa ccctatctcg gtctattctt ttgatttata agggattttg    3480
ccgatttcgg cctattggtt aaaaaatgag ctgatttaac aaaaatttaa cgcgaatttt    3540
aacaaaatat taacgcttac aatttccatt cgccattcag gctgcgcaac tgttgggaag    3600
ggcgatcggt gcgggcctct tcgctattac gccagctggc gaaagggggga tgtgctgcaa    3660 ggcgattaag ttgggtaacg ccagggtttt cccagtcacg acgttgtaaa acgacggcca    3720
gtgaattgta atacgactca ctata                                         3745
```

<210> SEQ ID NO 68
<211> LENGTH: 27
<212> TYPE: DNA
<213> ORGANISM: Artificial Sequence
<220> FEATURE:
<223> OTHER INFORMATION: oligonucleotide primer that may be used to
      identify RE2 homologs

<400> SEQUENCE: 68
gcatcttcgc gccctacttc gactcgg                                         27

<210> SEQ ID NO 69
<211> LENGTH: 35
<212> TYPE: DNA
<213> ORGANISM: Artificial Sequence
<220> FEATURE:
<223> OTHER INFORMATION: oligonucleotide primer that may be used to
      identify RE2 homologs

<400> SEQUENCE: 69

```
gcacaaggtg ttcggcgcca gcaacgtgtc caagc                              35
```

<210> SEQ ID NO 70
<211> LENGTH: 34
<212> TYPE: DNA
<213> ORGANISM: Artificial Sequence
<220> FEATURE:
<223> OTHER INFORMATION: oligonucleotide primer that may be used to
      identify RE2 homologs

<400> SEQUENCE: 70

```
ccgcgacccc gtctacggct gcgtcgccca cctc                               34
```

<210> SEQ ID NO 71
<211> LENGTH: 448
<212> TYPE: DNA
<213> ORGANISM: Artificial Sequence
<220> FEATURE:
<223> OTHER INFORMATION: Probe used to identify RE2 cDNA

<400> SEQUENCE: 71

```
gcaggtctcc agtccgagct gaactacctg caaggtcacc tctcgacgat ggagctgccg    60
tcgccgccgc cctacgtcgc cgggccgacc ctggcgccgc cacagccaca gccactgatg   120
ccgatgaccg ccgccgccaa cttcaacttc tccgacctgc catcgtcgtc ggcggccaac   180
attccggtca ccgccgacct gtccaccctc tttgacccac tgccggcggc gcagccgcag   240
tggggactat accagcagca gcaacaccac caccagcagc tgcatcatca cccctatgac   300
cggatgggcg acggctcgtc gagcagcaga ggcggcgacg acgatggcag cgacggcggc   360
gacttgcaag cgctggcgag ggagcttctt gaccgccatg gacggtcgtc gtcgagctcc   420
aagctggagc cgccacctca cacacagt                                      448
```

<210> SEQ ID NO 72
<211> LENGTH: 1500
<212> TYPE: DNA
<213> ORGANISM: Oryza sativa

<400> SEQUENCE: 72

```
ggcacgaggt ctctctctac catttgtgag aaagaaaatc gattcagttc tagagagaga    60
aacaaacaat tttcgctgtc tatctctctc ttgctactag tcggtcgatc ttgagttagt   120
tttaaccta cacaagccaa ggtaacaaca tctagcaggt aggagaagag agctagagac    180
taggtggtgg gggctcattc caagaatgag ctcgtcggtg gttgtgagcg cgagcggcag   240
cggcagcggc ggcggaggag gaggaggagg tggcggcgcc ggaggtggag gaggaggtgg   300
gccgtgcggg gcgtgcaagt tcttgcggcg gaagtgcgtg cagggtgca tcttcgcgcc   360
ctacttcgac tcggaggccg gggcggcgca cttcgcggcg gtgcacaagg tgttcggcgc   420
cagcaacgtg tccaagctgc tgcagcagat cccggcgcac cgccgcctcg acgccgtcgt   480
caccatctgc tacgaggccc aggcccgcct ccgcgacccc gtctacggct gcgtcgccca   540
catcttccac ctccaacacc aggtggcagg tctccagtcc gagctgaact acctgcaagg   600
tcacctctcg acgatggagc tgccgtcgcc gccgcctac gtcgccgggc cgaccctggc   660
gccgccacag ccacagccac tgatgccgat gaccgccgcc gccaacttca acttctccga   720
cctgccatcg tcgtcggcgg ccaacattcc ggtcaccgcc gacctgtcca ccctctttga   780
cccactgccg gcggcgcagc cgcagtgggg actataccag cagcagcaac accaccacca   840
```

```
gcagctgcat catcacccct atgaccggat gggcgacggc tcgtcgagca gcagaggcgg    900
cgacgacgat ggcagcgacg gcggcgactt gcaagcgctg gcgagggagc ttcttgaccg    960
ccatggacgg tcgtcgtcga gctccaagct ggagccgcca cctcacacac agtgatcctc   1020
ctcactgtgt gtgatcatca attcagctta gctagctagc tcatggacta attgatcagg   1080
tgttaatcat tcatgaatgc attggttgag gcaagaagag aatttaatcc caatggtgaa   1140 attttttca ccaaatcctc catgtcgttg aggcgaaaaa tcgaacgacg acgacgacga    1200
tggcgaggaa gacgatgatg gtgatgttgg ggatggagat ggtaggtaac aggcattgcc   1260
cggttttcgc gtatcatctt tgttcttggg ctagggtgca aggggtgccc acttgcacca   1320
ttttataatg cttgggagtt tgctccaaaa gaggaagctt ggggatgagt tcttgttagc   1380
ttagctgtag ccctgatcac tgttccattg caacagttct aattgcaaaa aacaaaacct   1440
ggtctaattt agttcaatat acaaaaaaaa aatctttgtc tcaaaaaaaa aaaaaaaaaa   1500
```